United States Patent
Kato et al.

(10) Patent No.: US 10,043,977 B2
(45) Date of Patent: Aug. 7, 2018

(54) NITROGENATED AROMATIC HETEROCYCLIC DERIVATIVE, AND ORGANIC ELECTROLUMINESCENT ELEMENT USING SAME

(75) Inventors: Tomoki Kato, Chiba (JP); Nobuhiro Yabunouchi, Chiba (JP); Takahiro Fujiyama, Chiba (JP)

(73) Assignee: IDEMITSU KOSAN CO., LTD., Tokyo (JP)

(*) Notice: Subject to any disclaimer, the term of this patent is extended or adjusted under 35 U.S.C. 154(b) by 930 days.

(21) Appl. No.: 14/233,066

(22) PCT Filed: Jul. 11, 2012

(86) PCT No.: PCT/JP2012/067689
§ 371 (c)(1),
(2), (4) Date: Feb. 27, 2014

(87) PCT Pub. No.: WO2013/011891
PCT Pub. Date: Jan. 24, 2013

(65) Prior Publication Data
US 2014/0167026 A1    Jun. 19, 2014

(30) Foreign Application Priority Data

Jul. 15, 2011 (JP) ............................... 2011-156833
Aug. 1, 2011 (JP) ............................... 2011-168775

(51) Int. Cl.
*H01L 51/00* (2006.01)
*C09K 11/06* (2006.01)
(Continued)

(52) U.S. Cl.
CPC ........ *H01L 51/0052* (2013.01); *C07D 405/10* (2013.01); *C07D 405/14* (2013.01);
(Continued)

(58) Field of Classification Search
CPC ..................................................... C09B 47/00
See application file for complete search history.

(56) References Cited

U.S. PATENT DOCUMENTS 8,057,919 B2 * 11/2011 Kato .................... C07D 235/08
                                                                 313/504
2004/0113547 A1    6/2004 Son et al.
(Continued)

FOREIGN PATENT DOCUMENTS

DE    10 2009 023 155 A1    12/2010
EP         2 284 920 A1     2/2011
(Continued)

OTHER PUBLICATIONS

Sapochak et al., Designing Organic Phosphine Oxide Host Materials Using Heteroaromatic Building Blocks: Inductive Effects on Electroluminescence, Proc. of SPIE, vol. 6655, 665506, (2007), p. 1-11.*

(Continued)

*Primary Examiner* — Francisco W Tschen
(74) *Attorney, Agent, or Firm* — Oblon, McClelland, Maier & Neustadt, L.L.P.

(57) ABSTRACT

A nitrogen-containing aromatic heterocyclic derivative in which a nitrogen atom of an indenocarbazole skeleton optionally having a hetero atom or an indenoindole skeleton optionally having a hetero atom is bonded to a dibenzofuran or a dibenzothiophene directly or indirectly. The derivative realizes an organic EL device with a high emission efficiency and a long lifetime.

22 Claims, 1 Drawing Sheet

(51) Int. Cl.
*H05B 33/20* (2006.01)
*C07D 405/14* (2006.01)
*C07D 405/10* (2006.01)
*C07D 457/04* (2006.01)
*C07D 491/048* (2006.01)
*C07D 495/04* (2006.01)
*C09B 57/00* (2006.01)
*C09B 69/00* (2006.01)
*H01L 51/50* (2006.01)

(52) U.S. Cl.
CPC ....... *C07D 457/04* (2013.01); *C07D 491/048* (2013.01); *C07D 495/04* (2013.01); *C09B 57/00* (2013.01); *C09B 69/008* (2013.01); *C09K 11/06* (2013.01); *H01L 51/0071* (2013.01); *H01L 51/0072* (2013.01); *H01L 51/0073* (2013.01); *H05B 33/20* (2013.01); *C09K 2211/1007* (2013.01); *C09K 2211/1029* (2013.01); *C09K 2211/1033* (2013.01); *C09K 2211/1044* (2013.01); *C09K 2211/1059* (2013.01); *C09K 2211/1092* (2013.01); *C09K 2211/185* (2013.01); *H01L 51/0059* (2013.01); *H01L 51/0085* (2013.01); *H01L 51/5012* (2013.01)

(56) References Cited

U.S. PATENT DOCUMENTS

| | | | |
|---|---|---|---|
| 2009/0066235 A1 | 3/2009 | Yabunouchi et al. | |
| 2009/0302743 A1 | 12/2009 | Kato et al. | |
| 2009/0309488 A1 | 12/2009 | Kato et al. | |
| 2010/0012931 A1 | 1/2010 | Kato et al. | |
| 2011/0017983 A1* | 1/2011 | Mizuki | C08G 61/12 257/40 |
| 2011/0062429 A1* | 3/2011 | Kai | C07D 487/04 257/40 |
| 2012/0068170 A1 | 3/2012 | Pflumm et al. | |
| 2012/0161119 A1* | 6/2012 | Yabunouchi | C07D 307/91 257/40 |
| 2012/0241732 A1* | 9/2012 | Endo | C09B 57/00 257/40 |

FOREIGN PATENT DOCUMENTS

| | | | |
|---|---|---|---|
| EP | 2 301 921 A1 | 3/2011 | |
| JP | 2006-503443 A | 1/2006 | |
| JP | WO 2009145016 A1 * | 12/2009 | ........... C07D 307/91 |
| JP | 2010 40829 | 2/2010 | |
| JP | 2012-175025 A | 9/2012 | |
| KR | 2011 0113468 | 10/2011 | |
| WO | 2004 054326 | 6/2004 | |
| WO | 2009 136595 | 11/2009 | |
| WO | 2009 148015 | 12/2009 | |
| WO | 2009 148016 | 12/2009 | |
| WO | 2009 148062 | 12/2009 | |
| WO | WO 2010/107244 A2 | 9/2010 | |
| WO | 2010 114267 | 10/2010 | |
| WO | 2011 049063 | 4/2011 | |
| WO | WO-2011070963 A1 * | 6/2011 | ............. C09B 57/00 |
| WO | WO 2011/080972 A1 | 7/2011 | |
| WO | 2011 099374 | 8/2011 | |
| WO | 2011 136755 | 11/2011 | |
| WO | 2012 039561 | 3/2012 | |
| WO | WO 2012/165832 A1 | 12/2012 | |
| WO | WO 2012/169821 A1 | 12/2012 | |

OTHER PUBLICATIONS

Yoon et al., Highly efficient blue organic light-emitting diodes using quantum well-like multiple emissive layer structure, Nanoscale Res Lett. 2014; 9(1), 191 p. 1-7. (Year: 2014).*

Office Action dated Jun. 2, 2015 in Japanese Patent Application No. 2011-168775.

Extended European Search Report dated Dec. 1, 2014 in Patent Application No. 12814701.4.

International Search Report dated Aug. 21, 2012 in PCT/JP12/067689 Filed Jul. 11, 2012.

* cited by examiner

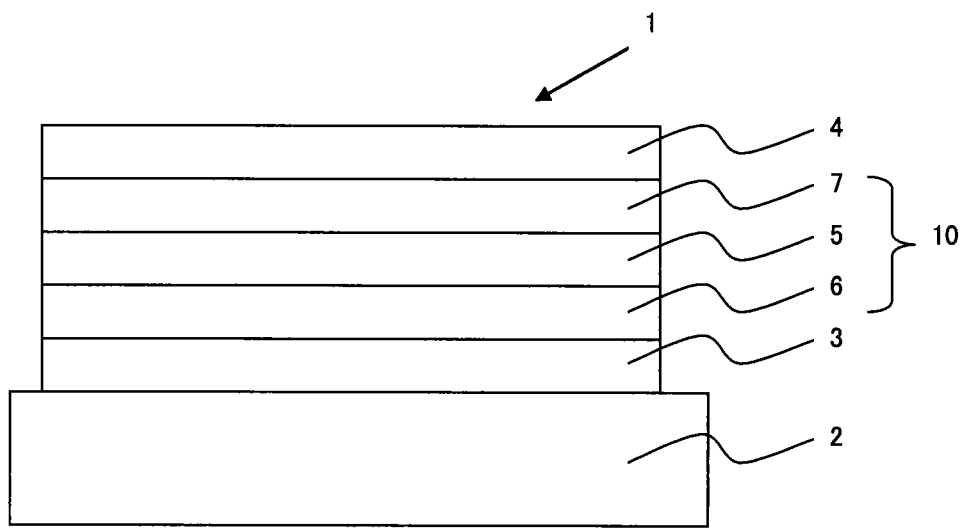

NITROGENATED AROMATIC HETEROCYCLIC DERIVATIVE, AND ORGANIC ELECTROLUMINESCENT ELEMENT USING SAME

TECHNICAL FIELD

The present invention relates to nitrogen-containing aromatic heterocyclic derivatives and organic electroluminescence devices (hereinafter also referred to as organic EL device).

BACKGROUND ART

Organic electroluminescence (EL) devices are much expected to be useful as inexpensive, large-sized full color display devices of solid state emission type and many developments have been made thereon. An organic EL device is generally constructed from a light emitting layer and a pair of opposite electrodes sandwiching the light emitting layer. When an electric field is applied between the electrodes, electrons are injected from a cathode and holes are injected from an anode into the light emitting layer. The injected electrons recombine with the injected holes in the light emitting layer to form excited states. When the excited states return to the ground state, the energy is released as light.

A phosphorescent organic EL device wherein a phosphorescent organic material is used in the light emitting layer has been proposed. Utilizing the singlet excited state and the triplet excited state of the phosphorescent organic material, a high emission efficiency can be obtained by the phosphorescent organic EL device. When electrons and holes are recombined in an organic EL device, singlet excitons and triplet excitons may generate in a ratio of 1:3 in accordance with their difference in the spin multiplicity. Therefore, an organic EL device employing the phosphorescent emitting material would achieve an emission efficiency three to four times higher than that of an organic EL device employing only the fluorescent emitting material.

The early organic EL device requires a high driving voltage and is insufficient in the emission efficiency and durability. To eliminate these problems, various technical improvements have been made.

The improved emission efficiency and the prolonged lifetime are very important for reducing the power consumption of displays and improving the durability. Therefore, further improvements have been still required. In addition, many studies have been made in order to improve the emission efficiency and the device lifetime of organic EL devices employing a phosphorescent emitting material.

A carbazole derivative has been used particularly as a phosphorescent host material because it has a high triplet energy. It has been also studied to use the carbazole derivative as a hole transporting material in the vicinity of a phosphorescent host, because the carbazole derivative makes the ionization potential (Ip) shallow to increase the hole transporting ability.

The carbazole derivative has been modified in its molecular structure. Patent Document 1 discloses a derivative having an indenoindole skeleton, Patent Document 2 discloses a derivative having an indenocarbazole skeleton, and Patent Document 3 discloses a derivative having an indolocarbazole skeleton.

PRIOR ART DOCUMENTS

Patent Documents

Patent Document 1: JP 2010-40829A
Patent Document 2: WO 2010/114267
Patent Document 3: WO 2011/049063

SUMMARY OF THE INVENTION

Problem to be Solved by the Invention

However, the inventors have found that the transporting properties of the proposed carbazole derivatives are difficult to control because of their relatively high electron transporting ability, and therefore, the recombination zone is sifted toward the hole transporting layer side to adversely affect the efficiency and lifetime.

The present invention has been made to solve the above problem and its object is to provide an organic EL material for realizing a highly efficient, long-lifetime organic EL device.

Means for Solving Problem

As a result of extensive research to achieve the above object, the inventors have found that the above problems are solved by a nitrogen-containing aromatic heterocyclic derivative wherein a nitrogen atom of an indenoindole skeleton or an indenocarbazole skeleton each optionally having a hetero atom is bonded to a carbon atom constituting the benzene ring of a fluorene skeleton which may include a hetero atom. The present invention is based on this finding.

The present invention provides:

1. A nitrogen-containing aromatic heterocyclic derivative represented by formula (1-1) or (1-2):

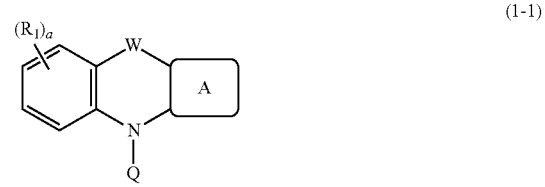

(1-1)

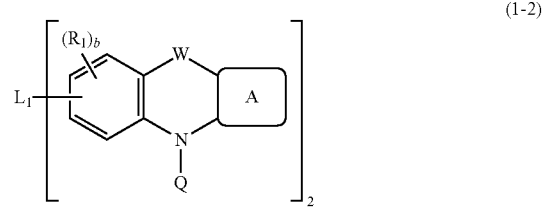

(1-2)

wherein:
a ring A is represented by formula (1a) or (1b):

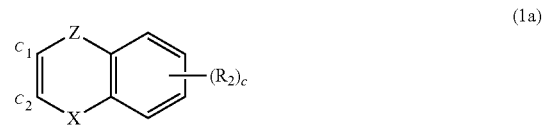

(1a)

-continued (1b)

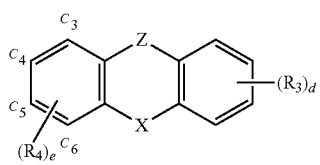

ring carbon atoms $C_1$ and $C_2$, $C_3$ and $C_4$, $C_4$ and $C_5$, or $C_5$ and $C_6$ are shared with an adjacent ring;

X represents $NR_5$, $CR_6R_7$, $SiR_6R_7$, an oxygen atom, or a sulfur atom;

each of W and Z independently represents a single bond, $CR_6R_7$, $SiR_6R_7$, an oxygen atom, or a sulfur atom;

$L_1$ represents a single bond, an arylene group having 6 to 30 ring carbon atoms, or a heteroarylene group having 5 to 30 ring atoms;

each of $R_1$ to $R_7$ independently represents a linear or branched alkyl group having 1 to 15 carbon atoms, a cycloalkyl group having 3 to 15 ring carbon atoms, a substituted or unsubstituted silyl group, an aryl group having 6 to 30 ring carbon atoms, a heteroaryl group having 5 to 30 ring atoms, a halogen atom, or a cyano group, or adjacent two groups of $R_1$ to $R_7$ are bonded to each other to from a saturated or unsaturated divalent group which completes a ring;

each of a, c and d independently represents an integer of 0 to 4;

b represents an integer of 0 to 3;

e represents an integer of 0 to 2; and

Q represents a structure represented by formula (1c):

(1c)

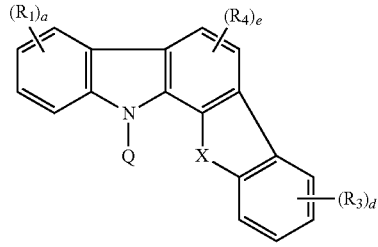

wherein:

Y represents an oxygen atom or a sulfur atom;

$L_2$ represents a single bond, an arylene group having 6 to 30 ring carbon atoms, or a heteroarylene group having 5 to 30 ring atoms, provided that when $L_2$ is bonded to a carbon atom at 2-position of the structure represented by formula (1c), $L_2$ represents an arylene group having 6 to 30 ring carbon atoms or a heteroaryl group having 5 to 30 ring atoms;

each of $R_8$ and $R_9$ independently represents a linear or branched alkyl group having 1 to 15 carbon atoms, a cycloalkyl group having 3 to 15 ring carbon atoms, a substituted or unsubstituted silyl group, an aryl group having 6 to 30 ring carbon atoms, a heteroaryl group having 5 to 30 ring atoms, a halogen atom, or a cyano group, or adjacent two groups of $R_8$ and $R_9$ are bonded to each other to from a saturated or unsaturated divalent group which completes a ring;

f represents an integer of 0 to 3; and g represents an integer of 0 to 4;

2. The nitrogen-containing aromatic heterocyclic derivative according to item 1, wherein W of formulae (1-1) and (1-2) represents a single bond and Z of formulae (1a) and (1b) represents a single bond;

3. The nitrogen-containing aromatic heterocyclic derivative according to item 2, which is represented by formula (2-1) or (2-2);

(2-1)

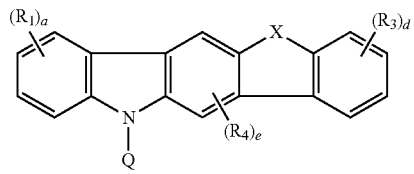

(2-2)

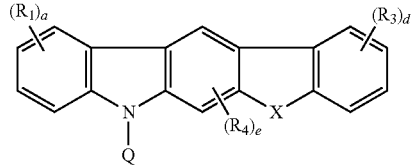

wherein $R_1$, $R_3$, $R_4$, a, d, e, X, and Q are as defined above;

4. The nitrogen-containing aromatic heterocyclic derivative according to item 2, which is represented by formula (3-1) or (3-2);

(3-1)

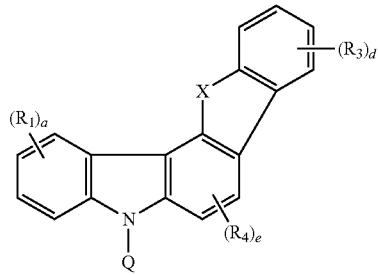

(3-2)

wherein $R_1$, $R_3$, $R_4$, a, d, e, X, and Q are as defined above;

5. The nitrogen-containing aromatic heterocyclic derivative according to item 2, which is represented by formula (4-1);

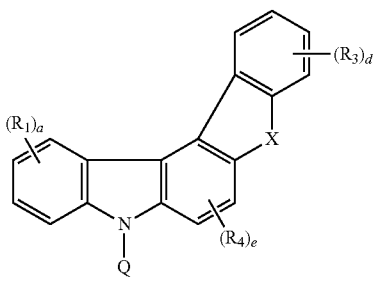

wherein $R_1$, $R_3$, $R_4$, a, d, e, X, and Q are as defined above;

6. The nitrogen-containing aromatic heterocyclic derivative according to item 2, which is represented by formula (5-1) or (5-2):

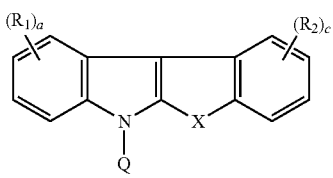

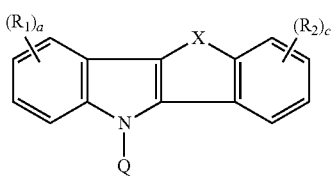

wherein $R_1$, $R_2$, a, c, X, and Q are as defined above;

7. The nitrogen-containing aromatic heterocyclic derivative according to any one of items 1 to 6, wherein $L_2$ represents a single bond;

8. The nitrogen-containing aromatic heterocyclic derivative according to any one of items 1 to 6, wherein $L_2$ represents a structure represented by any one of formulae (7a) to (7c):

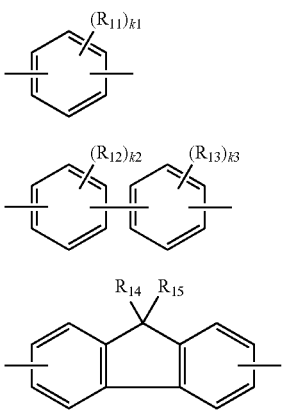

wherein:
each of $R_{11}$ to $R_{13}$ independently represents a linear or branched alkyl group having 1 to 15 carbon atoms, a cycloalkyl group having 3 to 15 ring carbon atoms, a substituted or unsubstituted silyl group, an aryl group having 6 to 20 ring carbon atoms, a heteroaryl group having 5 to 20 ring atoms, a halogen atom, or a cyano group, or adjacent two groups of $R_{11}$ to $R_{13}$ are bonded to each other to from a saturated or unsaturated divalent group which completes a ring;

each of $R_{14}$ and $R_{15}$ independently represents a linear or branched alkyl group having 1 to 15 carbon atoms, a cycloalkyl group having 3 to 15 ring carbon atoms, an aryl group having 6 to 20 ring carbon atoms, or a heteroaryl group having 5 to 20 ring atoms; and each of k1 to k3 independently represents an integer of 0 to 4;

9. The nitrogen-containing aromatic heterocyclic derivative according to any one of items 1 to 8, wherein X represents $NR_5$;

10. The nitrogen-containing aromatic heterocyclic derivative according to any one of items 1 to 8, wherein X represents an oxygen atom;

11. The nitrogen-containing aromatic heterocyclic derivative according to any one of items 1 to 8, wherein X represents a sulfur atom;

12. The nitrogen-containing aromatic heterocyclic derivative according to any one of items 1 to 8, wherein X represents $CR_6R_7$;

13. The nitrogen-containing aromatic heterocyclic derivative according to any one of items 1 to 8, wherein X represents $SiR_6R_7$;

14. The nitrogen-containing aromatic heterocyclic derivative according to any one of items 1 to 13, wherein Y represents an oxygen atom;

15. The nitrogen-containing aromatic heterocyclic derivative according to any one of items 1 to 13, wherein Y represents a sulfur atom;

16. The nitrogen-containing aromatic heterocyclic derivative according to any one of items 1 to 15, wherein $L_2$ is bonded to a carbon atom at 4-position of the structure represented by formula (1c);

17. The nitrogen-containing aromatic heterocyclic derivative according to any one of items 1 to 16, which is for use as a material for organic electroluminescence device;

18. The nitrogen-containing aromatic heterocyclic derivative according to any one of items 1 to 16, which is for use as a hole transporting material for organic electroluminescence device;

19. An organic electroluminescence device comprising organic thin film layers between an anode and a cathode, wherein the organic thin film layers comprise a light emitting layer and at least one layer of the organic thin film layers comprises the nitrogen-containing aromatic heterocyclic derivative according to any one of items 1 to 16;

20. The organic electroluminescence device according to item 19, wherein the organic thin film layers comprise a hole transporting layer and the hole transporting layer comprises the nitrogen-containing aromatic heterocyclic derivative;

21. The organic electroluminescence device according to item 19 or 20, wherein the light emitting layer comprises a phosphorescent material;

22. The organic electroluminescence device according to item 21, wherein the phosphorescent material is an ortho metallated complex of a metal selected from iridium (Ir), osmium (Os) and platinum (Pt); and 23. The organic electroluminescence device according to any one of items 20 to 22, wherein the hole transporting layer is made in contact with a layer comprising a compound represented by formula (A):

(A)

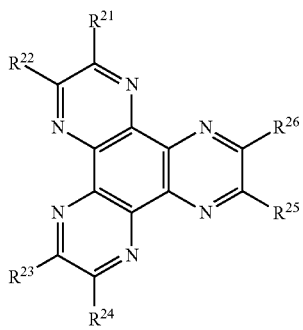

wherein:

$R^{21}$ to $R^{26}$ may be the same or different and each independently represent a cyano group, —$CONH_2$, a carboxyl group, or —$COOR^{27}$, wherein $R^{27}$ represents an alkyl group having 1 to 20 carbon atoms or a cycloalkyl group having 3 to 20 carbon atoms; and one or more of a pair of $R^{21}$ and $R^{22}$, a pair of $R^{23}$ and $R^{24}$, and a pair of $R^{25}$ and $R^{26}$ may be bonded to each other to form a group represented by —CO—O—CO—.

Effect of the Invention

According to the present invention, a long-lifetime organic EL device with a high emission efficiency and an organic EL material which realizes such a device are provided.

BRIEF DESCRIPTION OF DRAWINGS

FIG. 1 is a schematic cross-sectional view of an exemplified organic EL device of the invention.

MODE FOR CARRYING OUT THE INVENTION

The carbon number of a to b in the expression of "a substituted or unsubstituted X group having a to b carbon atoms" is the carbon number of the unsubstituted X group and does not include the carbon atom of the optional substituent.

The definition of hydrogen atom includes isotopes different in the neutron numbers, i.e., light hydrogen (protium), heavy hydrogen (deuterium), and tritium.

Nitrogen-Containing Aromatic Heterocyclic Derivative

The nitrogen-containing aromatic heterocyclic derivative of the invention is represented by formula (1-1) or (1-2):

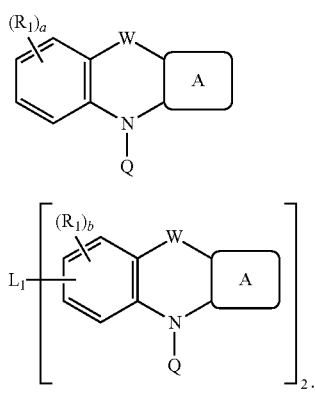

In formula (1-1) or (1-2):

a ring A is represented by formula (1a) or (1b):

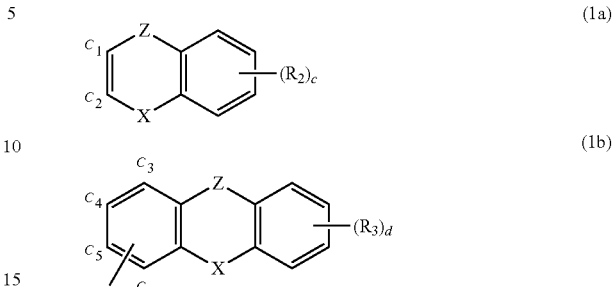

wherein ring carbon atoms $C_1$ and $C_2$, $C_3$ and $C_4$, $C_4$ and $C_5$, or $C_5$ and $C_6$ are shared with an adjacent ring.

X represents $NR_5$, $CR_6R_7$, $SiR_6R_7$, an oxygen atom, or a sulfur atom.

Each of W and Z independently represents a single bond, $CR_6R_7$, $SiR_6R_7$, an oxygen atom, or a sulfur atom.

$L_1$ represents a single bond, an arylene group having 6 to 30, preferably 6 to 18 ring carbon atoms, or a heteroarylene group having 5 to 30, preferably 5 to 18 ring atoms.

Each of $R_1$ to $R_7$ independently represents a linear or branched alkyl group having 1 to 15, preferably 1 to 5 carbon atoms, a cycloalkyl group having 3 to 15, preferably 5 to 12 ring carbon atoms, a substituted or unsubstituted silyl group, an aryl group having 6 to 30, preferably 6 to 18 ring carbon atoms, a heteroaryl group having 5 to 30, preferably 5 to 18 ring atoms, a halogen atom, or a cyano group, or adjacent two groups of $R_1$ to $R_7$ are bonded to each other to from a saturated or unsaturated divalent group which completes a ring.

Each of the subscript a, c and d independently represents an integer of 0 to 4, preferably 0 to 2.

The subscript b represents an integer of 0 to 3, preferably 0 to 2.

The subscript e represents an integer of 0 to 2, preferably 0 or 1.

Q represents a structure represented by formula (1c):

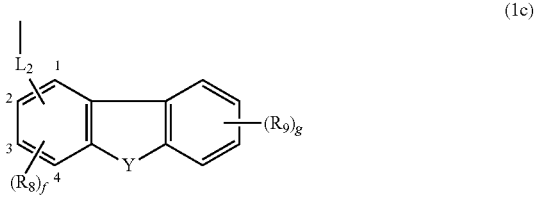

In formula (1-c):

Y represents an oxygen atom or a sulfur atom.

$L_2$ represents a single bond, an arylene group having 6 to 30, preferably 6 to 18 ring carbon atoms, or a heteroarylene group having 5 to 30, preferably 5 to 18 ring atoms, provided that when $L_2$ is bonded to a carbon atom at 2-position of the structure represented by formula (1c), $L_2$ represents an arylene group having 6 to 30, preferably 6 to 18 ring carbon atoms or a heteroaryl group having 5 to 30, preferably 5 to 18 ring atoms.

Each of $R_8$ and $R_9$ independently represents a linear or branched alkyl group having 1 to 15, preferably 1 to 5 carbon atoms, a cycloalkyl group having 3 to 15, preferably 5 to 12 ring carbon atoms, a substituted or unsubstituted silyl group, an aryl group having 6 to 30, preferably 6 to 18 ring carbon atoms, a heteroaryl group having 5 to 30, preferably 5 to 18 ring atoms, a halogen atom, or a cyano group, or adjacent two groups of $R_8$ and $R_9$ are bonded to each other to from a saturated or unsaturated divalent group which completes a ring.

The subscript f represents an integer of 0 to 3, preferably 0 to 2.

The subscript g represents an integer of 0 to 4, preferably 0 to 2.

Examples of the arylene group for $L_1$ and $L_2$ include divalent residues of aromatic compounds selected from benzene, naphthalene, phenanthrene, biphenyl, terphenyl (inclusive of isomers), quaterphenyl (inclusive of isomers), fluoranthene, triphenylene, 9,9-dimethylfluorene, benzo[c]phenanthrene, benzo[a]triphenylene, naphtho[1,2-c]phenanthrene, naphtho[1,2-a]triphenylene, dibenzo[a,c]triphenylene, and benzo[b]fluoranthene, with a 1,4-phenylene group, a 1,3-phenylene group, a naphthalene-2,6-diyl group, a naphthalene-2,7-diyl group, and a 9,9-dimethylfluorene-2,7-diyl group being preferred.

Examples of the alkyl group for $R_1$ to $R_9$ include a methyl group, an ethyl group, a n-propyl group, an isopropyl group, a n-butyl group, a s-butyl group, an isobutyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group, with a methyl group, a t-butyl group, an ethyl group, a n-propyl group, and an isopropyl group being preferred.

Examples of the cycloalkyl group for $R_1$ to $R_9$ include a cyclopropyl group, a cyclobutyl group, a cyclopentyl group, a cyclohexyl group, and a cyclooctyl group, with a cyclopentyl group and a cyclohexyl group being preferred.

Examples of the substituted silyl group for $R_1$ to $R_9$ include —$SiH_2R$, —$SiHR_2$, and —$SiR_3$, wherein R is selected from the alkyl groups mentioned above and two or three R groups may be the same or different, with a trimethylsilyl group, a triethylsilyl group, and a t-butyldimethylsilyl group being preferred.

Examples of the aryl group for $R_1$ to $R_9$ include a phenyl group, a naphthyl group, a phenanthryl group, a biphenyl group, a terphenyl group, a quaterphenyl group, a fluoranthenyl group, a triphenylenyl group, a 9,9-dimethylfluorenyl group, a benzo[c]phenanthrenyl group, a benzo[a]triphenylenyl group, a naphtho[1,2-c]phenanthrenyl group, a naphtho[1,2-a]triphenylenyl group, a dibenzo[a,c]triphenylenyl group, and a benzo[b]fluoranthenyl group, with a phenyl group, a 4-biphenyl group, a 3-biphenyl group, a 5'-m-terphenyl group, a 1-naphthyl group, a 9,9-dimethylfluorene-2-yl group, a 2-naphthyl group, and a 9-phenanthrenyl group being preferred.

The heteroaryl group for $R_1$ to $R_9$ preferably include at least one hetero atom selected from a nitrogen atom, an oxygen atom and a sulfur atom. Examples thereof include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a carbazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group, with a furyl group, a thienyl group, a benzofuranyl group, a benzothiophenyl group, a dibenzofuranyl group, and a dibenzothiophenyl group being preferred.

Examples of the divalent group formed by the adjacent groups of $R_1$ to $R_9$ which are boned to each other include a butane-1,4-diyl group and a 1,3-butadiene-1,4-diyl group.

Each of W and Z preferably represents a single bond.

$L_2$ preferably represents a single bond or a structure represented by any one of formulae (7a) to (7c):

(7a)

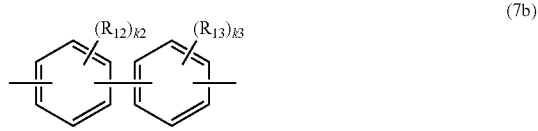

(7b)

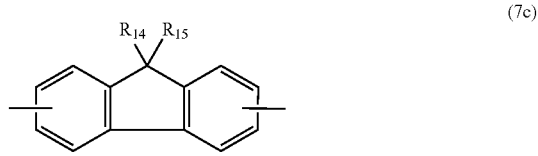

(7c)

wherein:

each of $R_{11}$ to $R_{13}$ independently represents a linear or branched alkyl group having 1 to 15 carbon atoms, a cycloalkyl group having 3 to 15 ring carbon atoms, a substituted or unsubstituted silyl group, an aryl group having 6 to 20 ring carbon atoms, a heteroaryl group having 5 to 20 ring atoms, a halogen atom, or a cyano group, or adjacent two groups of $R_{11}$ to $R_{13}$ are bonded to each other to from a saturated or unsaturated divalent group which completes a ring;

each of $R_{14}$ and $R_{15}$ independently represents a linear or branched alkyl group having 1 to 15 carbon atoms, a cycloalkyl group having 3 to 15 ring carbon atoms, an aryl group having 6 to 20 ring carbon atoms, or a heteroaryl group having 5 to 20 ring atoms; and each of k1 to k3 independently represents an integer of 0 to 4.

In formula (1c), $L_2$ is bonded preferably to the carbon atom at 4-position which is indicated in formula (1c).

The nitrogen-containing aromatic heterocyclic derivative of the invention is preferably represented by any one of formulae (2-1), (2-2), (3-1), (3-2), (4-1), (5-1), and (5-2), and particularly preferably by any one of formulae (2-1), (2-2), (3-2) and (5-2).

(2-1)
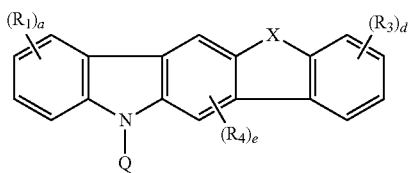

(2-2)
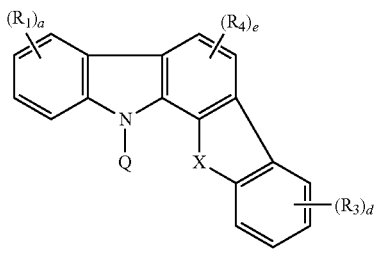

(3-1)
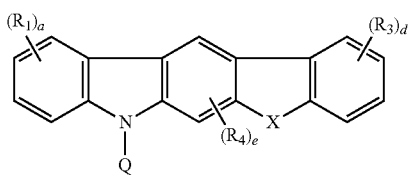

(3-2)
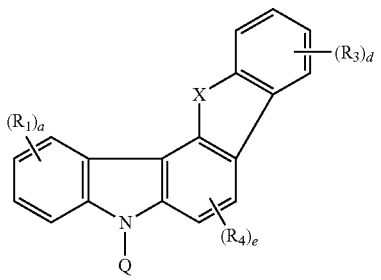

(4-1)
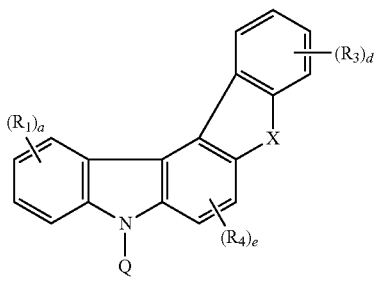

(5-1)
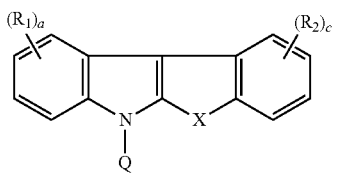

(5-2)
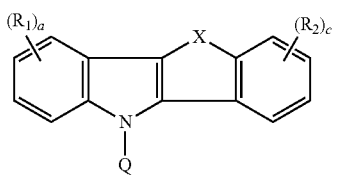

wherein $R_1$, $R_2$, $R_3$, $R_4$, a, b, c, d, e, X, and Q are as defined above.

Examples of the optional substituent when saying "substituted or unsubstituted" hereinbefore and hereinafter include a fluorine atom, a cyano group, an alkyl group having 1 to 20, preferably 1 to 5 carbon atoms, a cycloalkyl group having 3 to 20, preferably 5 to 12 carbon atoms, an alkoxy group having 1 to 20, preferably 1 to 5 carbon atoms, a haloalkyl group having 1 to 20, preferably 1 to 5 carbon atoms, a haloalkoxy group having 1 to 20, preferably 1 to 5 carbon atoms, an alkylsilyl group having 1 to 10, preferably 1 to 5 carbon atoms, an aryl group having 6 to 30, preferably 6 to 18 ring carbon atoms, an aryloxy group having 6 to 30, preferably 6 to 18 ring carbon atoms, an arylsilyl group having 6 to 30, preferably 6 to 18 carbon atoms, an aralkyl group having 7 to 30, preferably 7 to 20 carbon atoms, and a heteroaryl group having 5 to 30, preferably 5 to 18 ring atoms.

Examples of the nitrogen-containing aromatic heterocyclic derivative are shown below, although not limited to the following compounds.

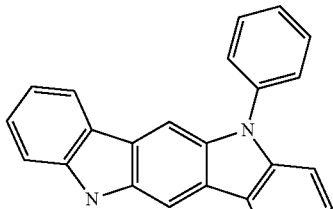

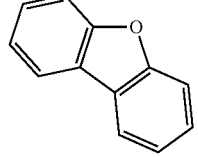

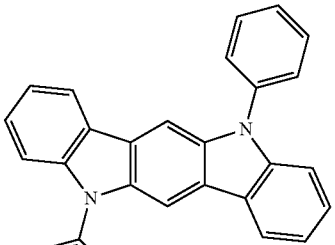

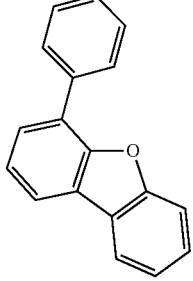

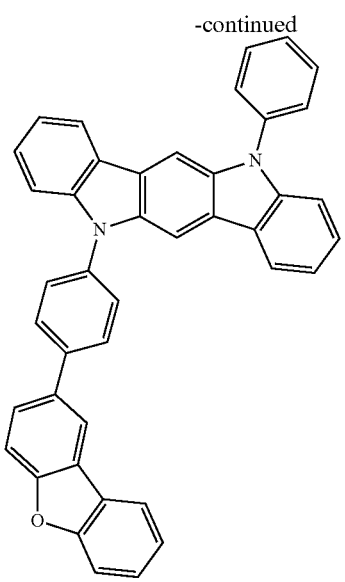
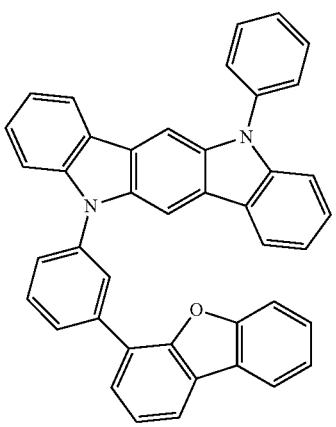
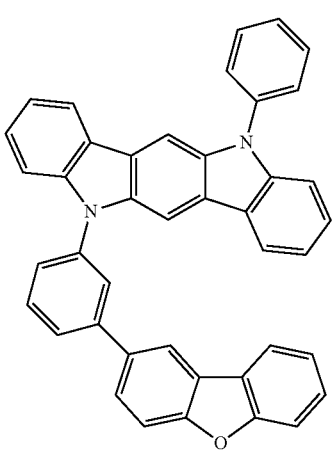
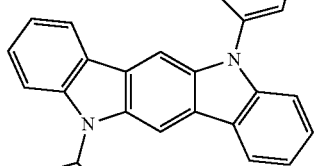
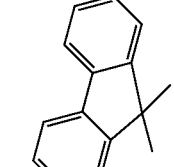
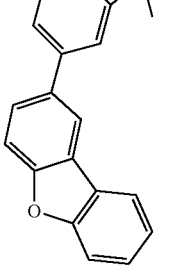
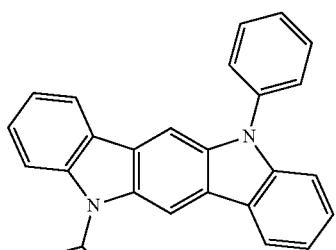

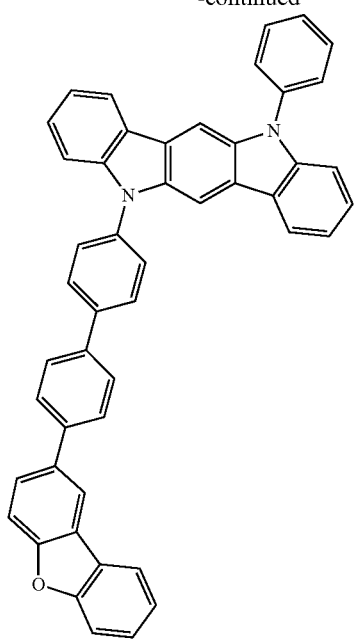
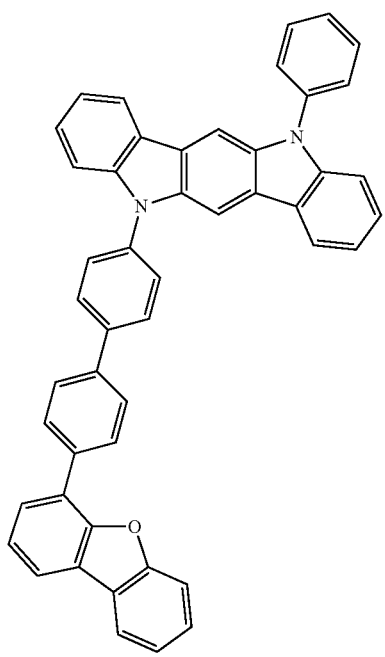
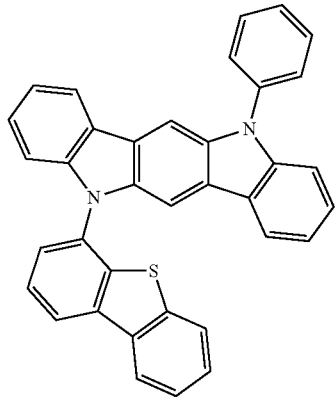
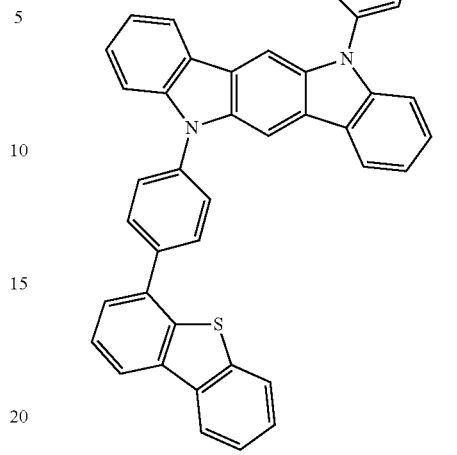
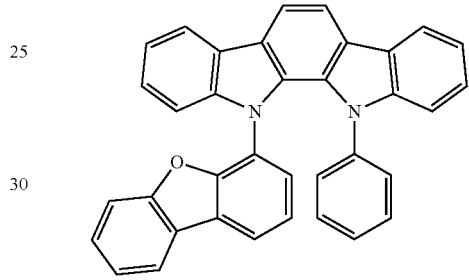
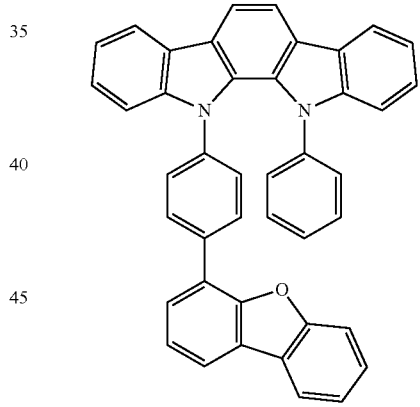
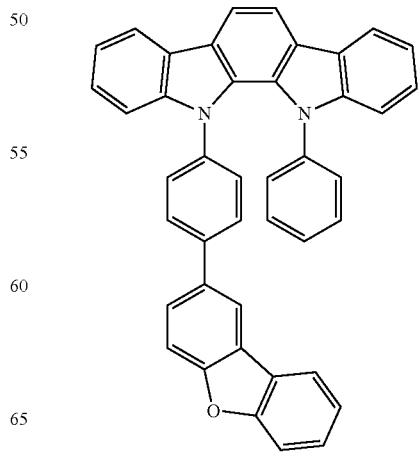

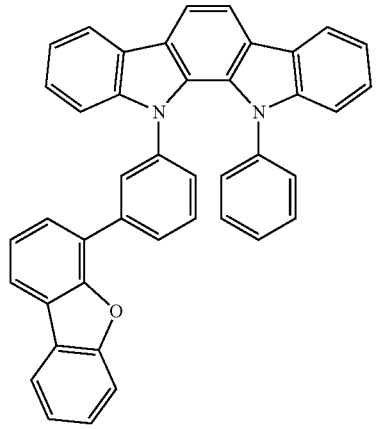
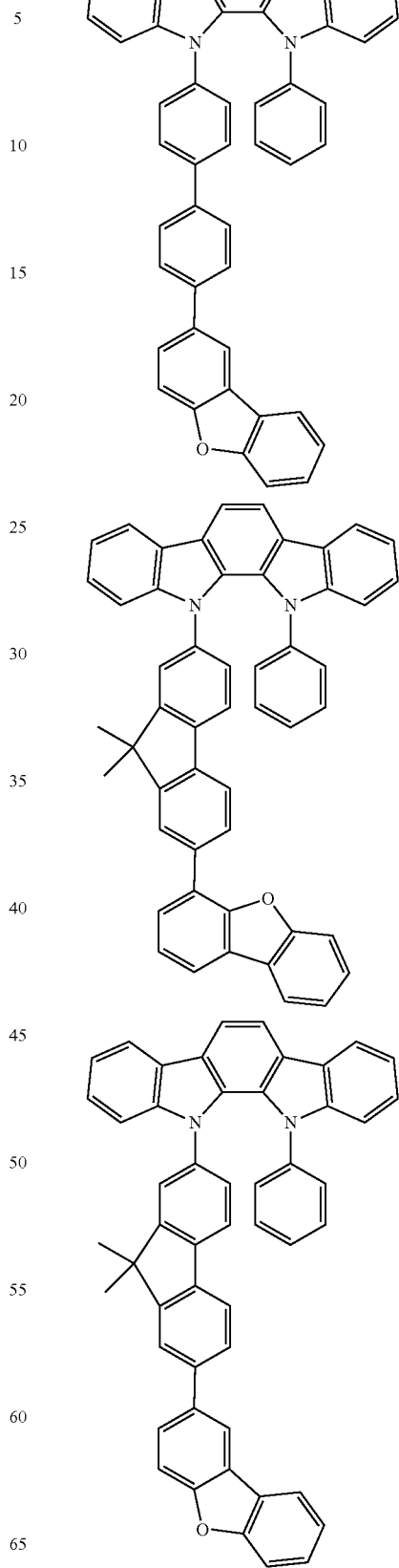

-continued
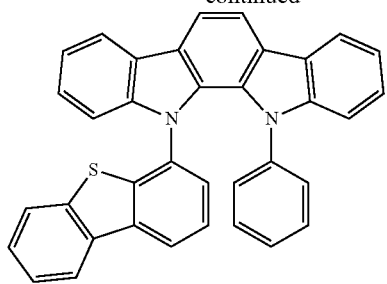
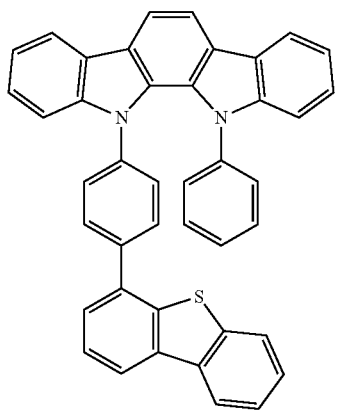
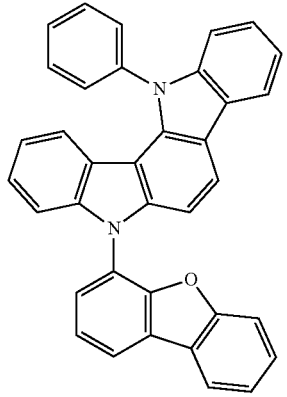
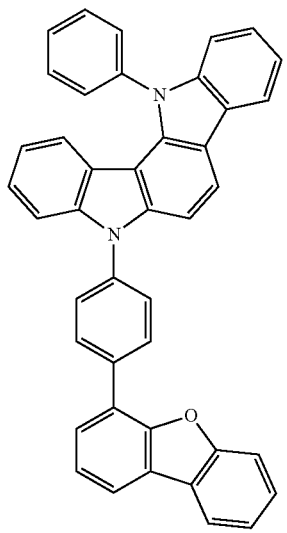
-continued
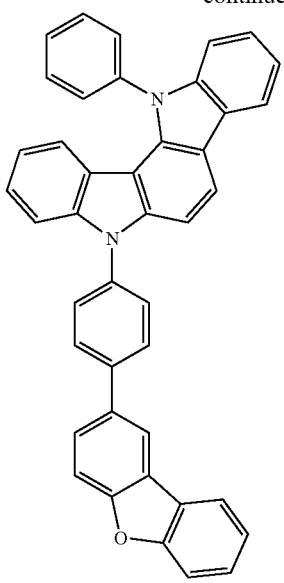
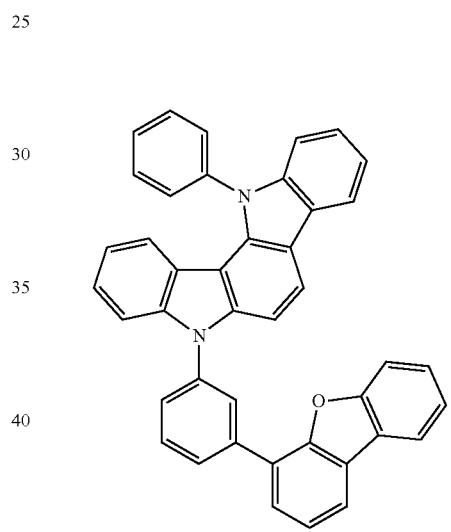
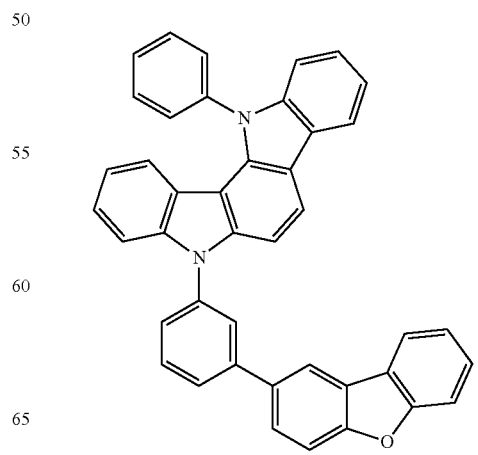

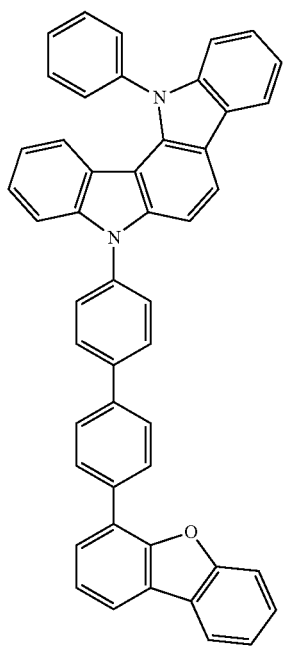
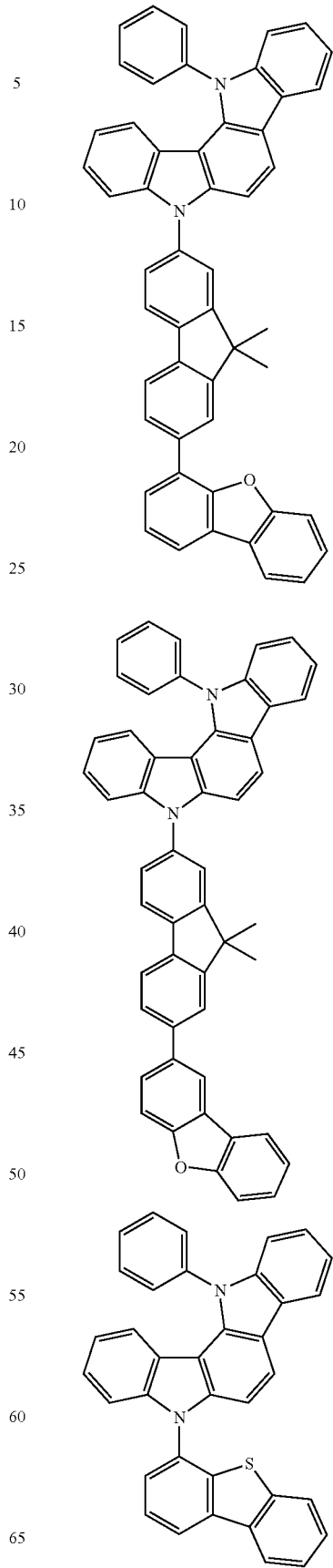
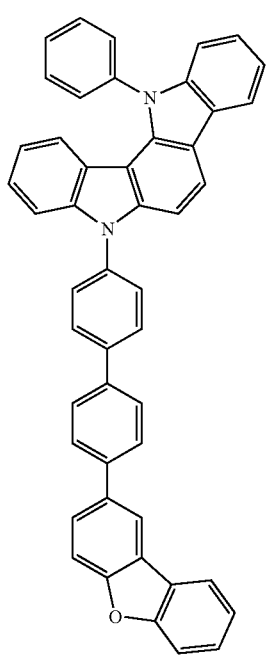

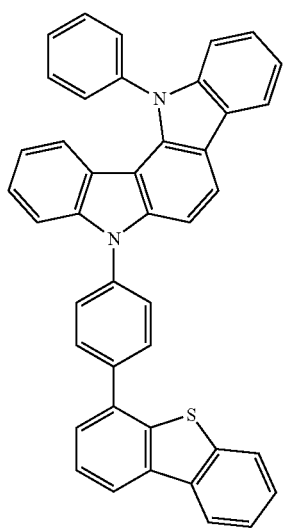
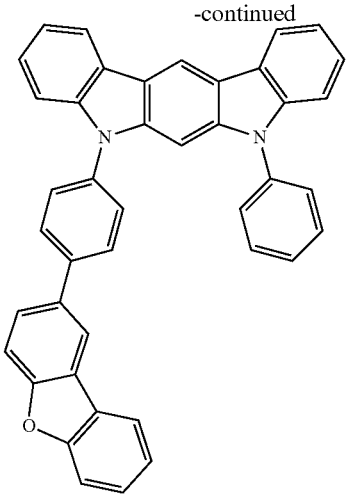
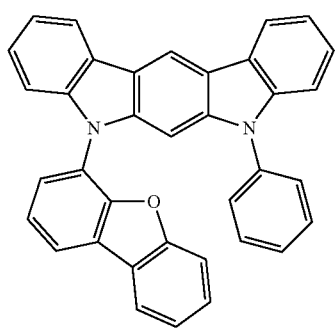
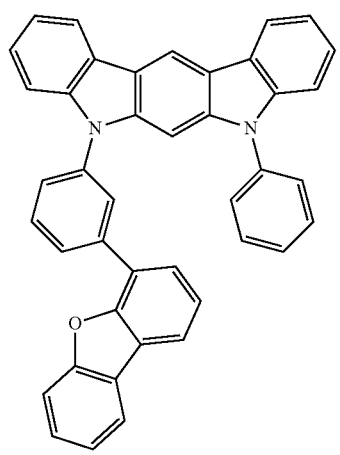
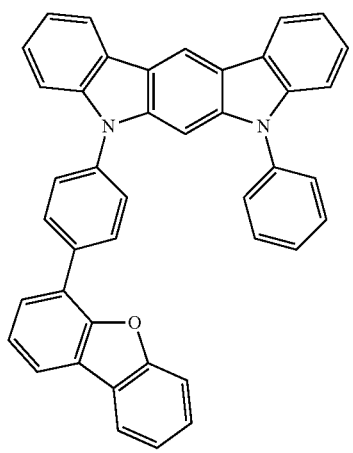
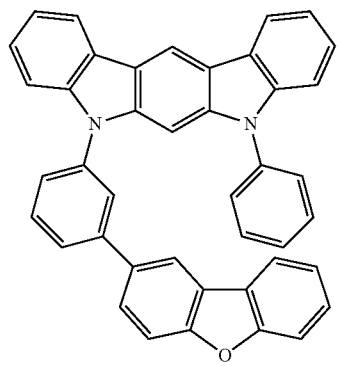

25
-continued
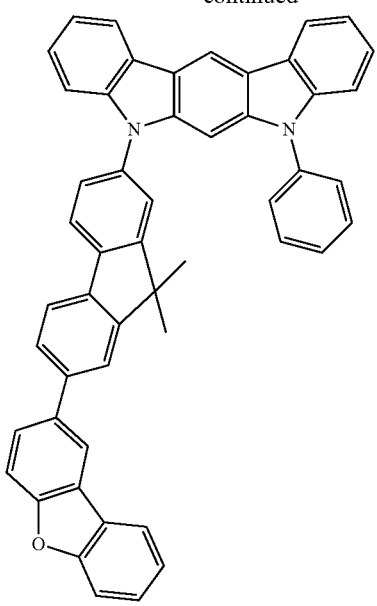
26
-continued
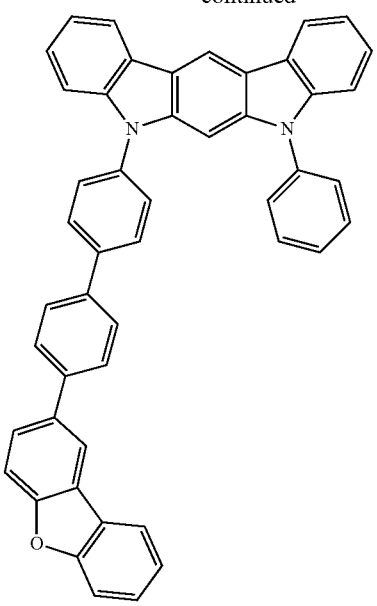
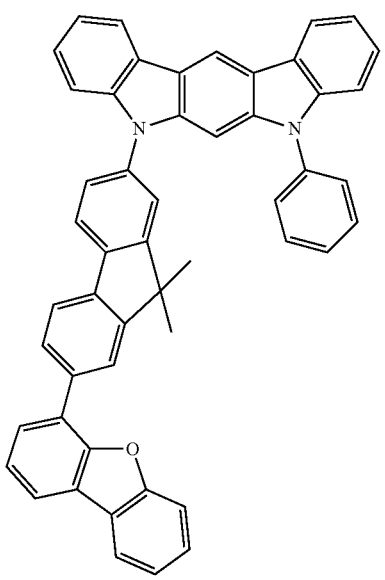
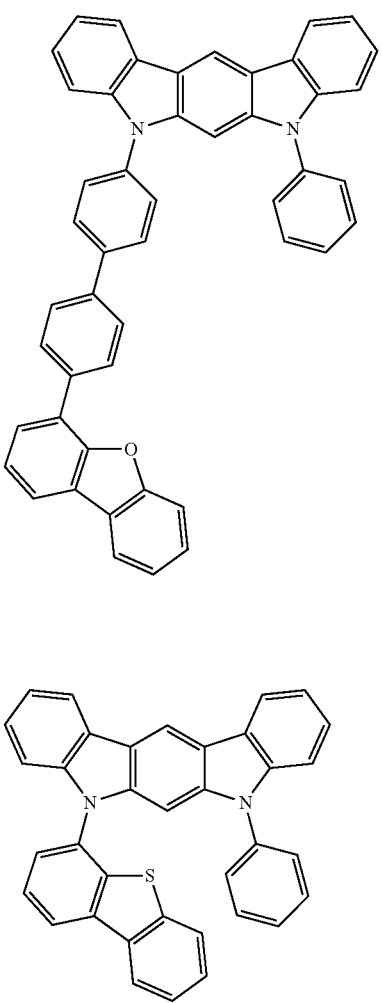

27
-continued
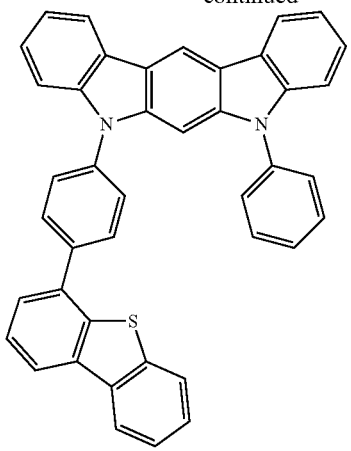
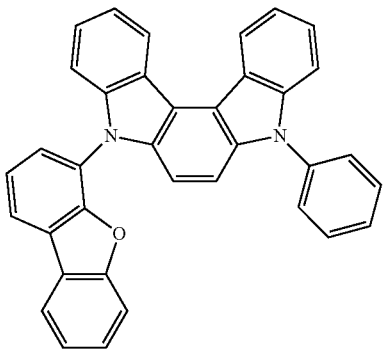
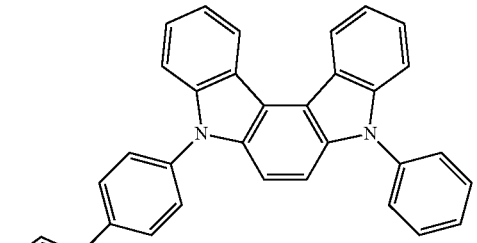
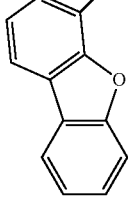
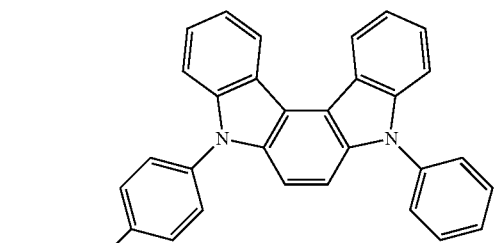
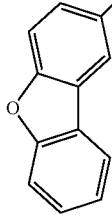
28
-continued
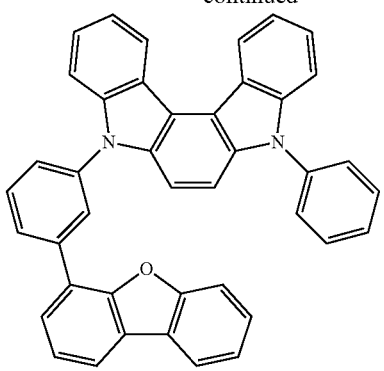
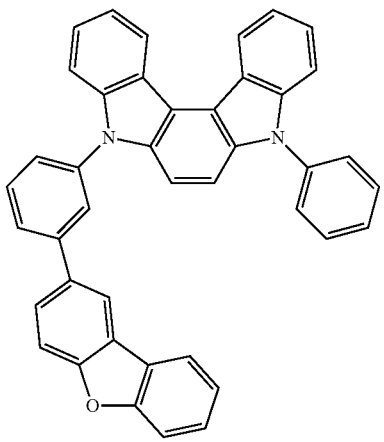
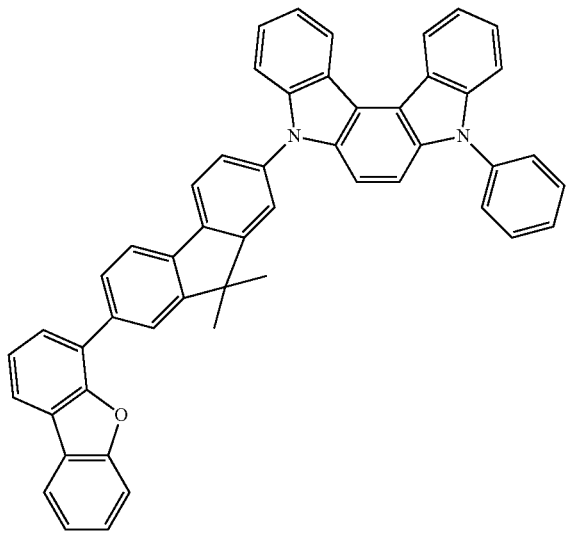

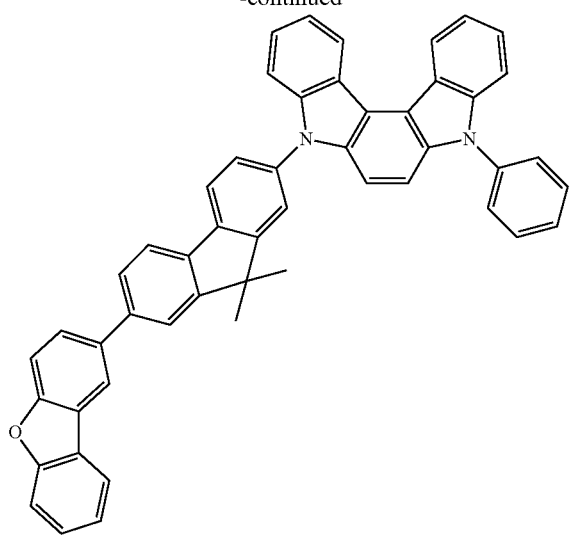
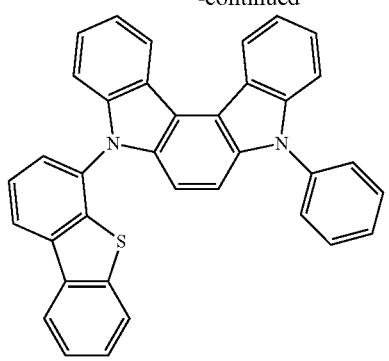
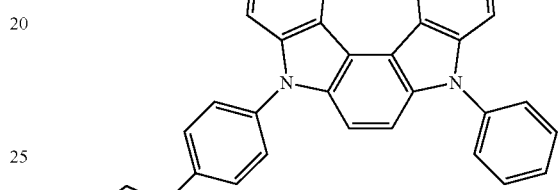
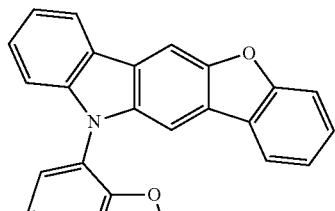
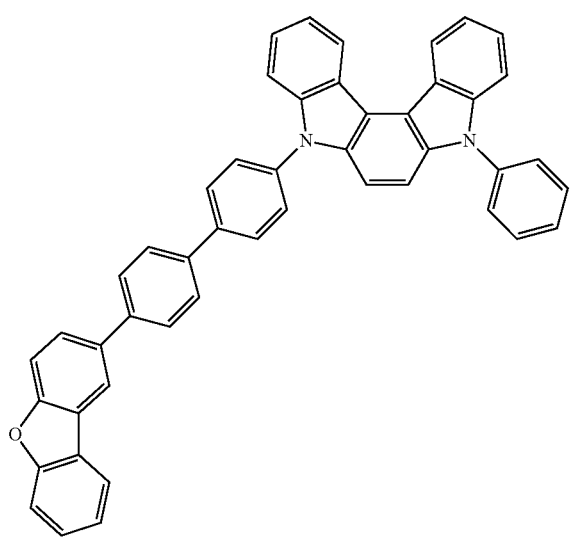
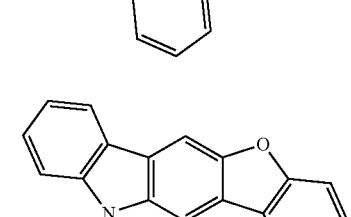
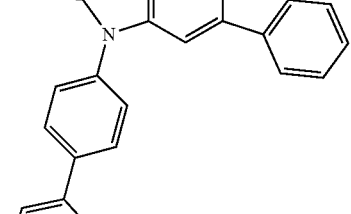

31
-continued
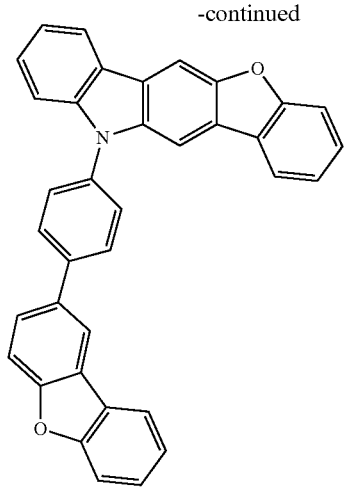
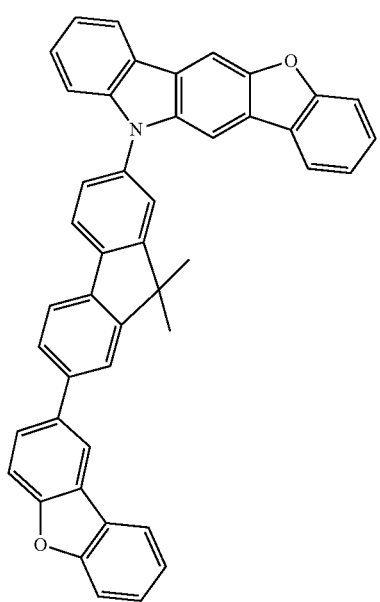
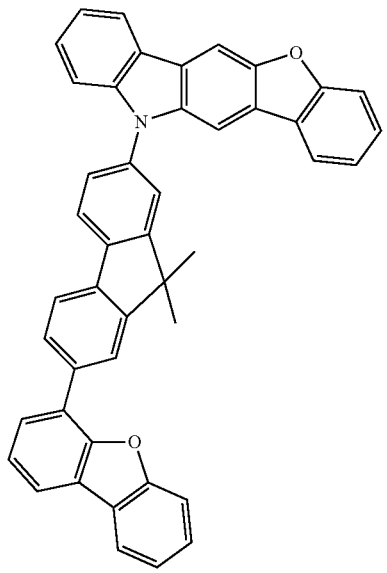
32
-continued
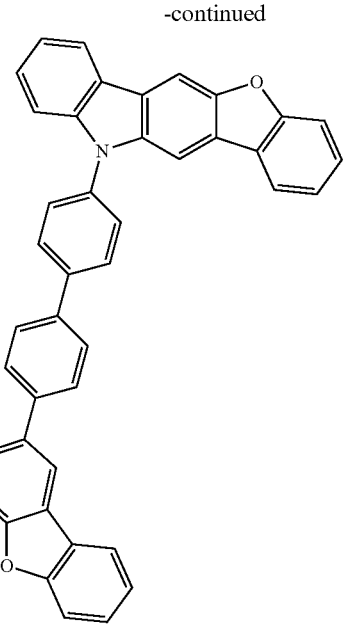
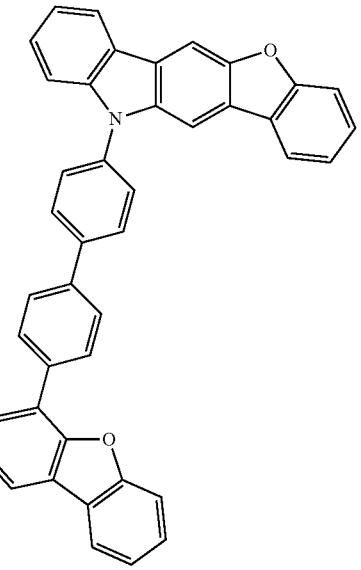

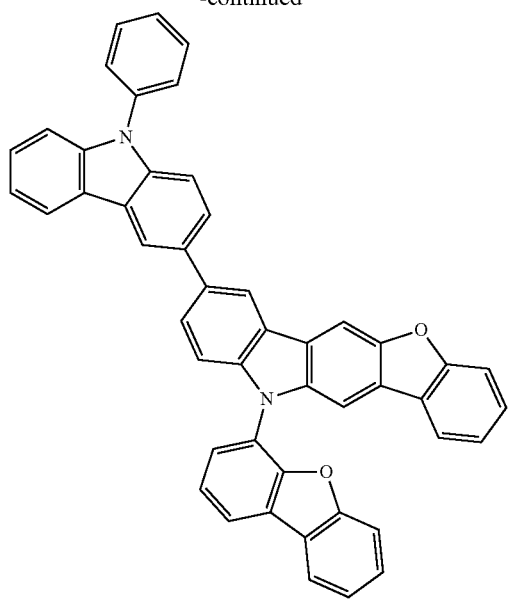
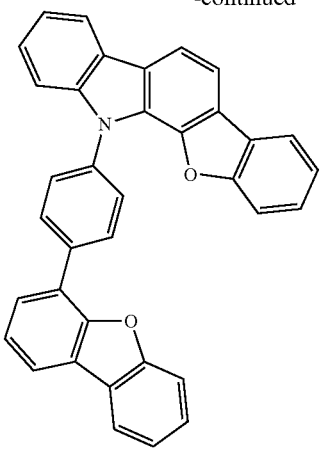
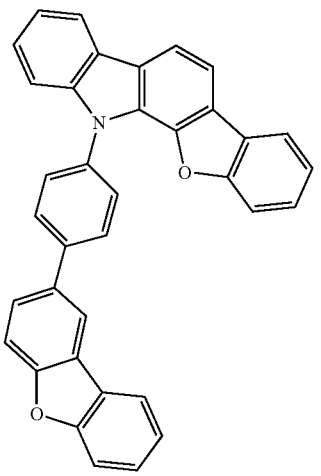
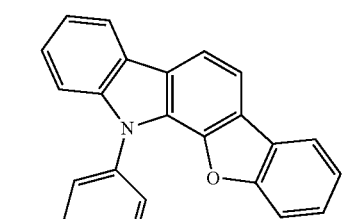
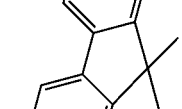
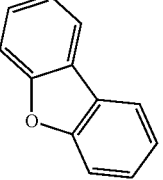

35
-continued
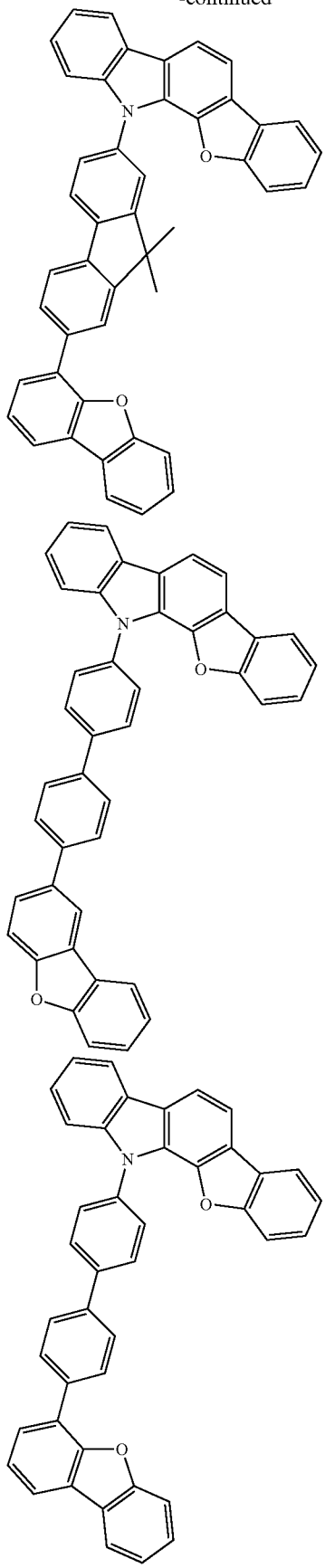
36
-continued
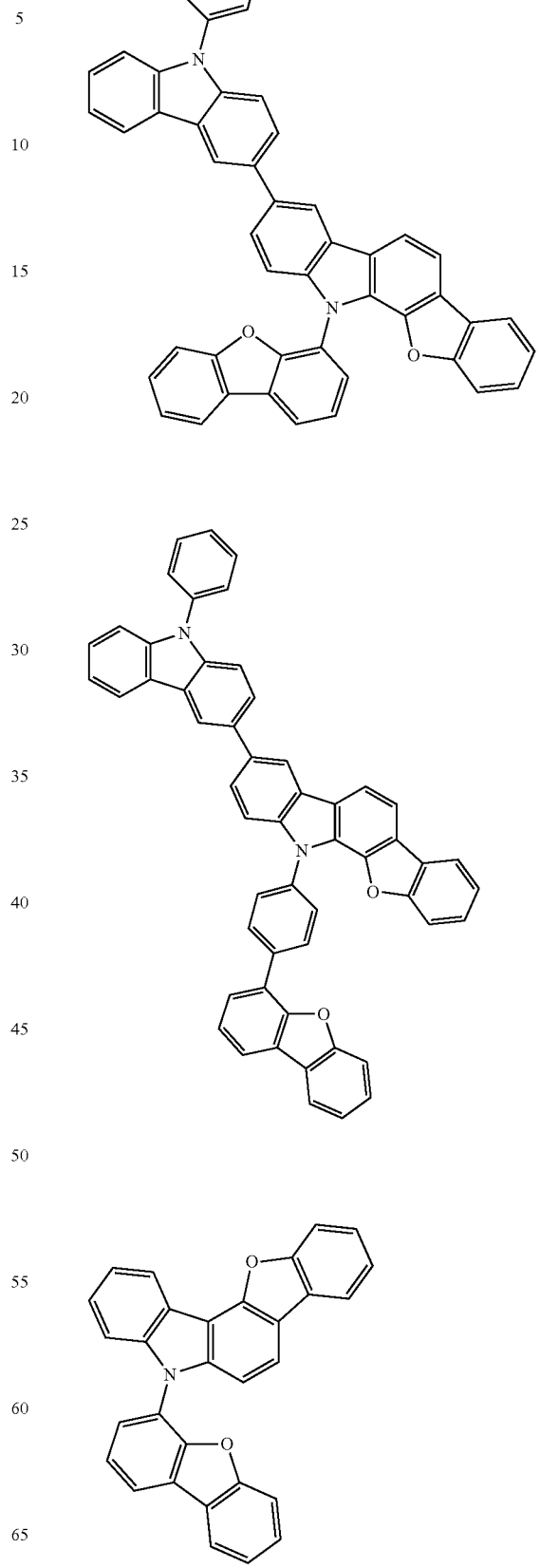

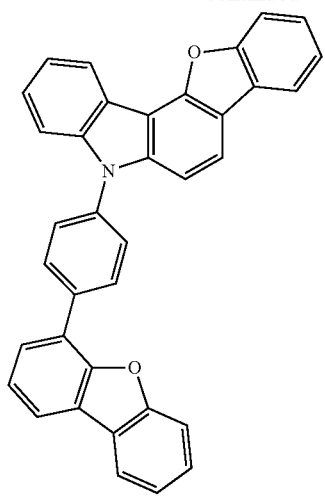
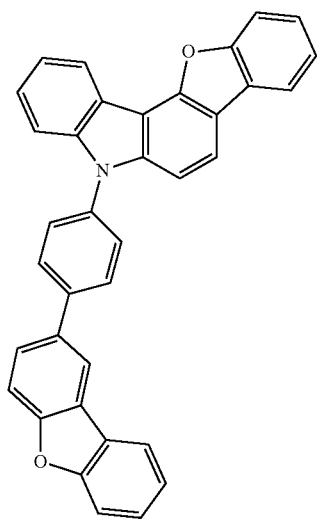
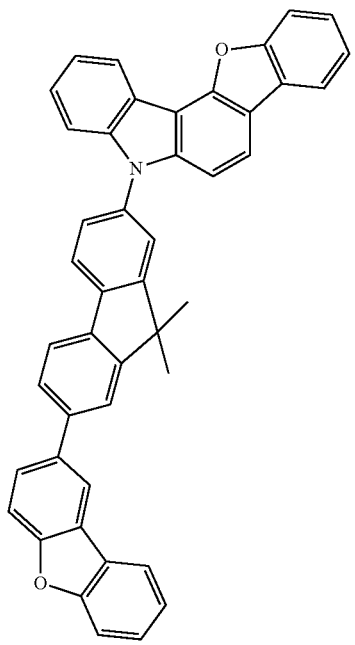
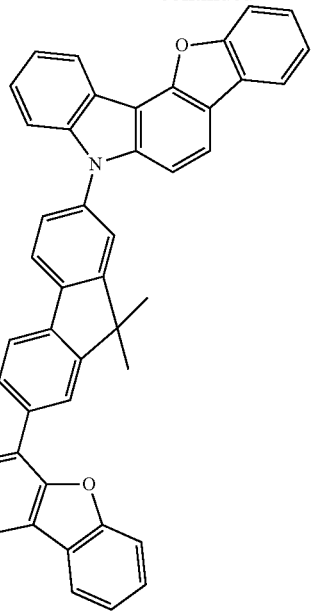
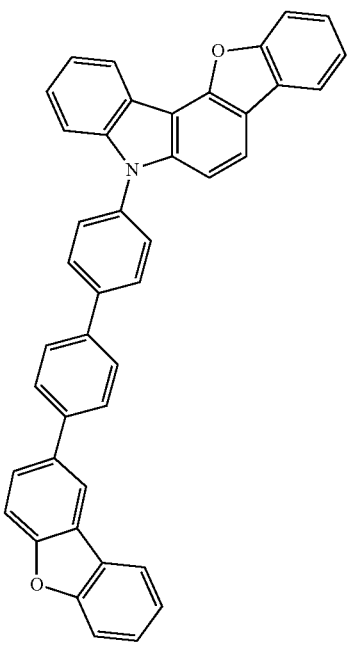

-continued
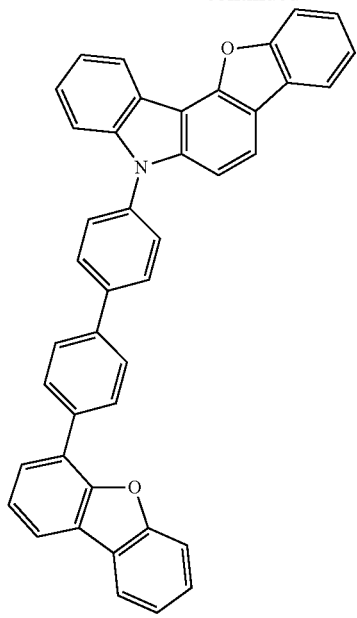
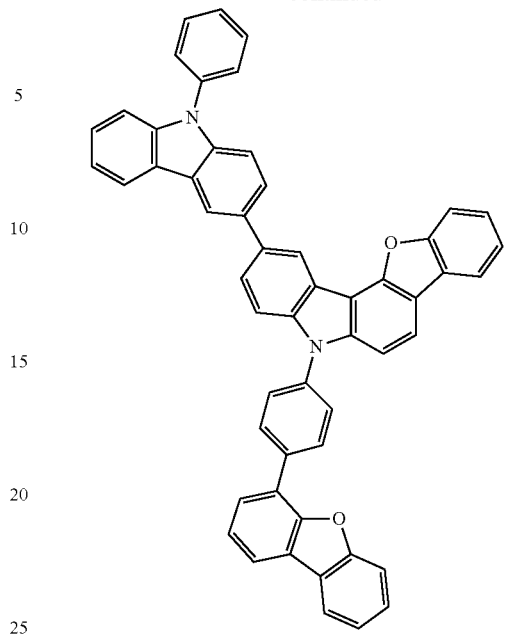
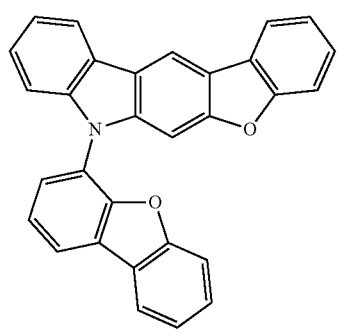
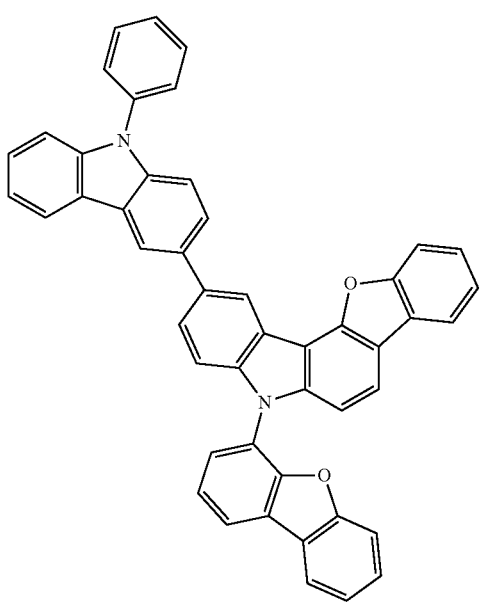
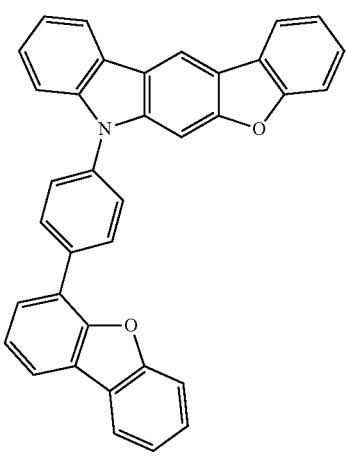

41
-continued
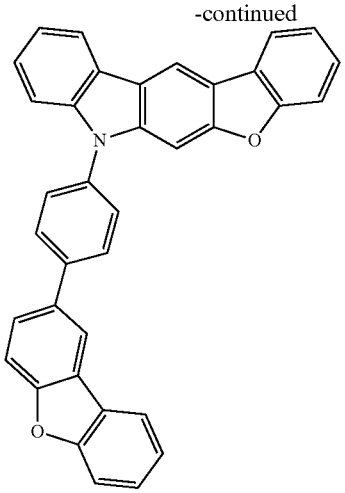
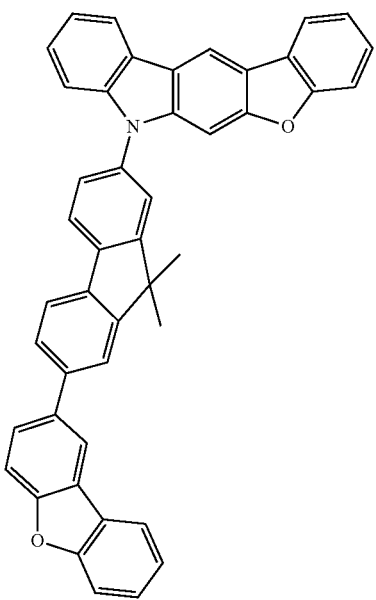
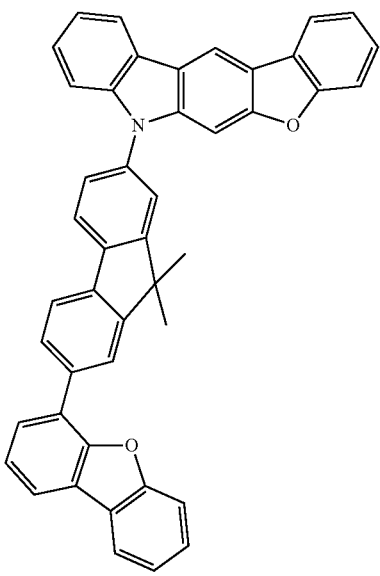
42
-continued
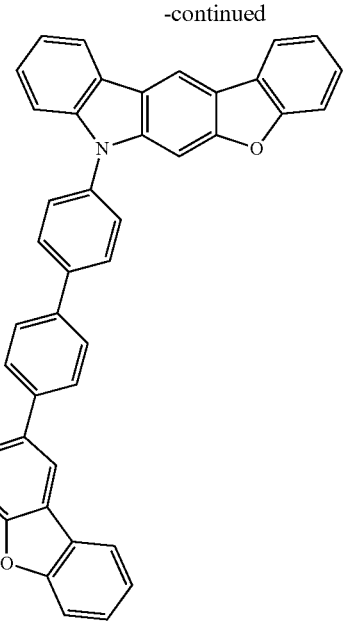
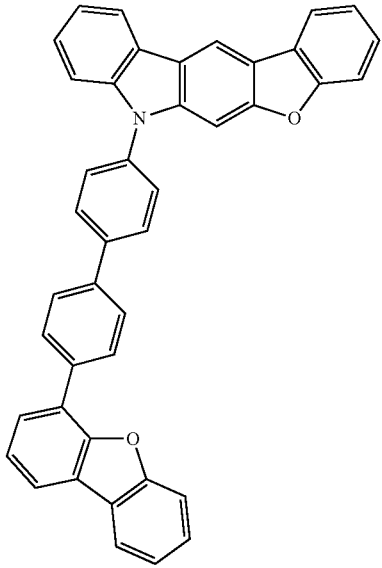

43
-continued
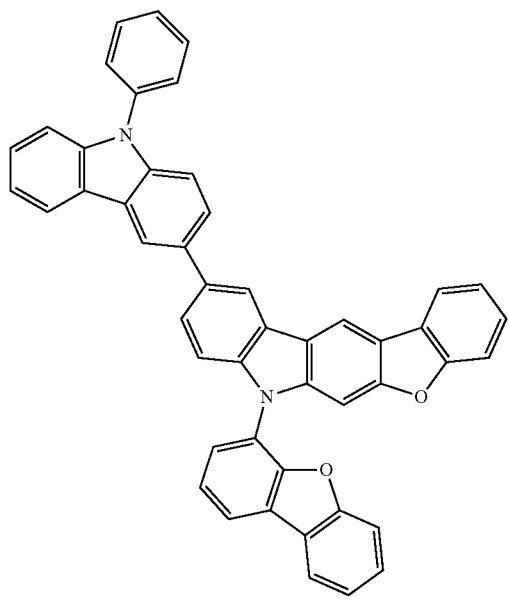
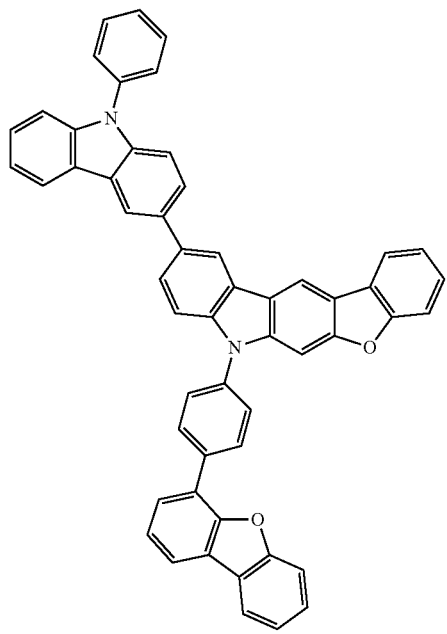
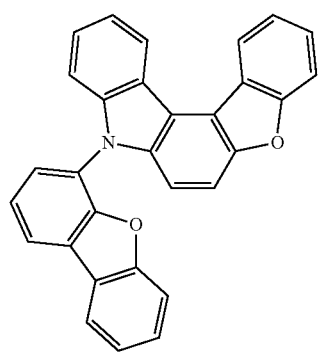
44
-continued
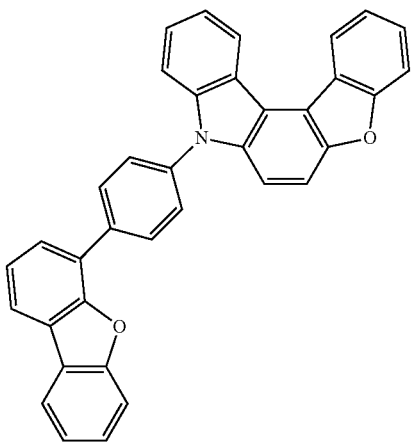
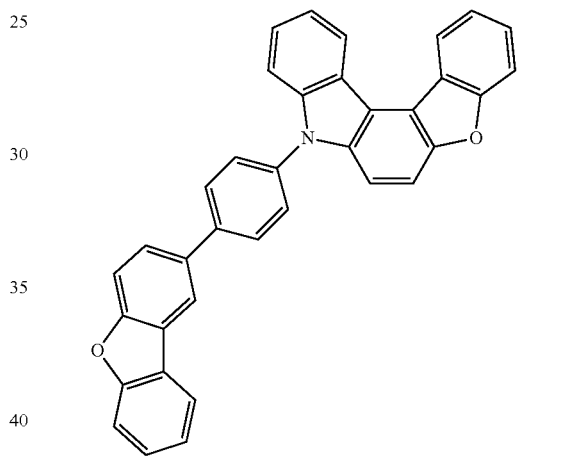
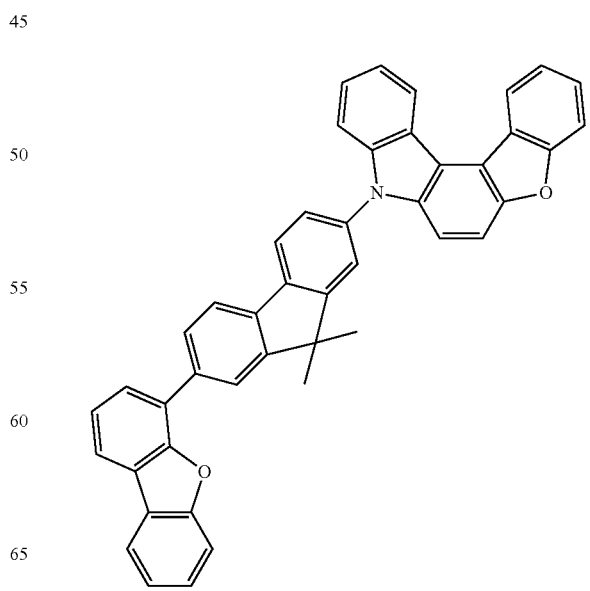

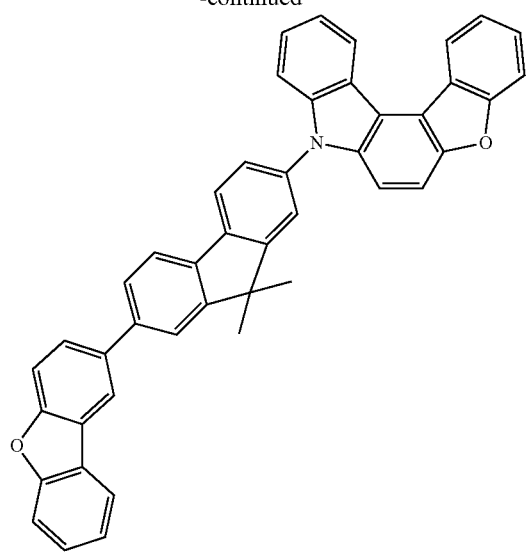
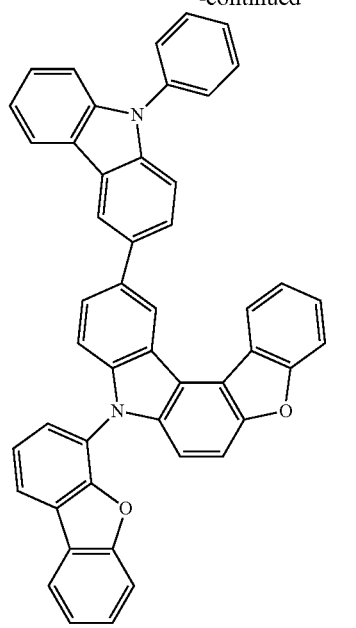
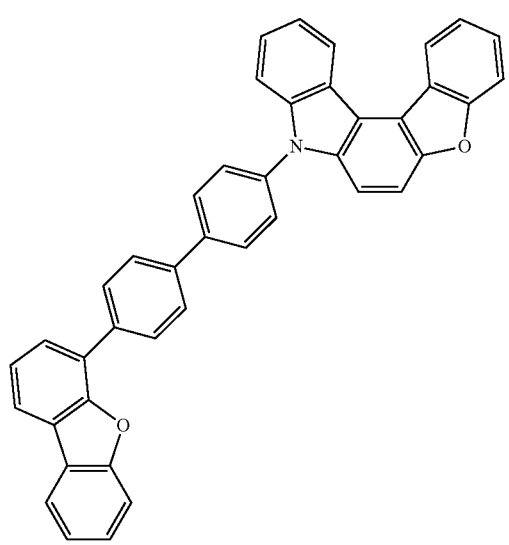
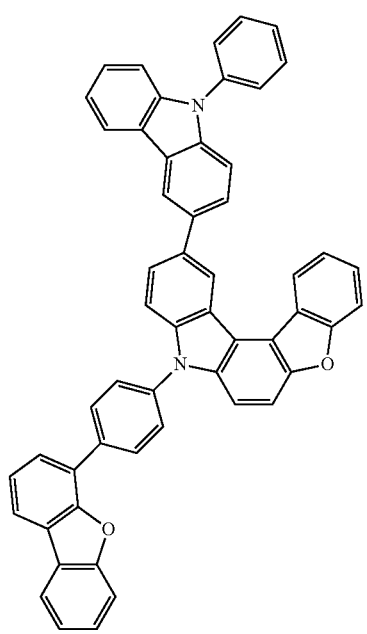
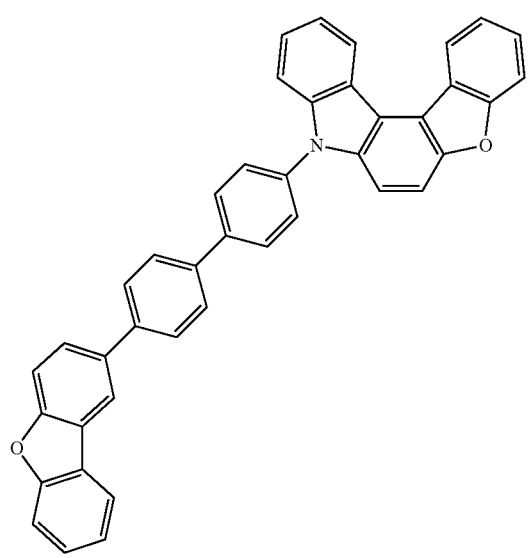
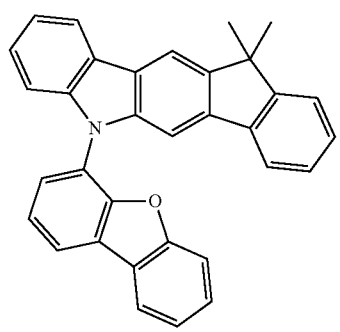

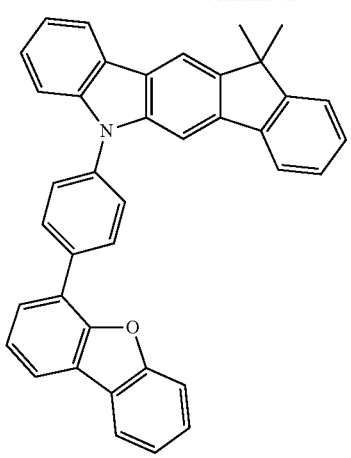
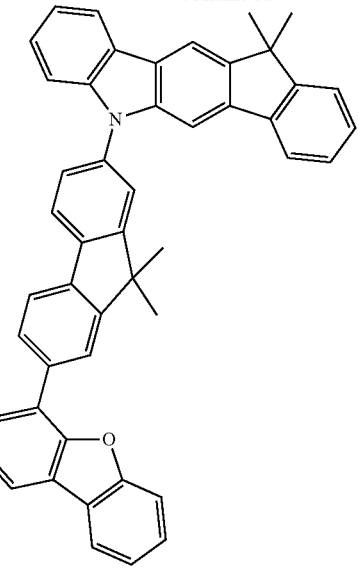
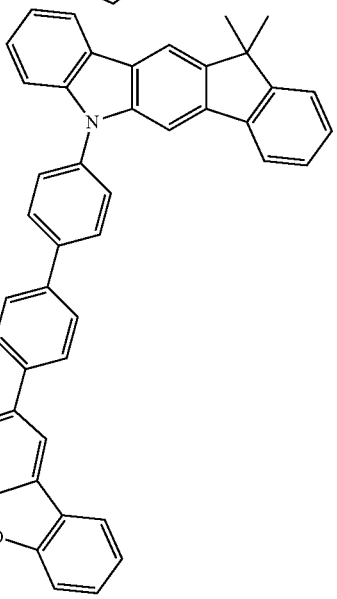
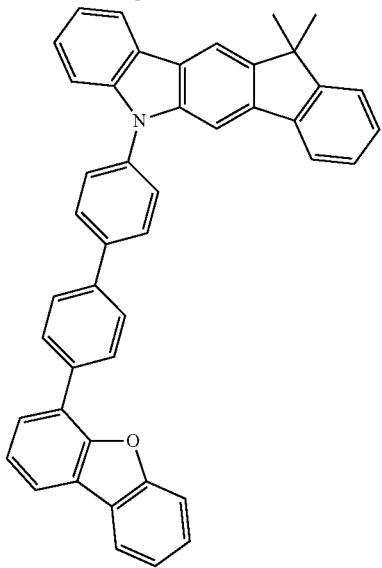

49
-continued
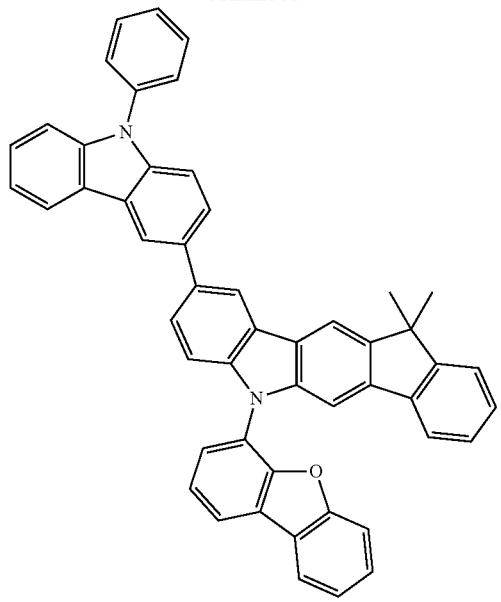
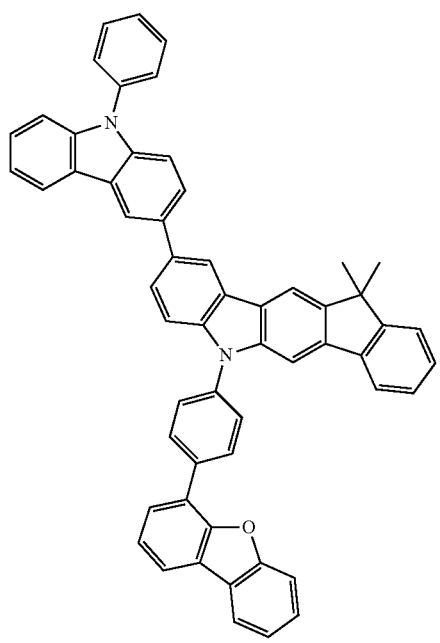
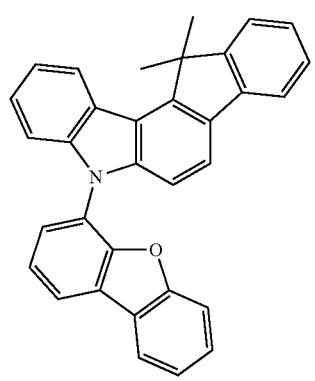
50
-continued
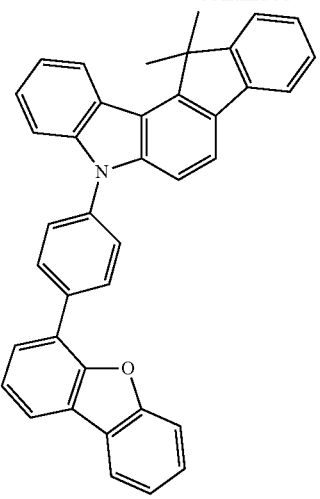

51
-continued
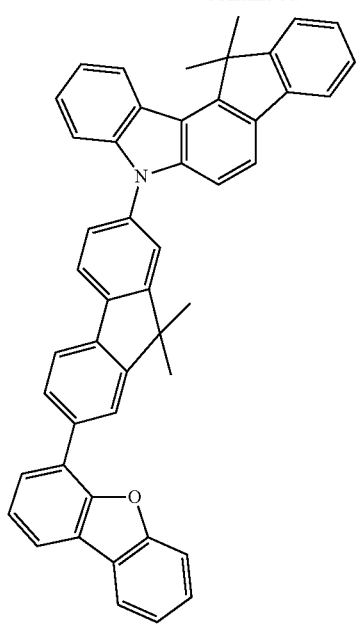
52
-continued
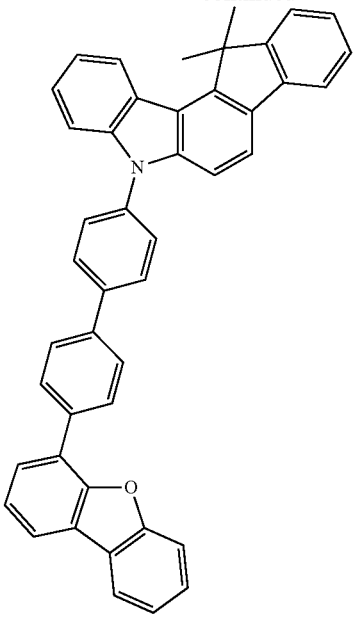
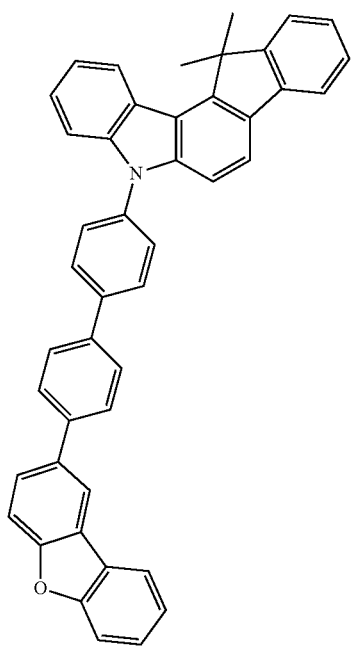
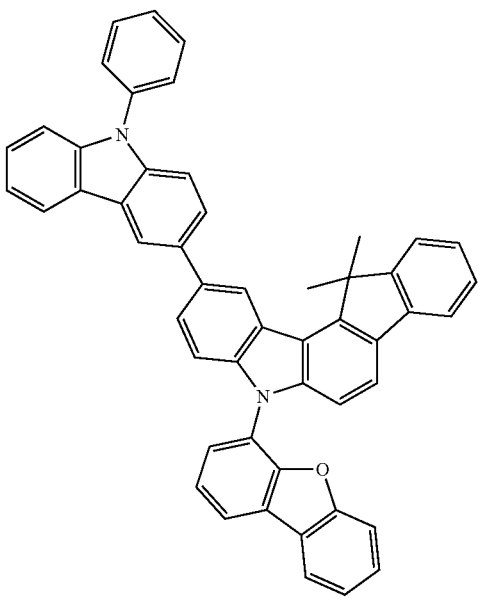

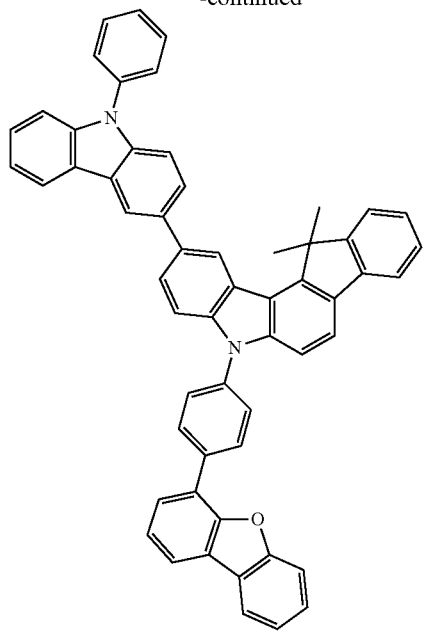
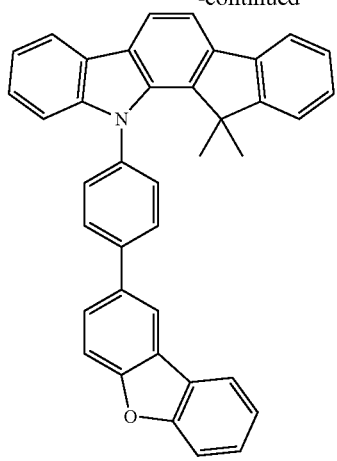
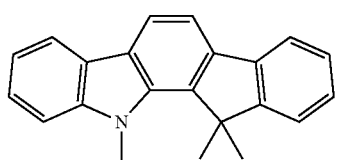
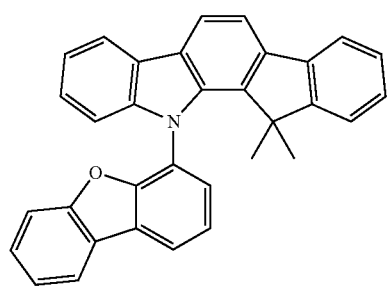
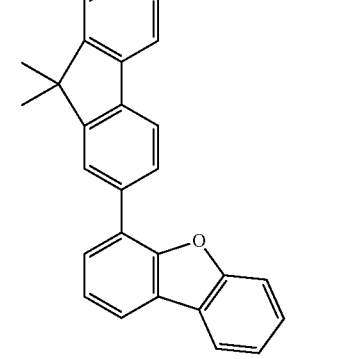
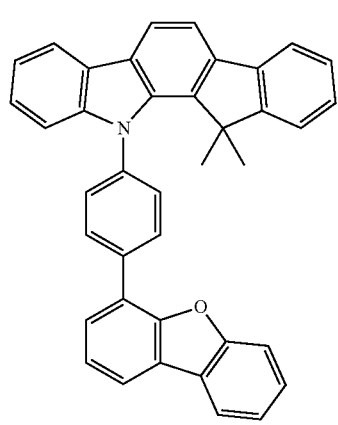
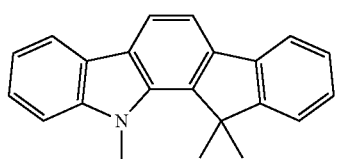
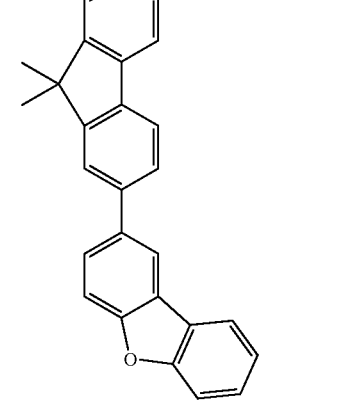

-continued
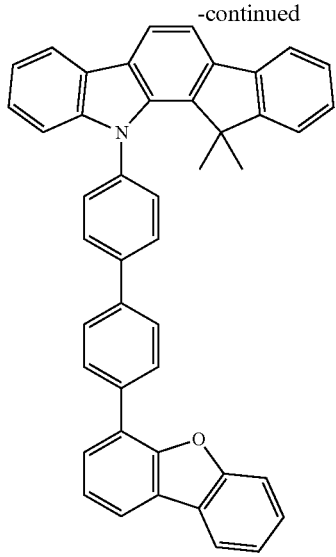
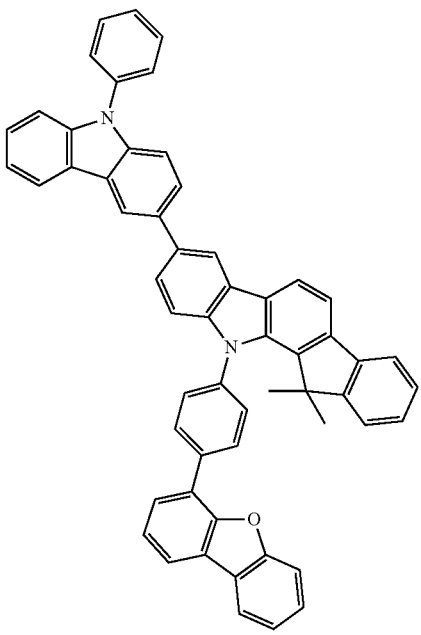
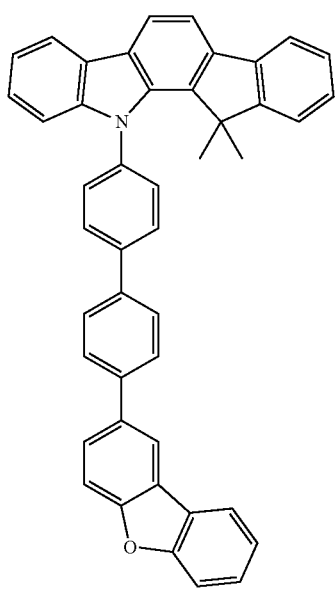
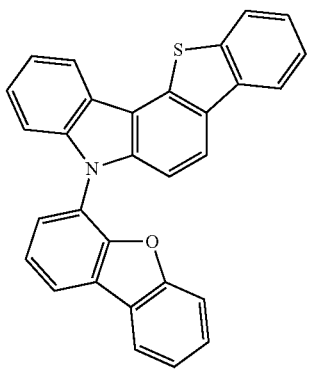
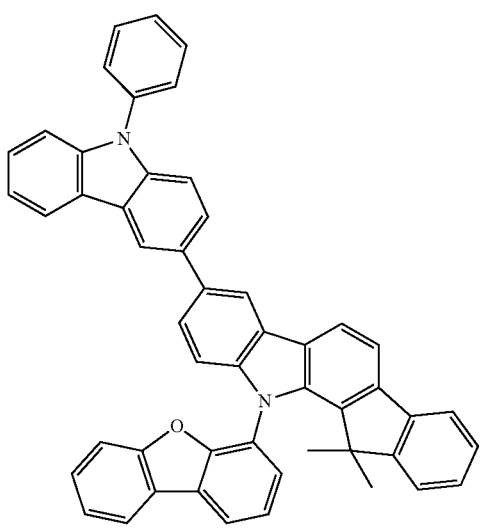
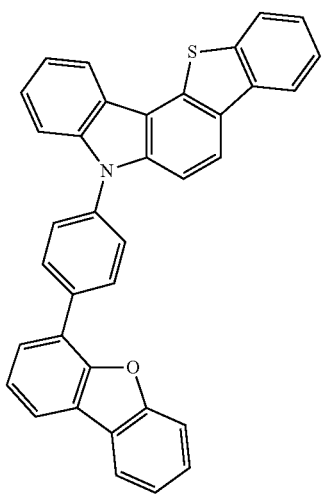

57
-continued
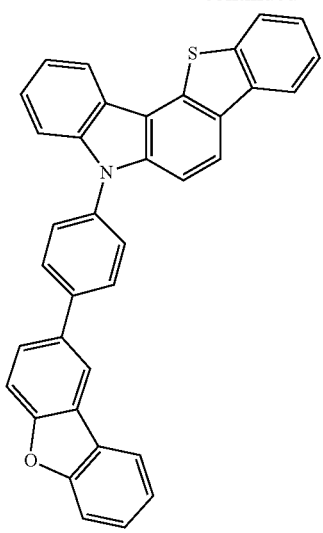
58
-continued
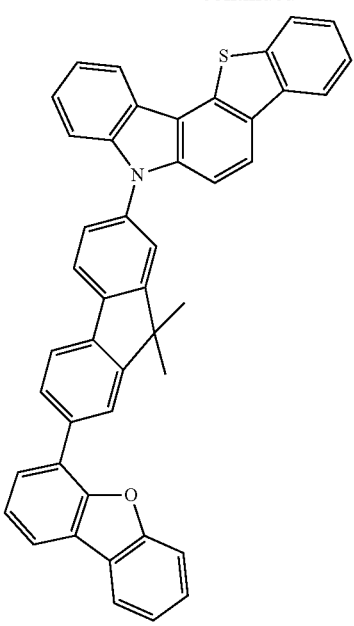
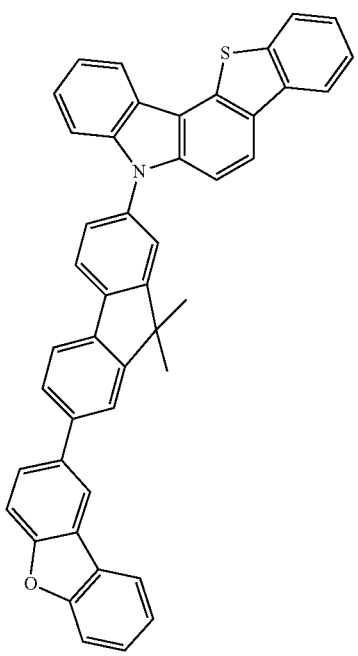
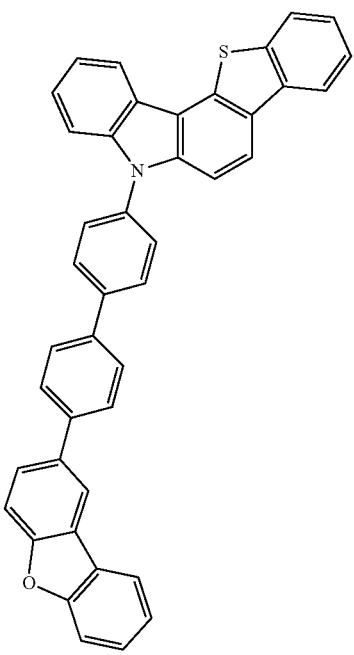

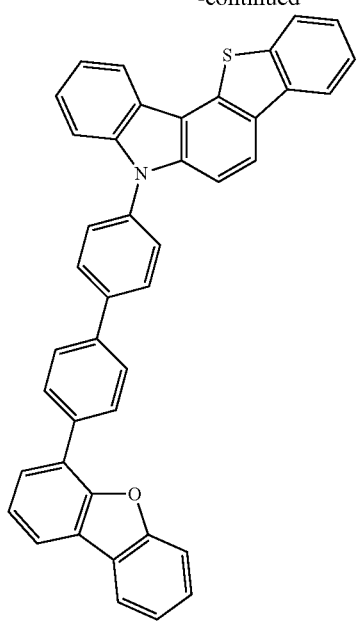
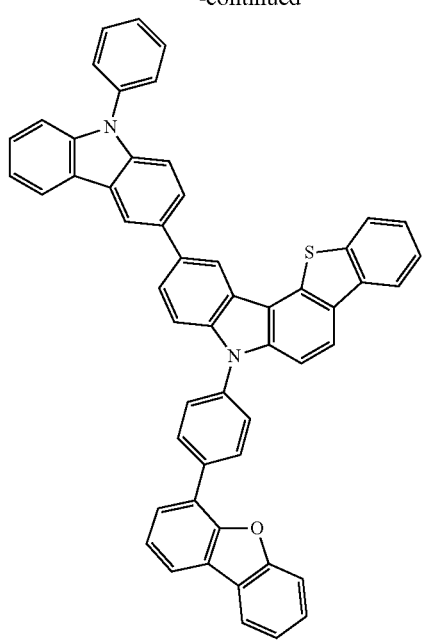
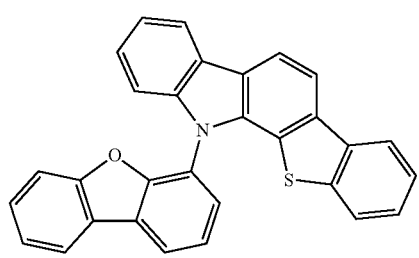
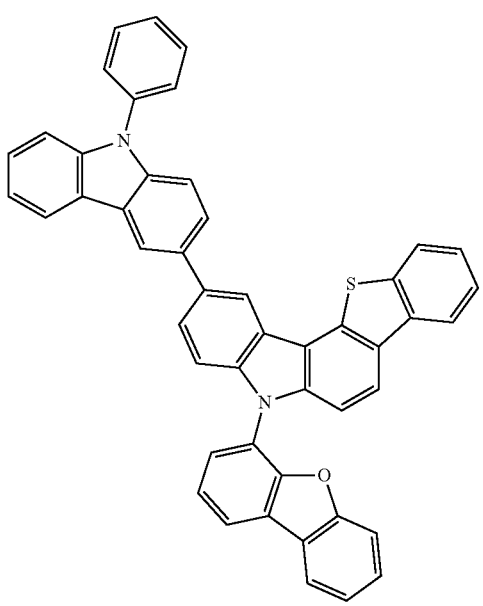

61
-continued
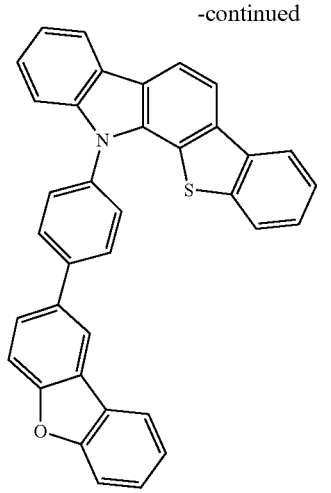
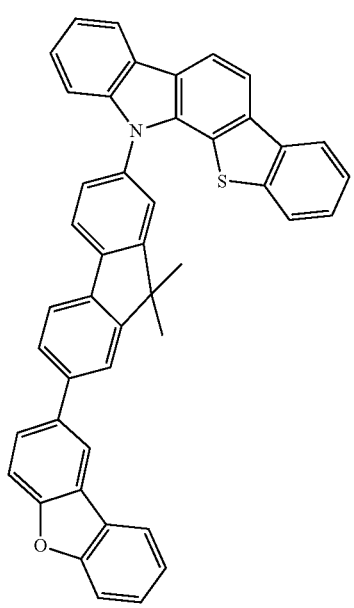
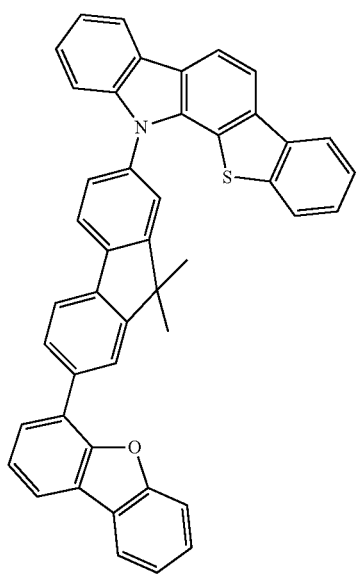
62
-continued
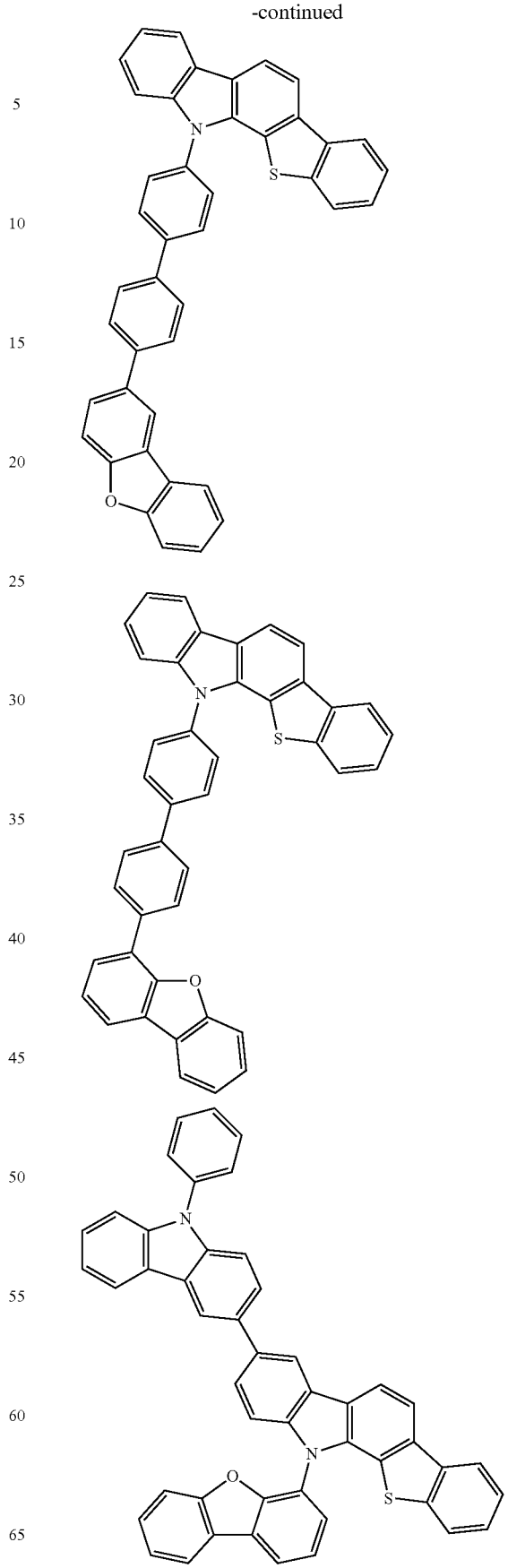

63
-continued
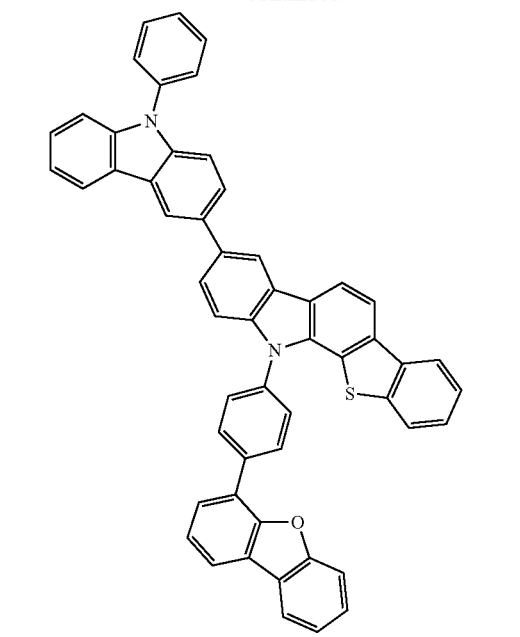
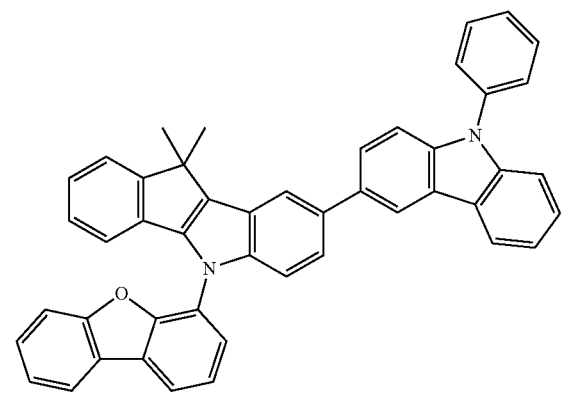
64
-continued
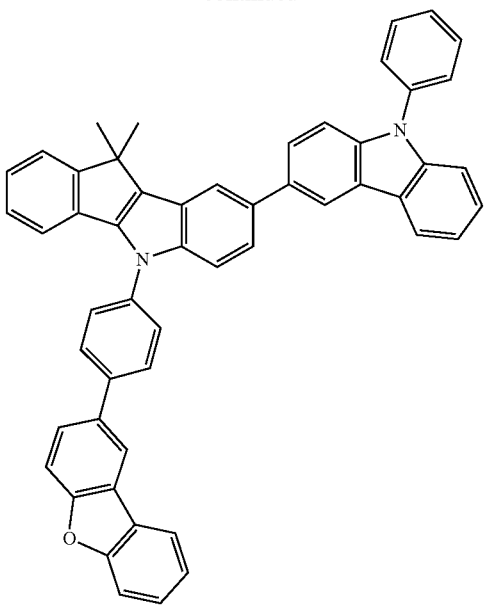
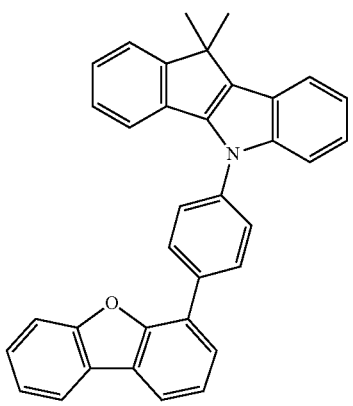
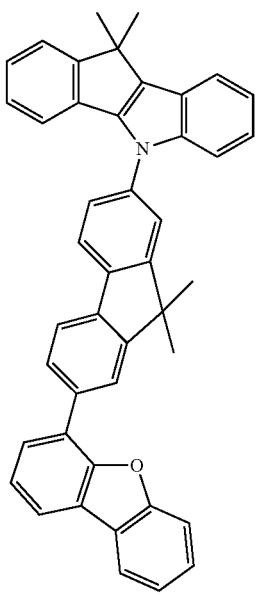

65
-continued
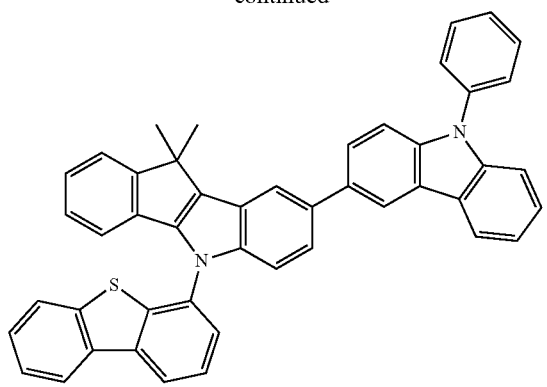
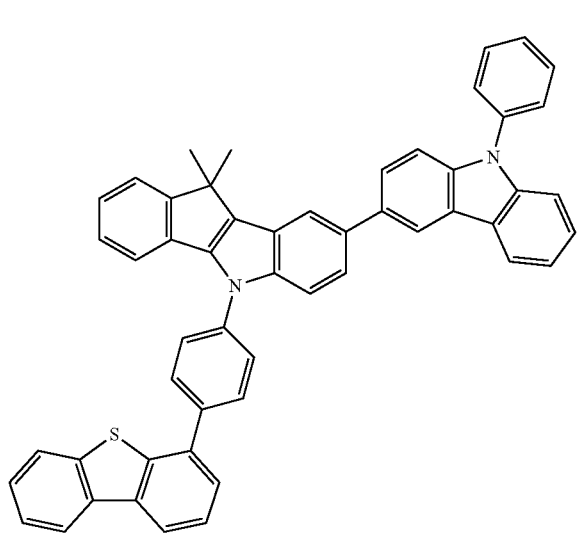
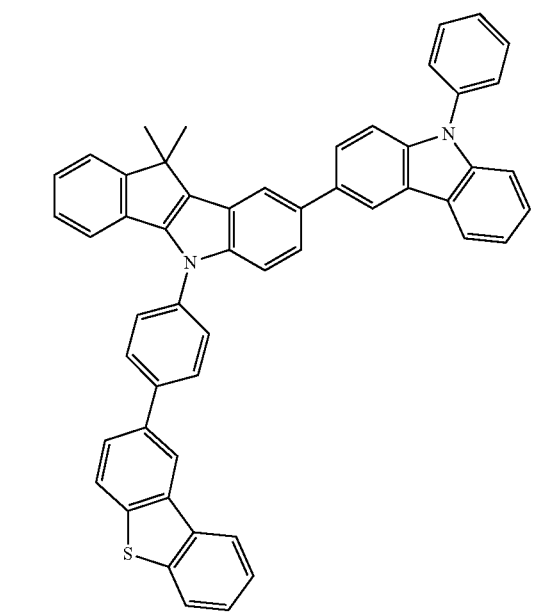
66
-continued
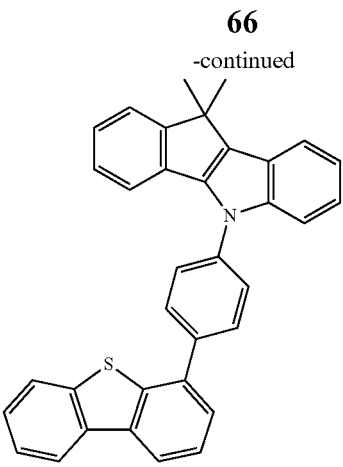
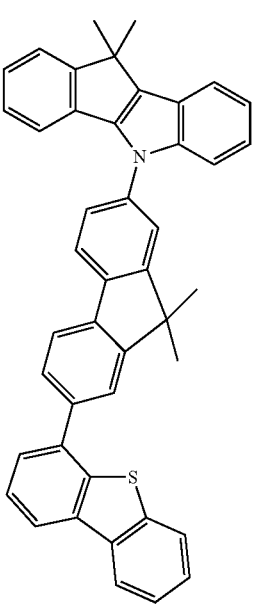
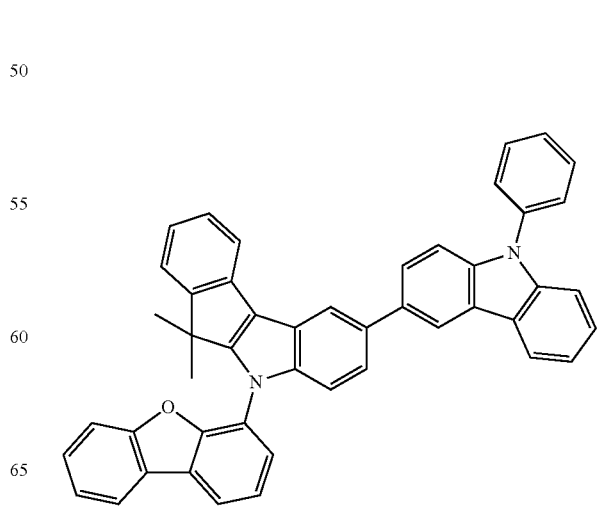

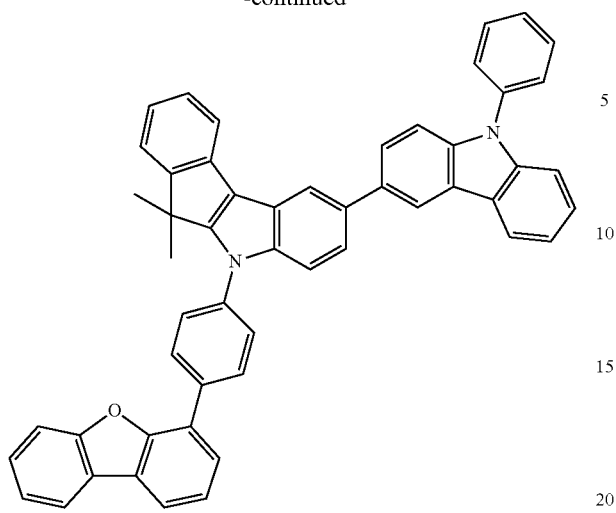
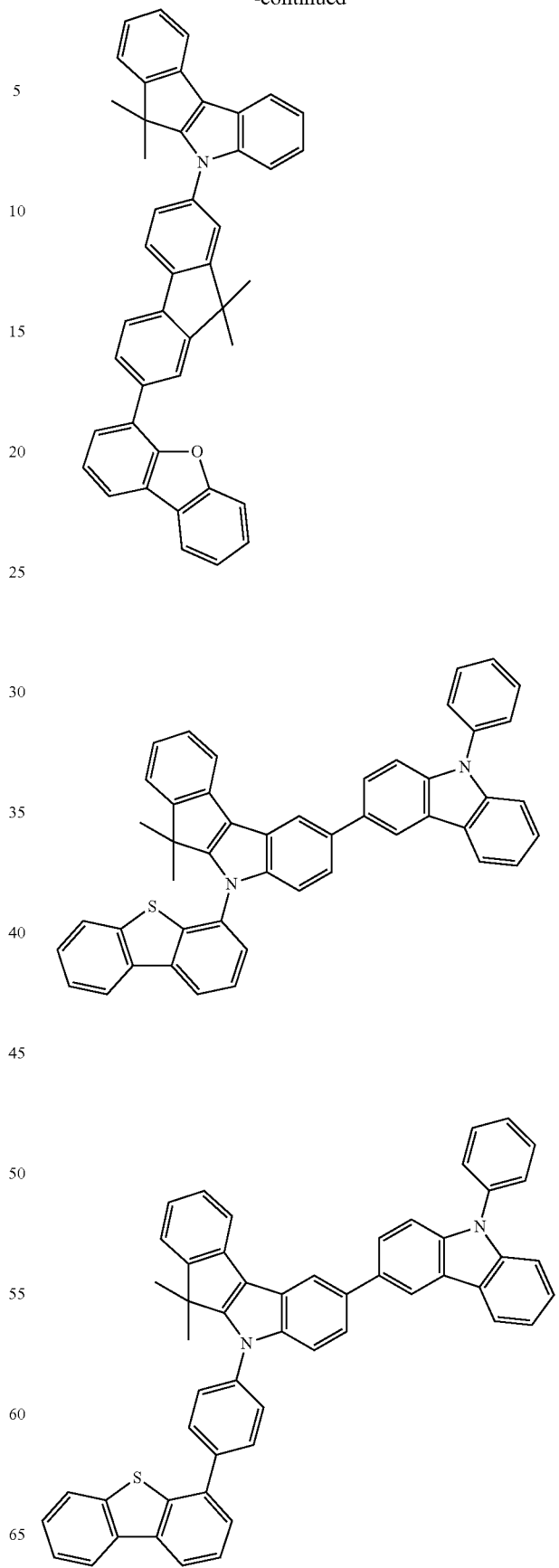

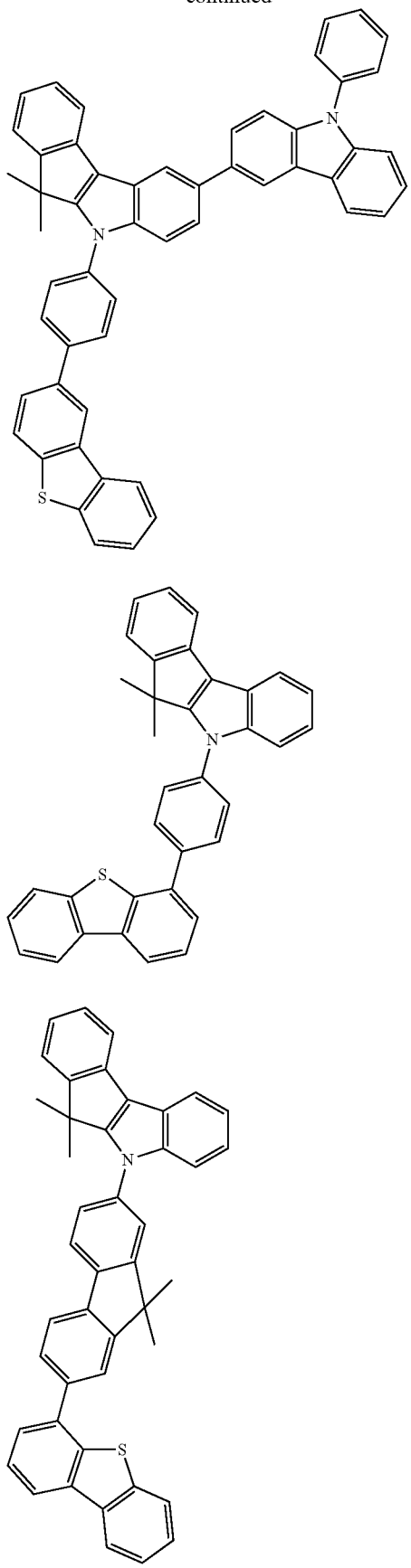
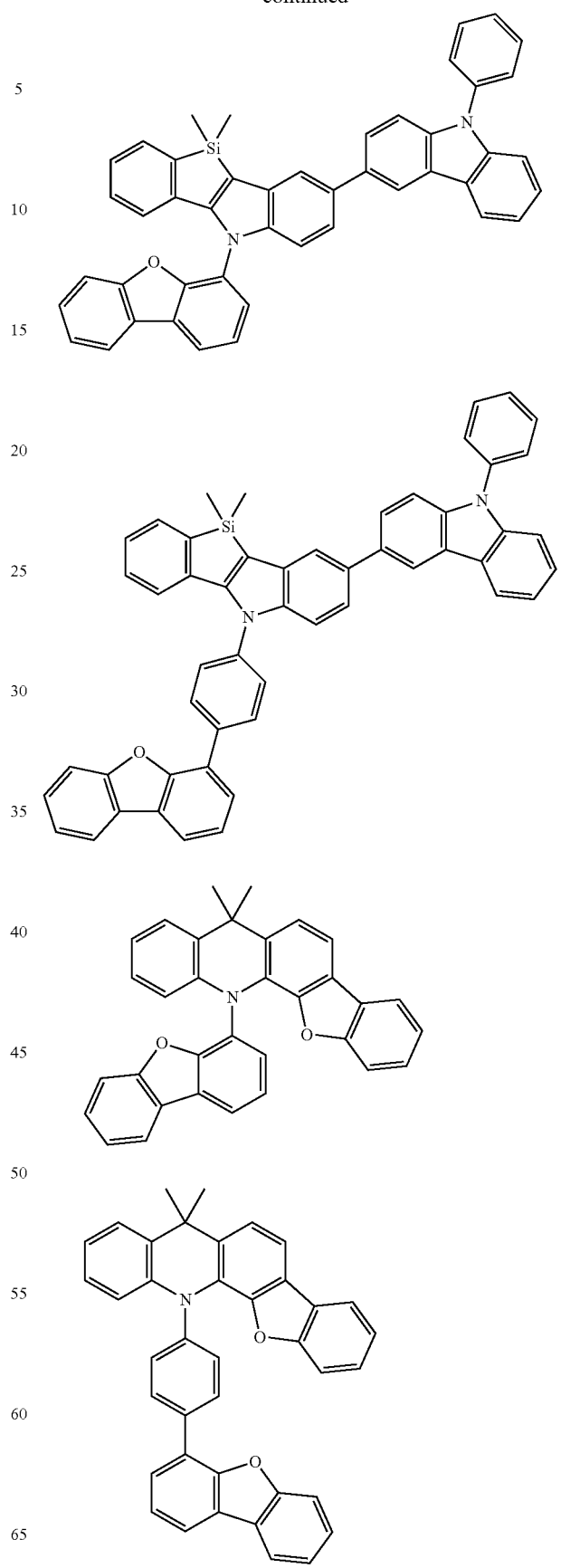

71
-continued
72
-continued
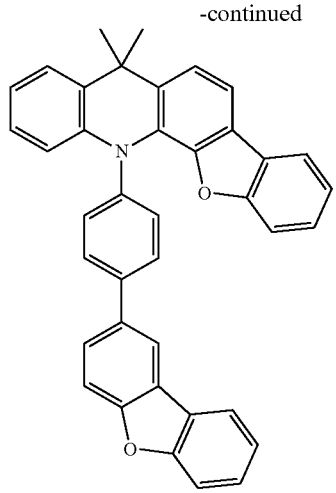
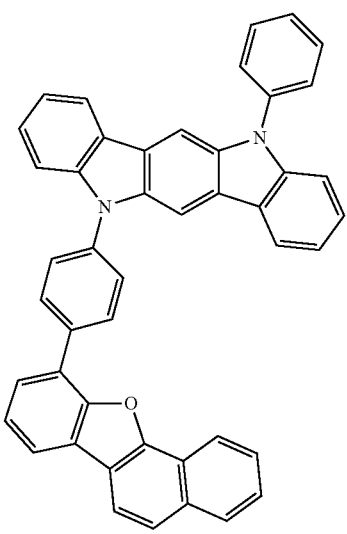
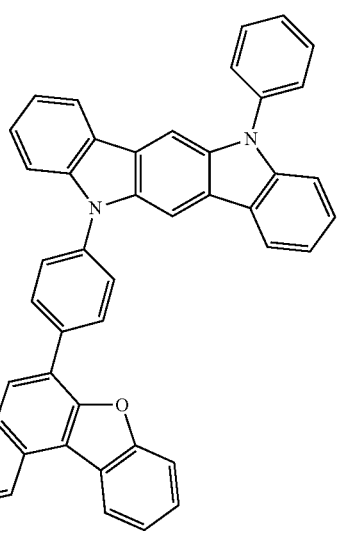
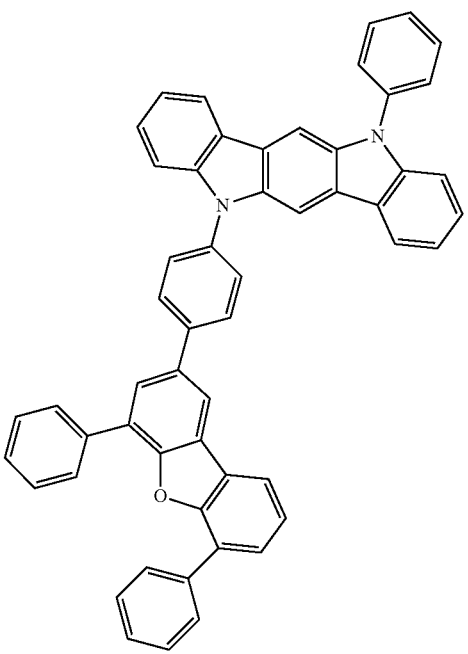

73
-continued
74
-continued
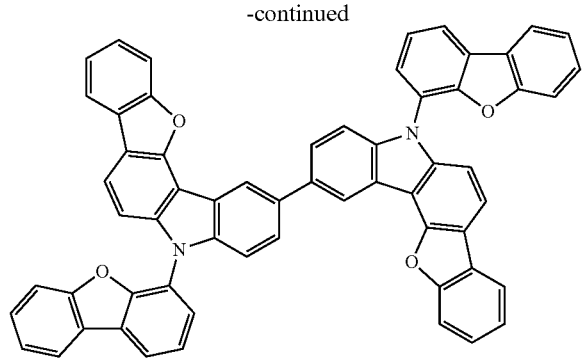
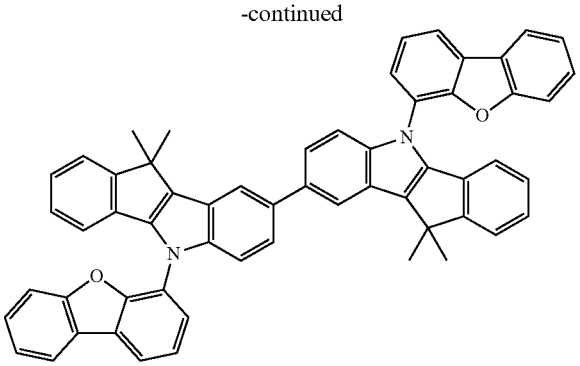
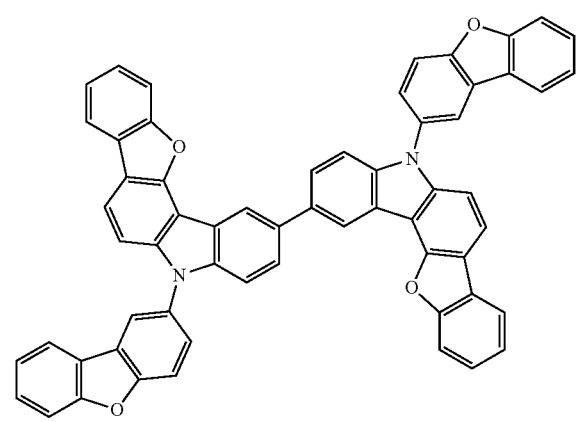
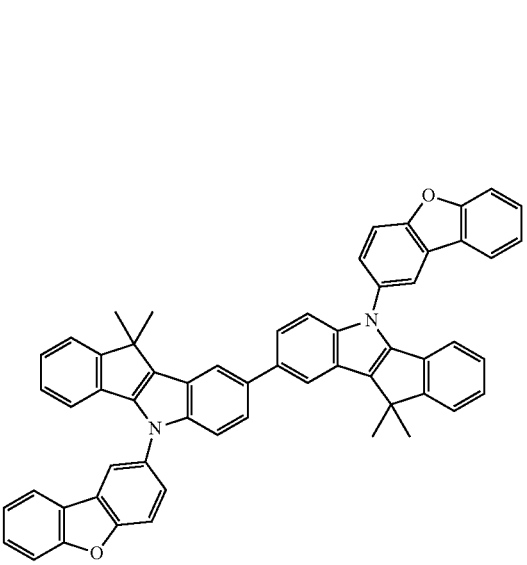
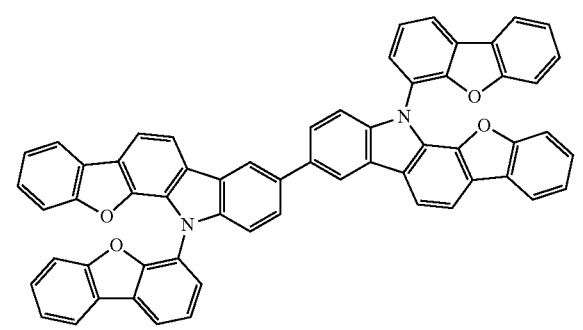
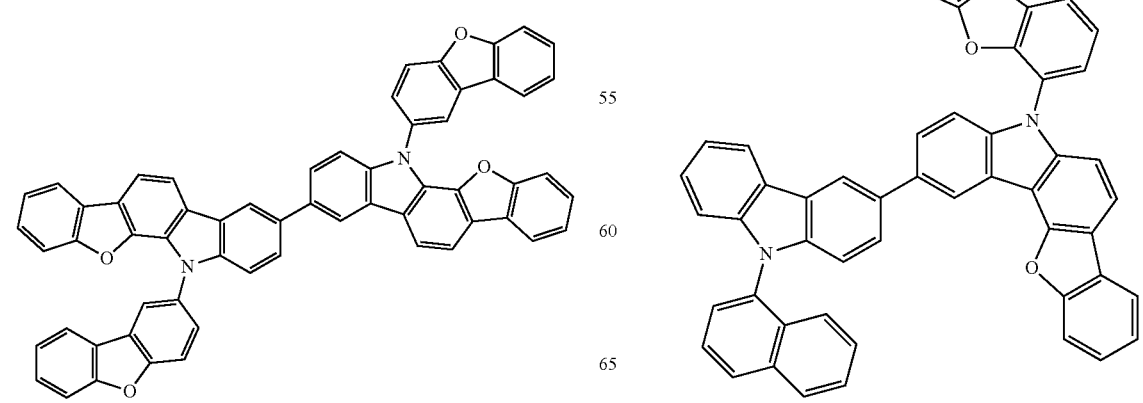

75
-continued
76
-continued
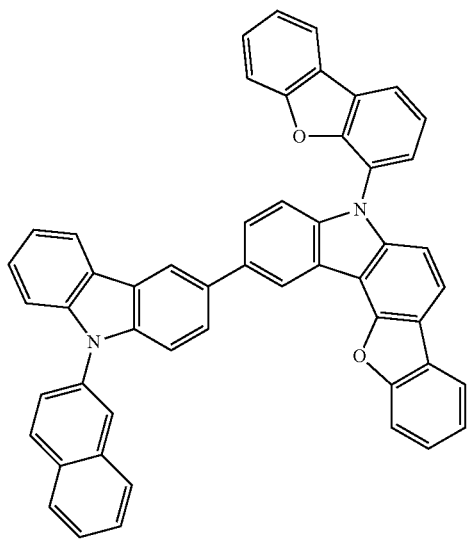
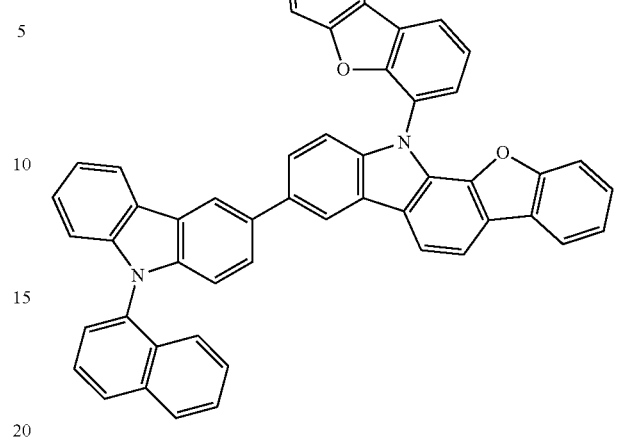
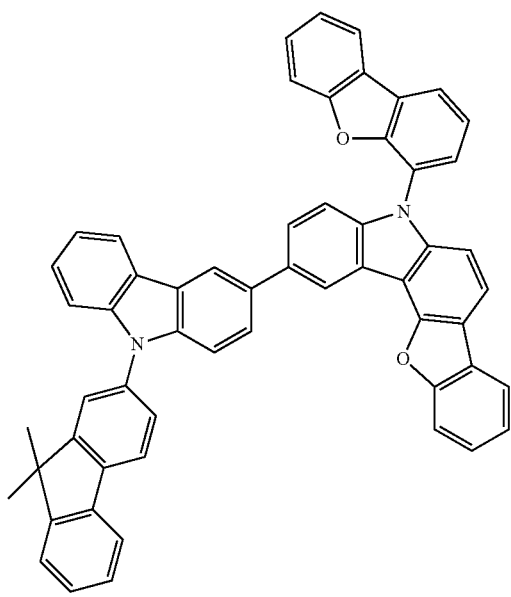
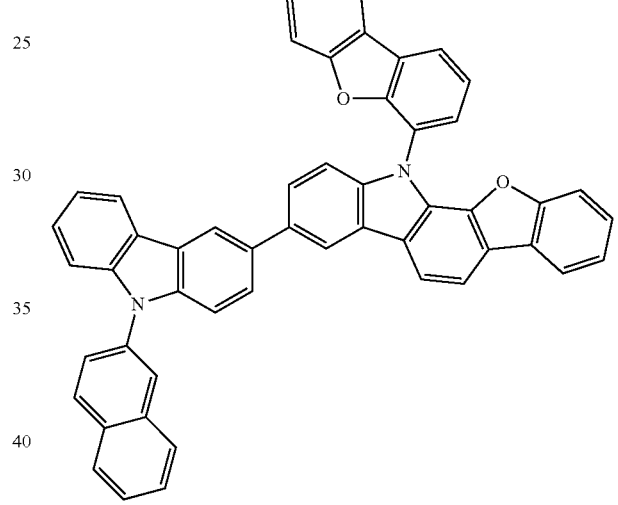
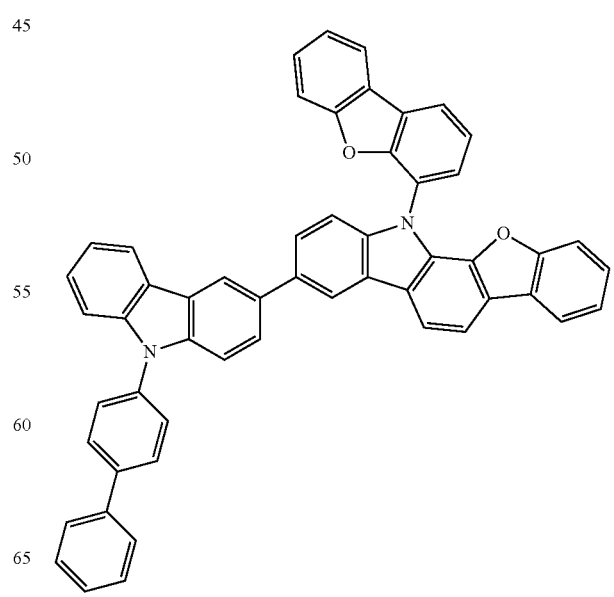

77
-continued
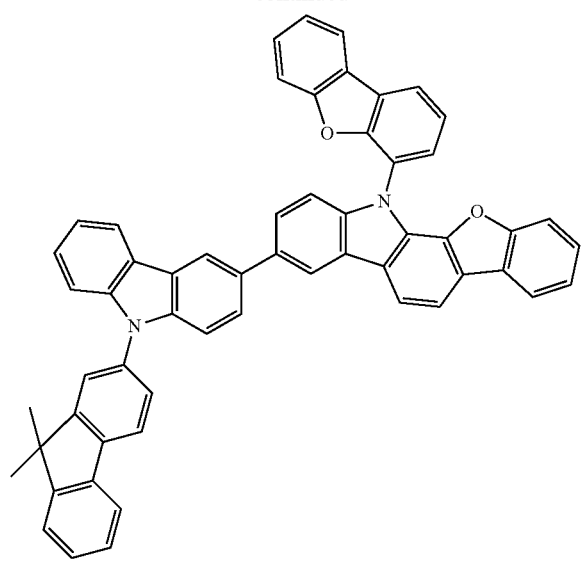
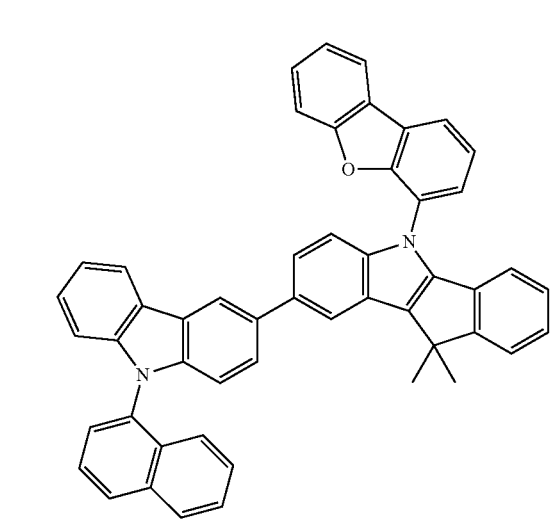
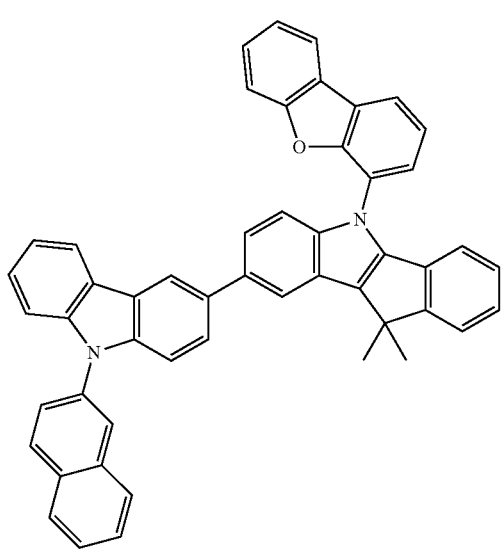
78
-continued
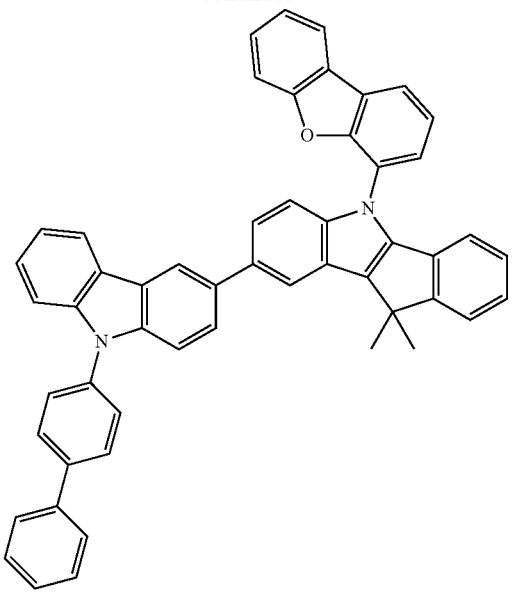
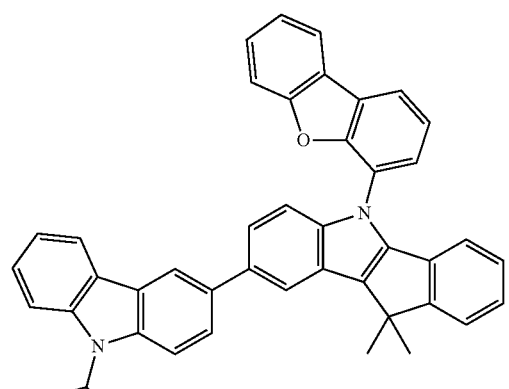
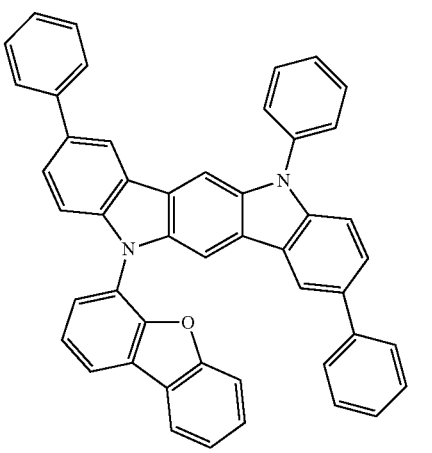

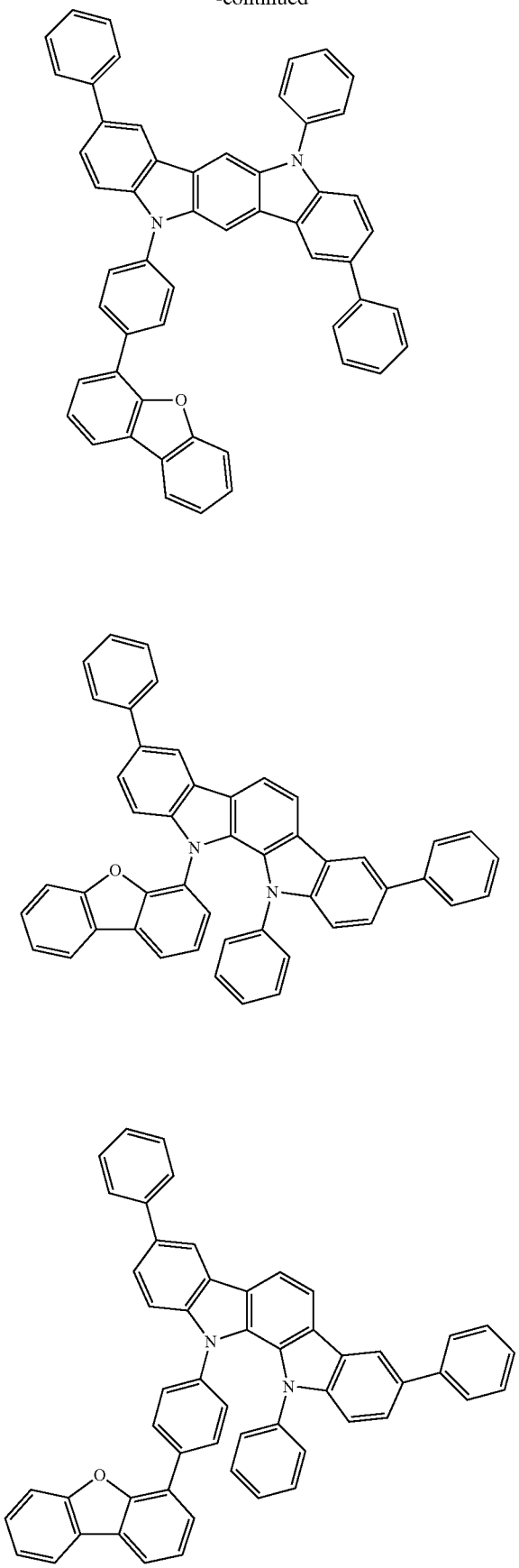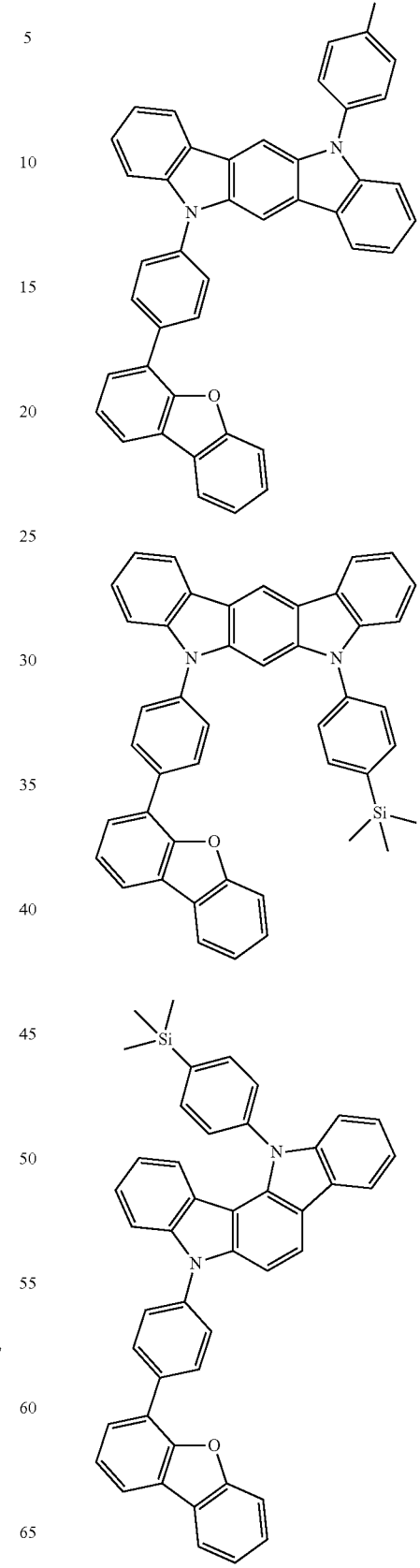

-continued

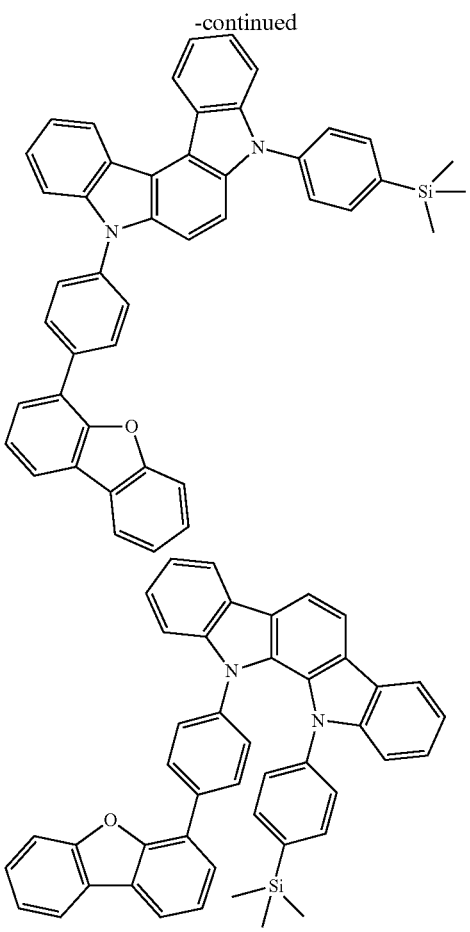

Organic EL Device

The organic EL device of the invention will be described below.

The organic EL device comprises organic thin film layers between the cathode the anode. The organic thin film layers comprise a light emitting layer and at least one layer of the organic thin film layers comprises the nitrogen-containing aromatic heterocyclic derivative of the invention mentioned above. By using the nitrogen-containing aromatic heterocyclic derivative of the invention in at least one layer of the organic thin film layers, an organic EL device with high emission efficiency and long lifetime is expected to obtain.

The organic thin film layer comprising the nitrogen-containing aromatic heterocyclic derivative of the invention may include a hole transporting layer, a light emitting layer, a space layer, and a blocking layer, although not limited thereto. The nitrogen-containing aromatic heterocyclic derivative of the invention is preferably used in a hole transporting layer. The light emitting layer preferably comprises a fluorescent material or a phosphorescent material, more preferably comprises a phosphorescent material.

The organic EL device of the invention may be any of a single color emitting device of fluorescent or phosphorescent type, a white-emitting device of fluorescent-phosphorescent hybrid type, an emitting device of a simple type having a single emission unit, and an emitting device of a tandem type having two or more emission units. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.
(1) Anode/Emission Unit/Cathode The emission unit may be a laminate comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below.

(a) hole transporting layer/light emitting layer (/electron transporting layer);

(b) hole transporting layer/first phosphorescent light emitting layer/second phosphorescent light emitting layer (/electron transporting layer);

(c) hole transporting layer/phosphorescent light emitting layer/space layer/fluorescent light emitting layer (/electron transporting layer);

(d) hole transporting layer/first phosphorescent light emitting layer/second phosphorescent light emitting layer/space layer/fluorescent light emitting layer (/electron transporting layer);

(e) hole transporting layer/first phosphorescent light emitting layer/space layer/second phosphorescent light emitting layer/space layer/fluorescent light emitting layer (/electron transporting layer); and (f) hole transporting layer/phosphorescent light emitting layer/space layer/first fluorescent light emitting layer/second fluorescent light emitting layer (/electron transporting layer).

The emission color of the phosphorescent light emitting layer and that of the fluorescent light emitting layer may be different. For example, the layered structure of the laminated light emitting layer (d) may be hole transporting layer/first phosphorescent light emitting layer (red emission)/second phosphorescent light emitting layer (green emission)/space layer/fluorescent light emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such a electron blocking layer or a hole blocking layer, electrons and holes are confined in the light emitting layer to increase the degree of charge recombination in the light emitting layer, thereby improving the emission efficiency.

Representative device structure of the tandem-type organic EL device is shown below.
(2) Anode/First Emission Unit/Intermediate Layer/Second Emission Unit/Cathode The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device of the invention is shown in FIG. 1 wherein the organic EL device 1 comprises a substrate 2, an anode 3, a cathode 4, and an emission unit 10 disposed between the anode 3 and the cathode 4. The emission unit 10 comprises a light emitting layer 5 which comprises at least one phosphorescent emitting layer containing a phosphorescent host material and a phosphorescent dopant. A hole transporting layer 6, etc. may be disposed between the light emitting layer 5 and the anode 3, and an electron transporting layer 7, etc. may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the degree of exciton generation in the light emitting layer 5.

In the present invention, the host is referred to as a fluorescent host when combinedly used with a fluorescent dopant and as a phosphorescent host when combinedly used with a phosphorescent dopant. Therefore, the fluorescent host and the phosphorescent host are not distinguished from each other merely by the difference in their molecular structures. Namely, the term "phosphorescent host" means a material for constituting a phosphorescent emitting layer containing a phosphorescent dopant and does not mean that the material is not usable as a material for constituting a fluorescent emitting layer. The same also applies to the fluorescent host.

Substrate

The organic EL device of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of material for anode include indium tin oxide alloy (ITO), tin oxide (NESA), indium zinc oxide alloy, gold, silver, platinum, and copper. The anode is formed by making the electrode material into a thin film by a method, such as a vapor deposition method or a sputtering method. When getting the light emitted from the light emitting layer through the anode, the transmittance of anode to visible light is preferably more than 10%. The sheet resistance of anode is preferably several hundreds $\Omega/\square$ or less. The film thickness of anode depends upon the kind of material and generally 10 nm to 1 µm, preferably 10 to 200 nm.

Cathode

The cathode injects electrons to the electron injecting layer, the electron transporting layer or the light emitting layer, and preferably formed from a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material into a thin film by a method, such as the vapor deposition method and the sputtering method. The emitted light may be taken from the cathode, if appropriate.

Light Emitting Layer

The light emitting layer is an organic layer having a light emitting function. A light emitting layer employing a doping system comprises a host material and a dopant material, wherein the major function of the host material is to promote the recombination of electrons and holes and confine excitons in the light emitting layer, and the dopant material causes the excitons generated by recombination to emit light efficiently.

In case of a phosphorescent device, the major function of the host material is to confine the excitons generated on the dopant in the light emitting layer.

To control the carrier balance in the light emitting layer, a double host (host and co-host) system may be used for the light emitting layer, for example, by combinedly using an electron transporting host and a hole transporting host.

The light emitting layer may be made into a double dopant layer, in which two or more kinds of dopant materials having high quantum yield are combinedly used and each dopant material emits light with its own color. For example, to obtain a yellow emission, a light emitting layer formed by co-depositing a host, a red-emitting dopant and a green-emitting dopant is used.

In a laminate of two or more light emitting layers, electrons and holes are accumulated in the interface between the light emitting layers, and therefore, the recombination region is localized in the interface between the light emitting layers, to improve the quantum efficiency.

The light emitting layer may be different in the hole injection ability and the electron injection ability, and also in the hole transporting ability and the electron transporting ability each being expressed by mobility.

The light emitting layer is formed, for example, by a known method, such as a vapor deposition method, a spin coating method, and LB method. Alternatively, the light emitting layer may be formed by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The phosphorescent dopant (phosphorescent emitting material) is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. A ligand having an ortho metal bond is preferred. In view of obtaining a high phosphorescent quantum yield and further improving the external quantum efficiency of electroluminescence device, a metal complex comprising a metal selected from Ir, Os, and Pt is preferred, with iridium complex, osmium complex, and platinum being more preferred, iridium complex and platinum complex being still more preferred, and an ortho metallated iridium complex being particularly preferred.

The content of the phosphorescent dopant in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.
Preferred examples of the organometallic complex are shown below.
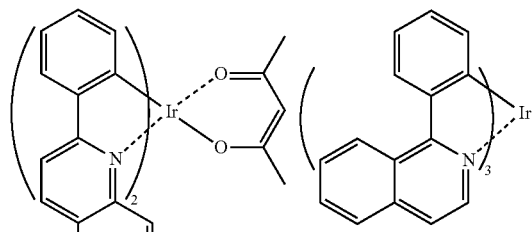
PQIr
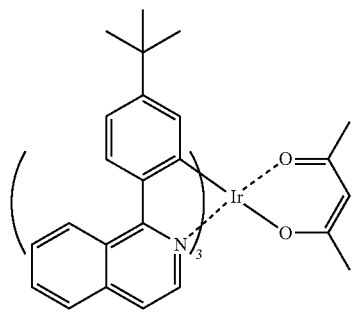
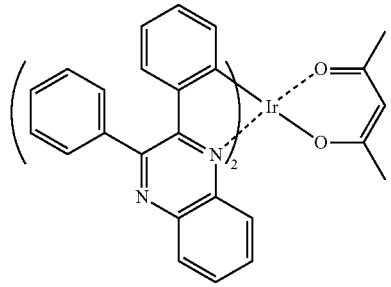
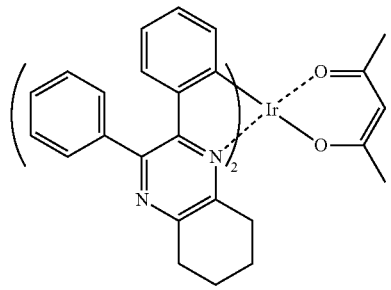
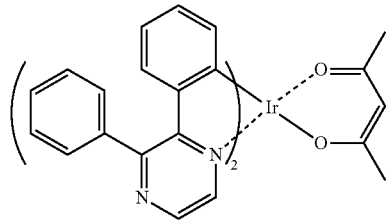
-continued
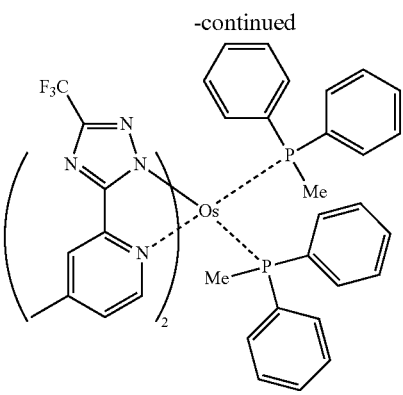
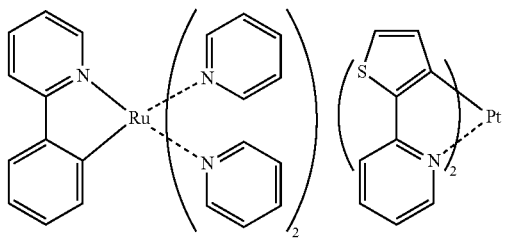
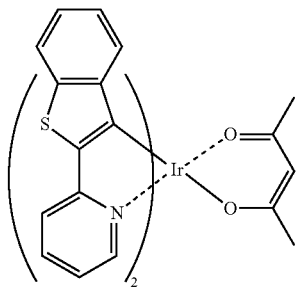
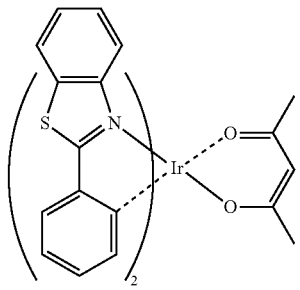
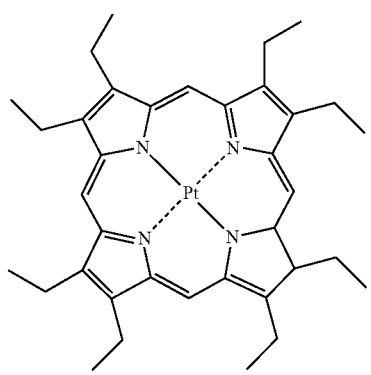

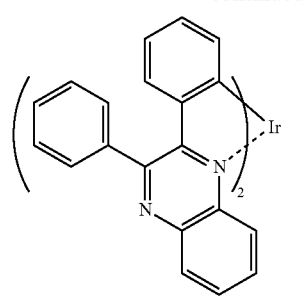
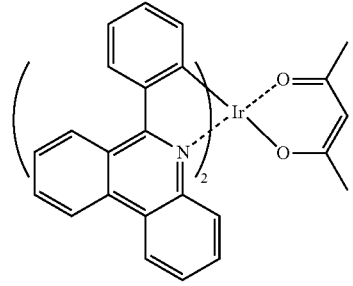
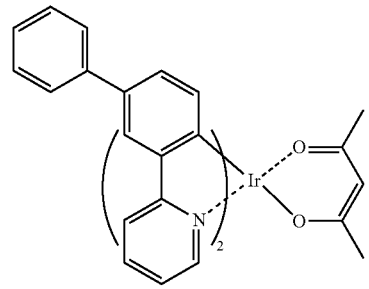
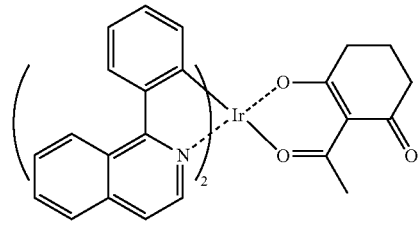
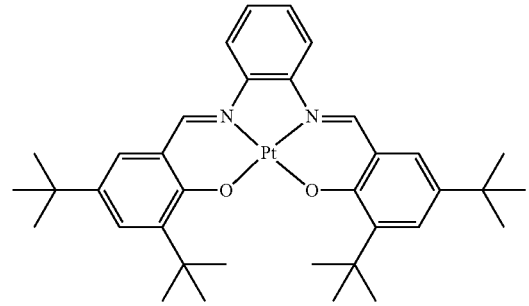
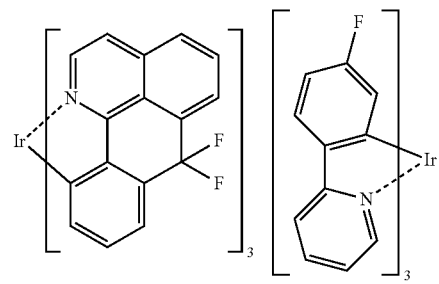
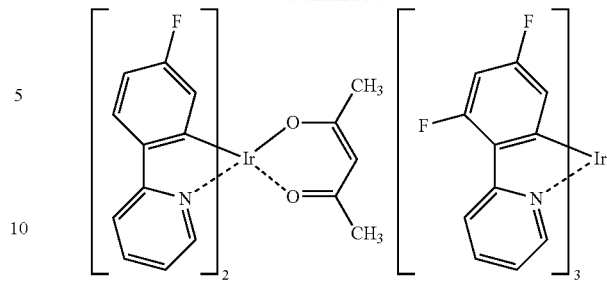
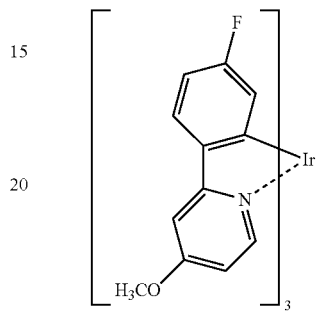
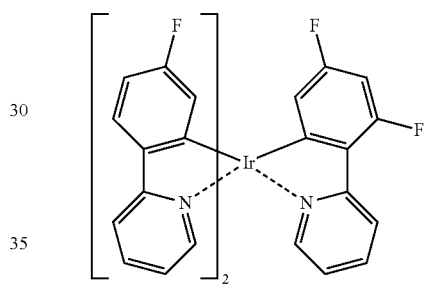
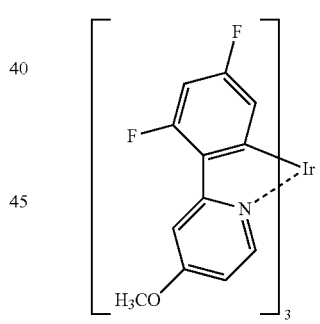
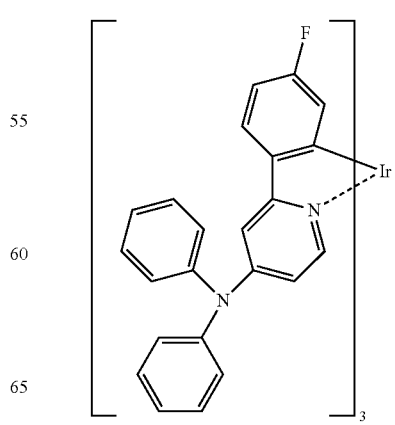

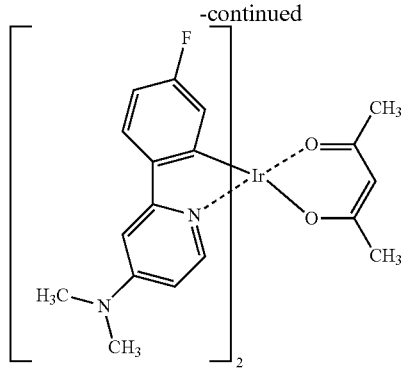
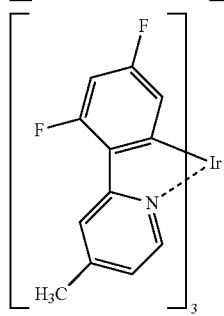
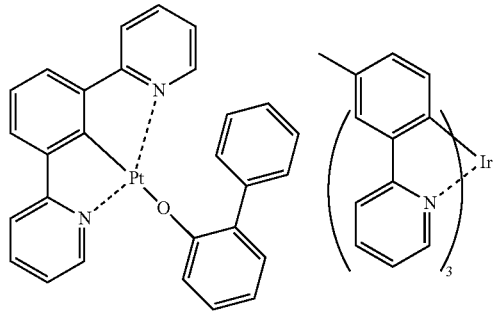
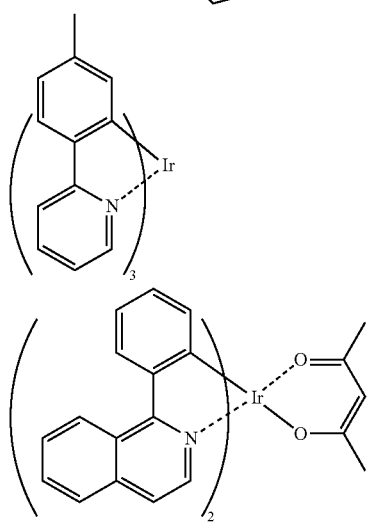
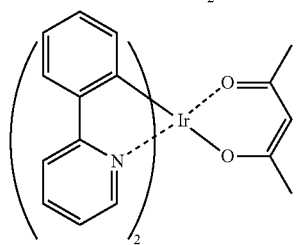
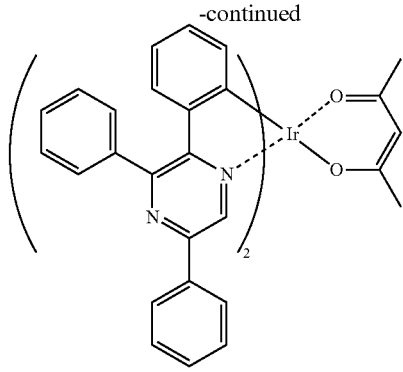
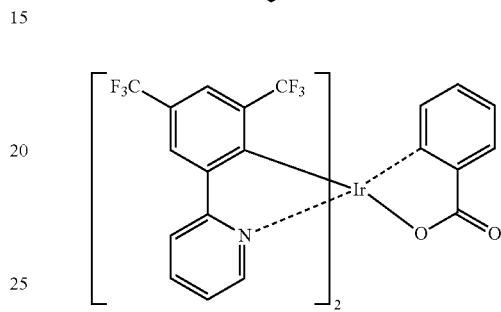
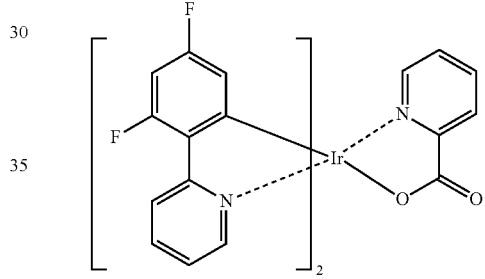
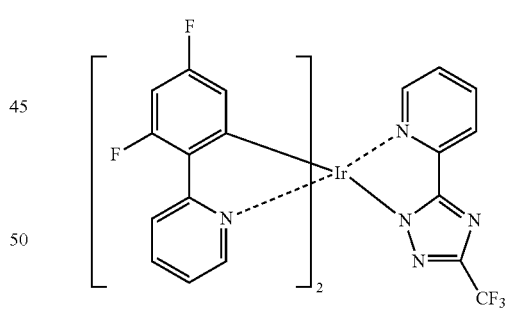
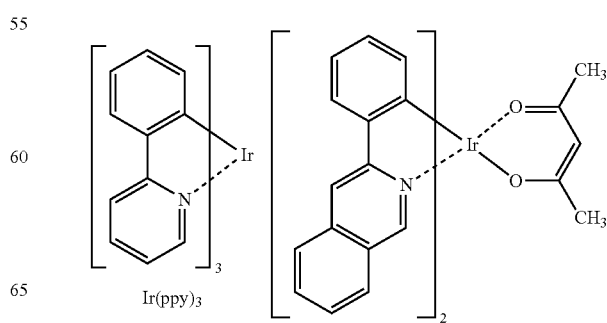
Ir(ppy)₃

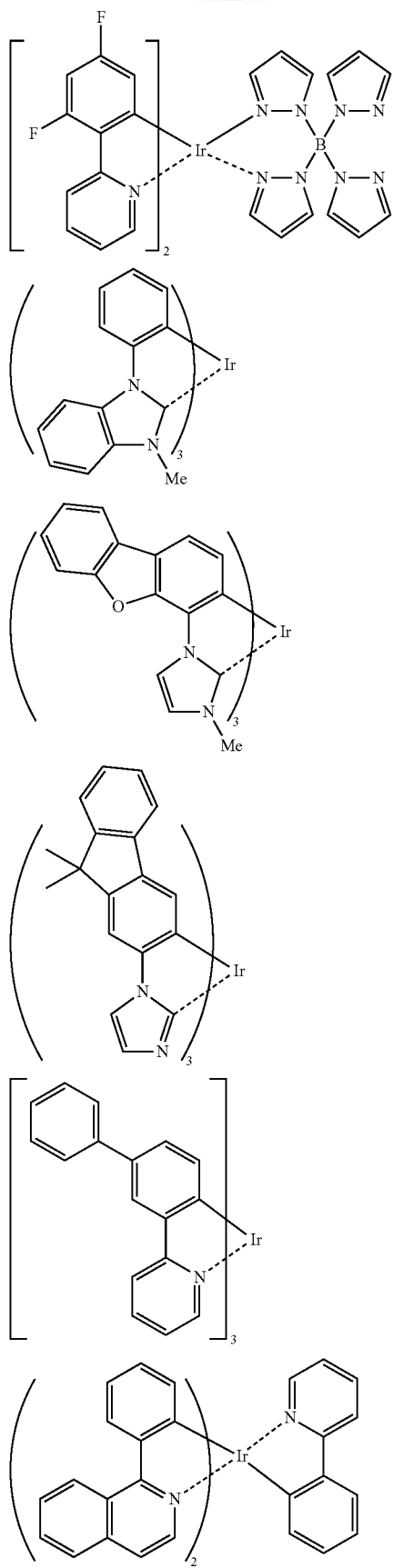
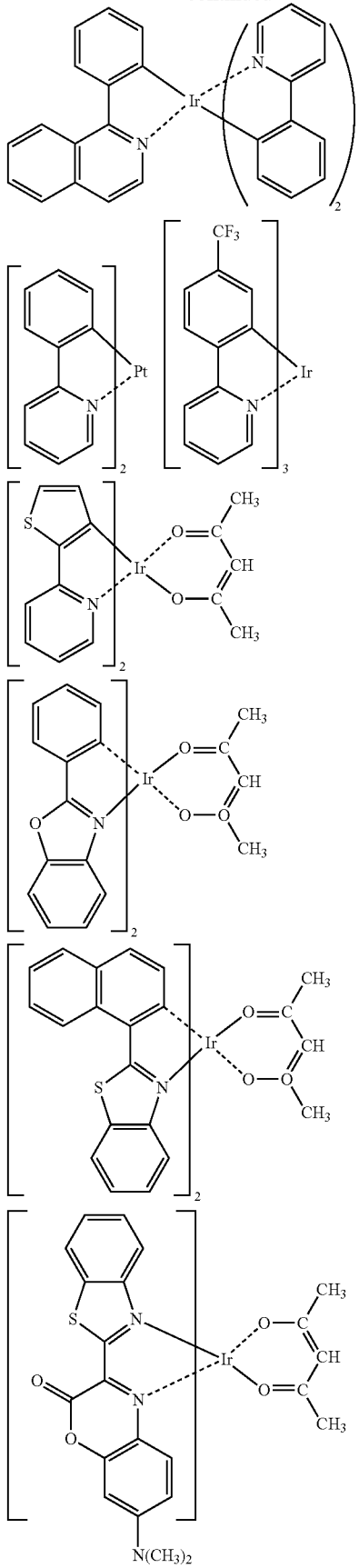

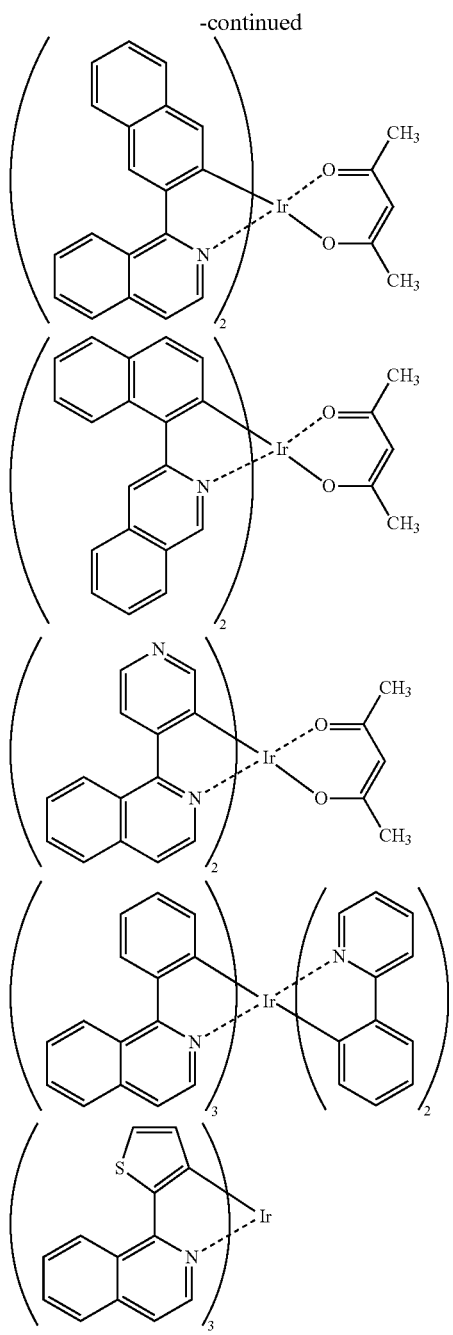

emitting layers as the phosphorescent host material and a compound other than the nitrogen-containing aromatic heterocyclic derivative of the invention can be used in another light emitting layer as the phosphorescent host material. The nitrogen-containing aromatic heterocyclic derivative of the invention may be used in an organic layer other than the light emitting layer. In this case, a compound other than the nitrogen-containing aromatic heterocyclic derivative of the invention may be used as a phosphorescent host of the light emitting layer.

Examples of the compounds other than the nitrogen-containing aromatic heterocyclic derivative of the invention, which are suitable as the phosphorescent host, include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic methylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Specific examples thereof are shown below.

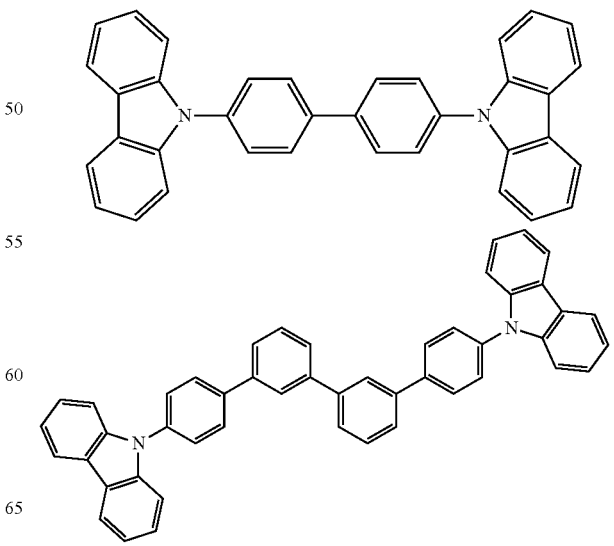

The phosphorescent host is a compound which confines the triplet energy of the phosphorescent dopant efficiently in the light emitting layer to cause the phosphorescent dopant to emit light efficiently. The nitrogen-containing aromatic heterocyclic derivative of the invention is useful as a phosphorescent host. If necessary, in addition to the nitrogen-containing aromatic heterocyclic derivative of the invention, another compound may be used as the phosphorescent host according to the use of the device.

The nitrogen-containing aromatic heterocyclic derivative of the invention and another compound may be combinedly used in the same light emitting layer as the phosphorescent host material. If two or more light emitting layers are formed, the nitrogen-containing aromatic heterocyclic derivative of the invention can be used in one of the light

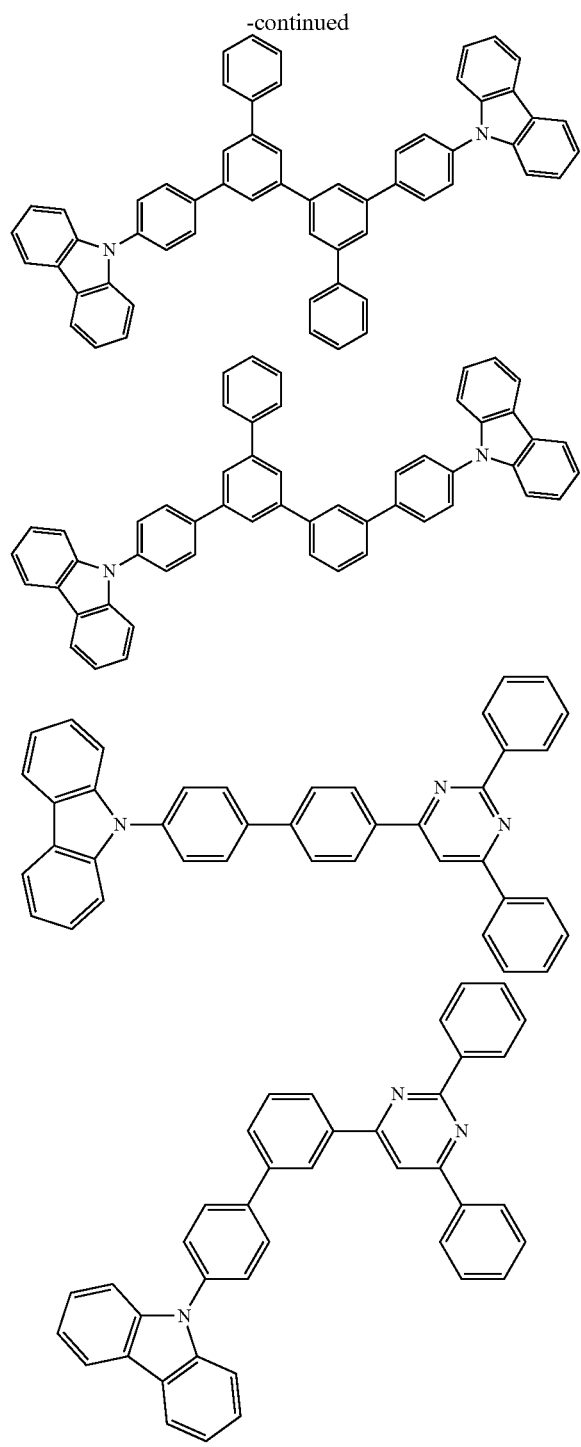

The thickness of the light emitting layer is preferably 5 to 50 nm, more preferably 7 to 50 nm, and still more preferably 10 to 50 nm. If being 5 nm or more, the light emitting layer is easily formed. If being 50 nm or less, the increase in driving voltage is avoided.

Electron-Donating Dopant

It is preferred for the organic EL device of the invention to contain an electron-donating dopant in the interfacial region between the cathode and the light emitting unit. With such a construction, the organic EL device has an improved luminance and an elongated lifetime. The electron-donating dopant is a metal having a work function of 3.8 eV or less or a compound containing such metal. Examples thereof include at least one compound selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ (0<x<1) and $Ba_xCa_{1-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal complex are not particularly limited as long as containing at least one metal ion selected from alkali metal ions, alkaline earth metal ions, rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant is added to the interfacial region preferably into a form of layer or island. The electron-donating dopant is added preferably by co-depositing the electron-donating dopant with the organic compound (light emitting material, electron injecting material, etc.) for forming the interfacial region by a resistance heating deposition method, thereby dispersing the electron-donating dopant into the organic material. The disperse concentration expressed by the molar ratio of the organic material and the electron-donating dopant is 100:1 to 1:100 and preferably 5:1 to 1:5.

When the electron-donating dopant is formed into a form of layer, a light emitting material or an electron injecting material is made into a layer which serves as an organic layer in the interface, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island which serves as an organic layer in the interface, and then, the electron-donating dopant alone is deposited by a resistance heating deposition method into a form of island having a thickness preferably 0.05 to 1 nm.

The molar ratio of the main component and the electron-donating dopant in the organic electroluminescence device of the invention is preferably 5:1 to 1:5 and more preferably 2:1 to 1:2.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently.

An aromatic heterocyclic compound having one or more heteroatoms in its molecule is preferably used as the electron transporting material for the electron transporting layer, with a nitrogen-containing ring derivative being particularly preferred. The nitrogen-containing ring derivative is preferably an aromatic ring compound having a nitrogen-containing 6- or 5-membered ring or a condensed aromatic ring compound having a nitrogen-containing 6- or 5-membered ring.

The nitrogen-containing ring derivative is preferably, for example, a chelate metal complex having a nitrogen-containing ring represented by formula (A).

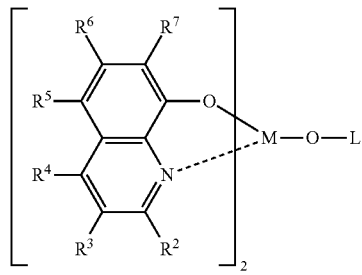

(A)

$R^2$ to $R^7$ of formula (A) each independently represent a hydrogen atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group, or a heterocyclic group having 5 to 50 carbon atoms, each being optionally substituted.

The halogen atom may include fluorine, chlorine, bromine, and iodine.

The substituted amino group may include an alkylamino group, an arylamino group, and an aralkylamino group.

The alkylamino group and the aralkylamino group are represented by $-NQ^1Q^2$, wherein $Q^1$ and $Q^2$ each independently represent an alkyl group having 1 to 20 carbon atoms or an aralkyl group having 1 to 20 carbon atoms. One of $Q^1$ and $Q^2$ may be a hydrogen atom.

The arylamino group is represented by $-NAr^1Ar^2$, wherein $Ar^1$ and $Ar^2$ each independently represent a non-condensed aromatic hydrocarbon group or a condensed aromatic hydrocarbon group each having 6 to 50 carbon atoms. One of $Ar^1$ and $Ar^2$ may be a hydrogen atom.

The hydrocarbon group having 1 to 40 carbon atoms may include an alkyl group, an alkenyl group, a cycloalkyl group, an aryl group, and an aralkyl group.

The alkoxycarbonyl group is represented by $-COOY'$, wherein $Y'$ is an alkyl group having 1 to 20 carbon atoms.

M represents aluminum (Al), gallium (Ga), or indium (In), with In being preferred.

L represents a group represented by formula (A') or (A''):

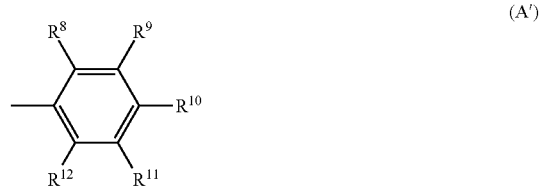

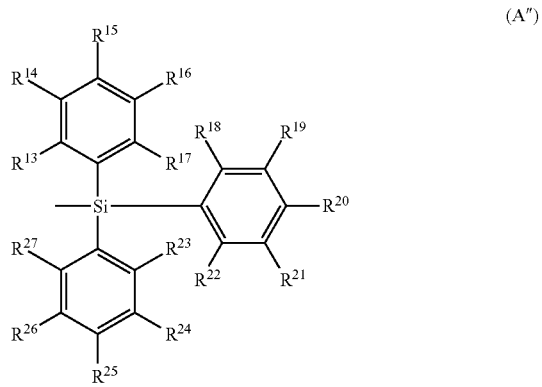

$R^8$ to $R^{12}$ in formula (A') each independently represent a hydrogen atom or a substituted or unsubstituted hydrocarbon group having 1 to 40 carbon atoms. The adjacent two groups may form a ring structure. $R^{13}$ to $R^{27}$ in formula (A'') each independently represent a hydrogen atom or a substituted or unsubstituted hydrocarbon group having 1 to 40 carbon atoms. The adjacent two groups may form a ring structure.

Examples of the hydrocarbon group having 1 to 40 carbon atoms for $R^8$ to $R^{12}$ and $R^{13}$ to $R^{27}$ in formulae (A') and (A'') are the same as those described above with respect to $R^2$ to $R^7$ of formula (A). Examples of the divalent group formed by the adjacent two groups of $R^8$ to $R^{12}$ and $R^{13}$ to $R^{27}$ which completes the ring structure include tetramethylene group, pentamethylene group, hexamethylene group, diphenylmethane-2,2'-diyl group, diphenylethane-3,3'-diyl group, and diphenylpropane-4,4'-diyl group.

The electron transporting compound for the electron transporting layer is preferably a metal complex including 8-hydroxyquinoline or its derivative, an oxadiazole derivative, and a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below.

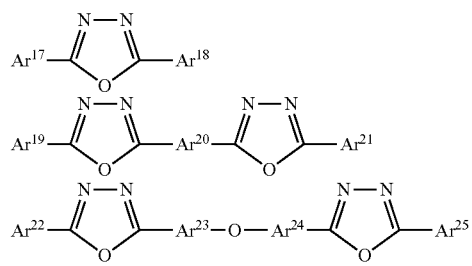

In the above formulae, each of $Ar^{17}$, $Ar^{18}$, $Ar^{19}$, $Ar^{21}$, $Ar^{22}$, and $Ar^{25}$ is a substituted or unsubstituted aromatic hydrocarbon group or a substituted or unsubstituted condensed aromatic hydrocarbon group each having 6 to 50 carbon atoms, and $Ar^{17}$ and $Ar^{18}$, $Ar^{19}$ and $Ar^{21}$, and $Ar^{22}$ and $Ar^{25}$ may be the same or different. Examples of the aromatic hydrocarbon group and the condensed aromatic hydrocarbon group include phenyl group, naphthyl group, biphenyl group, anthranyl group, perylenyl group, and pyrenyl group. The optional substituent may be an alkyl group having 1 to 10 carbon atoms, an alkoxyl group having 1 to 10 carbon atoms or a cyano group.

Each of $Ar^{20}$, $Ar^{23}$, and $Ar^{24}$ is a substituted or unsubstituted divalent aromatic hydrocarbon group or a substituted or unsubstituted divalent condensed aromatic hydrocarbon group each having 6 to 50 carbon atoms, and $Ar^{23}$ and $Ar^{24}$ may be the same or different. Examples of the divalent aromatic hydrocarbon group or the divalent condensed aromatic hydrocarbon group include phenylene group, naphthylene group, biphenylene group, anthranylene group, perylenylene group, and pyrenylene group. The optional substituent may be an alkyl group having 1 to 10 carbon atoms, an alkoxyl group having 1 to 10 carbon atoms or a cyano group.

Electron transporting compounds which have a good thin film-forming property are preferably used. Examples of the electron transporting compound are shown below.

In formula (C), X is a carbon atom or a nitrogen atom. $Z_1$ and $Z_2$ each independently represent a group of atoms for completing the nitrogen-containing heteroring.

The nitrogen-containing heterocyclic derivative is more preferably an organic compound which has a nitrogen-containing aromatic polycyclic ring comprising a 5-membered ring or a 6-membered ring. A nitrogen-containing aromatic polycyclic compound having two or more nitrogen atoms which has a skeleton comprising (B) and (C) or a skeleton comprising (B) and (D) is also preferred.

(D)

The nitrogen-containing group of the nitrogen-containing aromatic polycyclic compound is selected, for example, from the nitrogen-containing heterocyclic groups shown below.

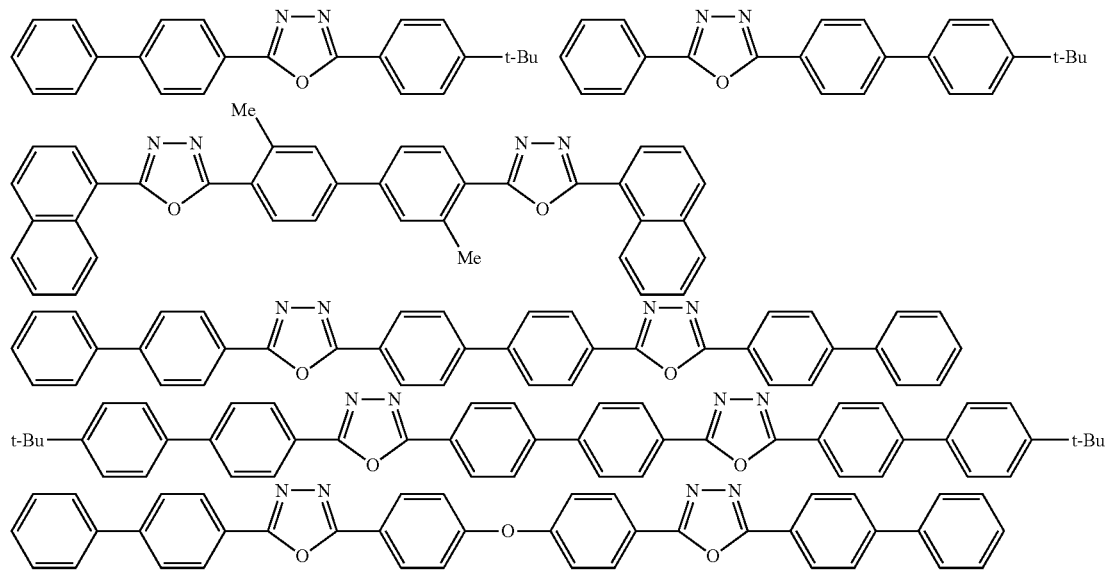

Examples of the nitrogen-containing heterocyclic derivative for use as the electron transporting compound include a nitrogen-containing heterocyclic derivative having the following formulae but exclusive of metal complex, for example, a compound having a 5- or 6-membered ring which has the skeleton represented by formula (B) or having the structure represented by formula (C).

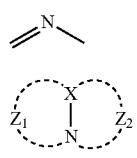

(B)

(C)

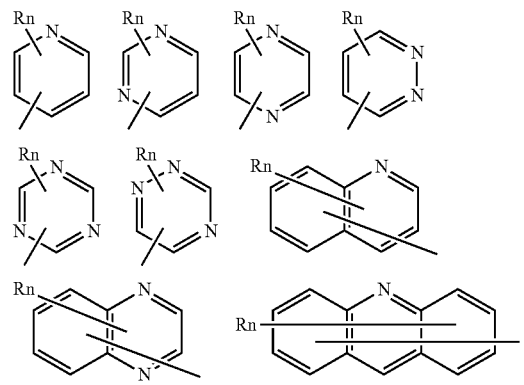

-continued

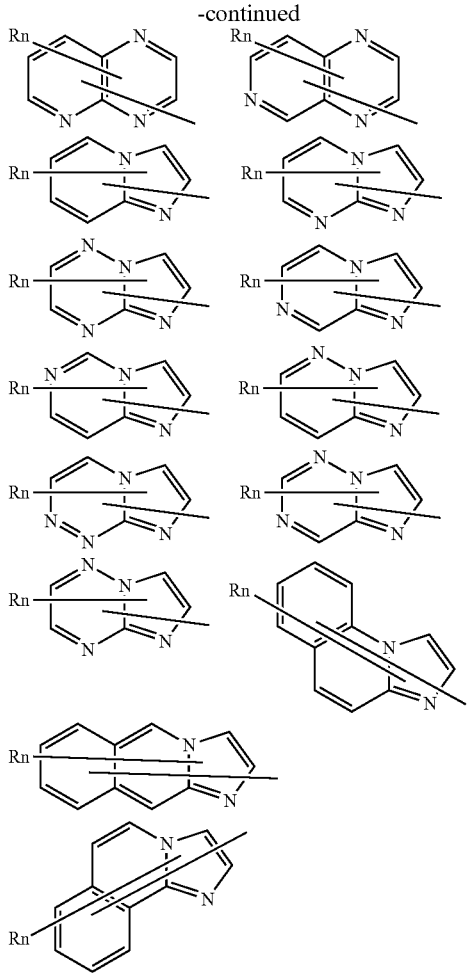

In the above formulae, R is an aromatic hydrocarbon group or a condensed aromatic hydrocarbon group each having 6 to 40 carbon atoms, an aromatic heterocyclic group or a condensed aromatic heterocyclic group each having 3 to 40 carbon atoms, an alkyl group having 1 to 20 carbon atoms, or an alkoxy group having 1 to 20 carbon atoms; and n is an integer of 0 to 5. If n is an integer of 2 or more, R groups may be the same or different.

More preferred is a nitrogen-containing heterocyclic derivative represented by the following formula:

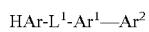

wherein HAr is a substitute or unsubstituted nitrogen-containing heterocyclic group having 3 to 40 carbon atoms; $L^1$ is a single bond, a substituted or unsubstituted aromatic hydrocarbon group or condensed aromatic hydrocarbon group each having 6 to 40 carbon atoms, or a substituted or unsubstituted aromatic heterocyclic group or condensed aromatic heterocyclic group each having 3 to 40 carbon atoms; $Ar^1$ is a substitute or unsubstituted divalent aromatic hydrocarbon group having 6 to 40 carbon atoms; and $Ar^2$ is a substitute or unsubstituted aromatic hydrocarbon group or condensed aromatic hydrocarbon group each having 6 to 40 carbon atoms or a substituted or unsubstituted aromatic heterocyclic group or condensed aromatic heterocyclic group each having 3 to 40 carbon atoms.

HAr is selected, for example, from the following groups:

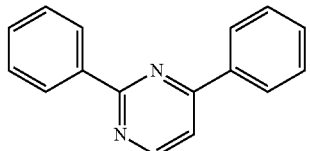

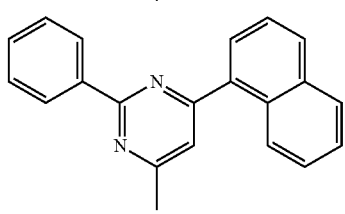

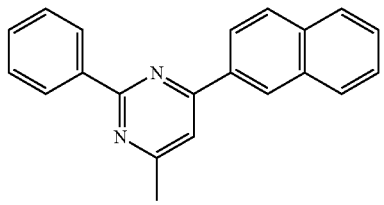

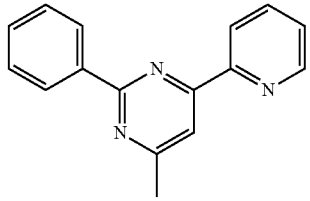

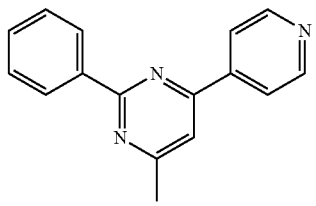

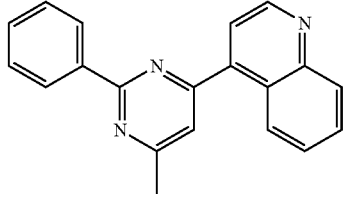

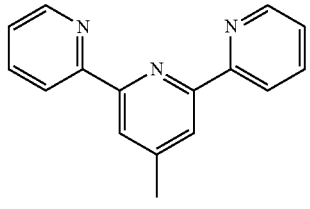

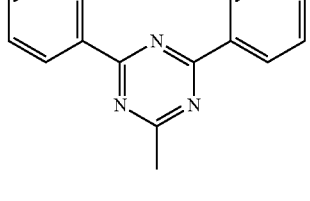

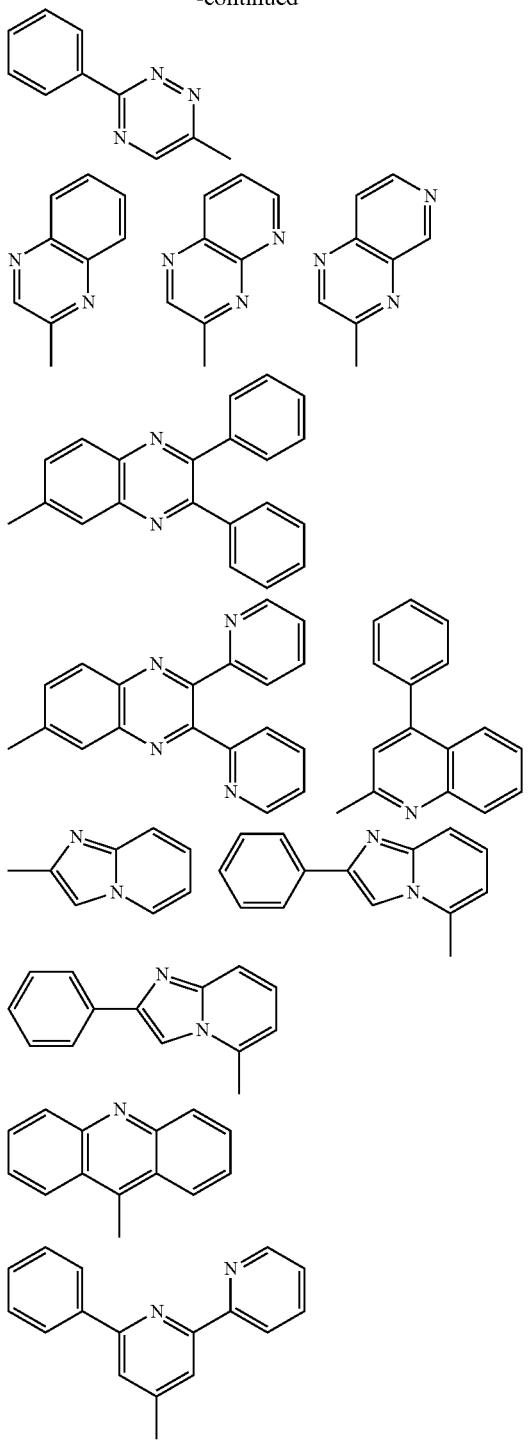

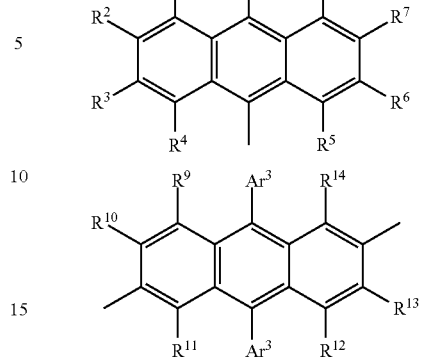

In the above formulae, $R^1$ to $R^{14}$ are each independently a hydrogen atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or condensed aromatic hydrocarbon group each having 6 to 40 carbon atoms, or a substituted or unsubstituted aromatic heterocyclic group or condensed aromatic heterocyclic group each having 3 to 40 carbon atoms; and $Ar^3$ is a substituted or unsubstituted aromatic hydrocarbon group or condensed aromatic hydrocarbon group each having 6 to 40 carbon atoms or a substituted or unsubstituted aromatic heterocyclic group or condensed aromatic heterocyclic group each having 3 to 40 carbon atoms. $R^1$ to $R^8$ may be all hydrogen atoms.

$Ar^2$ is selected, for example, from the following groups:

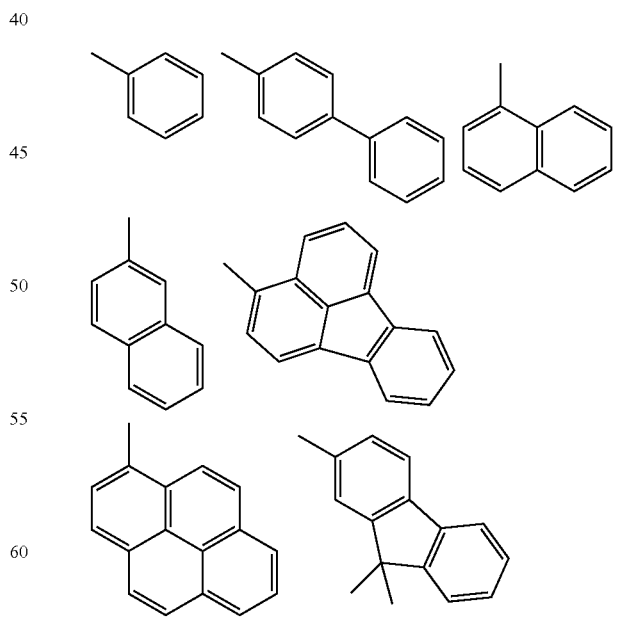

$L^1$ is selected, for example, from the following groups:

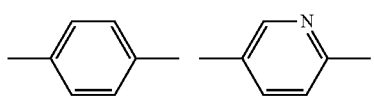

$Ar^1$ is selected, for example, from the following arylanthranyl groups:

In addition, the nitrogen-containing aromatic polycyclic compound for use as the electron transporting compound further includes the following compound:

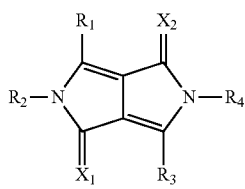

wherein $R_1$ to $R_4$ each independently represent a hydrogen atom, a substituted or unsubstituted aliphatic group having 1 to 20 carbon atoms, a substituted or unsubstituted alicyclic group having 3 to 20 carbon atoms, a substituted or unsubstituted aromatic group having 6 to 50 carbon atoms, or a substituted or unsubstituted heterocyclic group having 3 to 50 carbon atoms; and $X_1$ and $X_2$ each independently represent an oxygen atom, a sulfur atom, or dicyanomethylene group.

Further, the following compound is also suitable as the electron transporting compound:

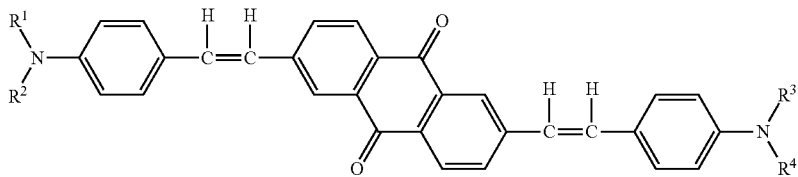

wherein $R^1$, $R^2$, $R^3$, and $R^4$ may be the same or different and each represents an aromatic hydrocarbon group or a condensed aromatic hydrocarbon group each represented by the following formula:

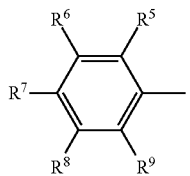

wherein $R^5$, $R^6$, $R^7$, $R^8$, and $R^9$ may be the same or different and each represents a hydrogen atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms. At least one of $R^5$, $R^6$, $R^7$, $R^8$, and $R^9$ is a group other than a hydrogen atom.

Further, a polymer having the nitrogen-containing heterocyclic group or the nitrogen-containing heterocyclic derivative is also usable as the electron transporting compound.

It is particularly preferred for the electron transporting layer of the organic EL of the invention to contain at least one of the nitrogen-containing heterocyclic derivatives represented by the following formulae (60) to (62).

(60)

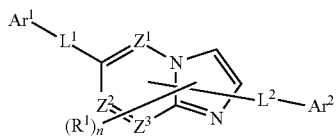

(61)

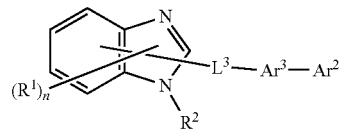

(62)

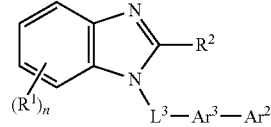

In the formulae (60) to (62), $Z^1$, $Z^2$, and $Z^3$ each independently represent a nitrogen atom or a carbon atom.

$R^1$ and $R^2$ each independently represent a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxyl group having 1 to 20 carbon atoms.

The subscript n is an integer of 0 to 5. If n is an integer of 2 or more, $R^1$ groups may be the same or different from each other. The adjacent two $R^1$ groups may bond to each other to form a substituted or unsubstituted hydrocarbon ring.

$Ar^1$ represents a substituted or unsubstituted aryl group having 6 to 50 ring carbon atoms or a substituted or unsubstituted heteroaryl group having 5 to 50 ring atoms.

$Ar^2$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxyl group having 1 to 20 carbon atoms, a substituted or unsubstituted aryl group having 6 to 50 ring carbon atoms, or a substituted or unsubstituted heteroaryl group having 5 to 50 ring atoms.

However, one of $Ar^1$ and $Ar^2$ is a substituted or unsubstituted condensed aromatic hydrocarbon group having 10 to 50 ring carbon atoms or a substituted or unsubstituted condensed aromatic heterocyclic group having 9 to 50 ring atoms.

$Ar^3$ represents a substituted or unsubstituted arylene group having 6 to 50 ring carbon atoms or a substituted or unsubstituted heteroarylene group having 5 to 50 ring atoms.

$L^1$, $L^2$, and $L^3$ each independently represent a single bond, a substituted or unsubstituted arylene group having 6 to 50 ring carbon atoms or a substituted or unsubstituted divalent condensed aromatic heterocyclic group having 9 to 50 ring atoms.

Examples of the aryl group having 6 to 50 ring carbon atoms include phenyl group, naphthyl group, anthryl group, phenanthryl group, naphthacenyl group, chrysenyl group, pyrenyl group, biphenyl group, terphenyl group, tolyl group, fluoranthenyl group, and fluorenyl group.

Examples of the heteroaryl group having 5 to 50 ring atoms include pyrrolyl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group, triazolyl group, pyrazinyl group, pyridazinyl group, triazinyl group, quinoxalinyl group, acridinyl group, imidazo[1,2-a]pyridinyl group, and imidazo[1,2-a]pyrimidinyl.

Examples of the alkyl group having 1 to 20 carbon atoms include methyl group, ethyl group, propyl group, butyl group, pentyl group, and hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxyl group having 1 to 20 carbon atoms include the alkyl group mentioned above.

Examples of the arylene group having 6 to 50 ring carbon atoms include the groups obtained by removing one hydrogen atom from the aryl group mentioned above.

Examples of the divalent condensed aromatic heterocyclic group having 9 to 50 ring atoms include the groups obtained by removing one hydrogen atom from the condensed aromatic heterocyclic group mentioned above as the heteroaryl group.

The thickness of the electron transporting layer is preferably 1 to 100 nm, although not particularly limited thereto.

The electron injecting layer which may be formed adjacent to the electron transporting layer preferably comprises an inorganic compound, such as an insulating material and a semiconductor, in addition to the nitrogen-containing ring derivative. The insulating material or semiconductor incorporated into the electron injecting layer effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. incorporated into the electron injecting layer further enhances the electron injecting properties. Preferred examples of the alkali metal chalcogenides include $Li_2O$, $K_2O$, $Na_2S$, $Na_2Se$ and $Na_2O$, and preferred examples of the alkaline earth metal chalcogenides include CaO, BaO, SrO, BeO, BaS and CaSe. Preferred examples of the alkali metal halides include LiF, NaF, KF, LiCl, KCl and NaCl. Examples of the alkaline earth metal halides include fluorides such as $CaF_2$, $BaF_2$, $SrF_2$, $MgF_2$ and $BeF_2$ and halides other than fluorides.

Examples of the semiconductor may include oxide, nitride or oxynitride each containing at least one element selected from the group consisting of Ba, Ca, Sr, Yb, Al, Ga, In, Li, Na, Cd, Mg, Si, Ta, Sb and Zn. The semiconductor may be used singly or in combination of two or more. The inorganic compound forming the electron injecting layer preferably forms a microcrystalline or amorphous insulating thin film. When the electron injecting layer is formed from such an insulating thin film, the thin film is made more uniform to decrease the pixel defects such as dark spots. Examples of such inorganic compound include alkali metal chalcogenides, alkali metal halides and alkaline earth metal halide, each being described above.

The thickness of the layer including the insulating material or the semiconductor is preferably about 0.1 to 15 nm. The electron injecting layer may be included with the electron-donating dopant described above.

Hole Transporting Layer

The hole transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit.

An aromatic amine compound, for example, the aromatic amine derivative represented by formula (I), is also preferably used as the material for forming the hole transporting layer.

In the formula (I), each of $Ar^1$ to $Ar^4$ represents a substituted or unsubstituted aromatic hydrocarbon group or condensed aromatic hydrocarbon group having 6 to 50 ring carbon atoms, a substituted or unsubstituted aromatic heterocyclic group or condensed aromatic heterocyclic group having 5 to 50 ring atoms, or a group wherein the aromatic hydrocarbon group or condensed aromatic hydrocarbon group and the aromatic heterocyclic group or condensed aromatic heterocyclic group are boned to each other.

L represents a substituted or unsubstituted aromatic hydrocarbon group or condensed aromatic hydrocarbon group each having 6 to 50 ring carbon atoms or a substituted or unsubstituted aromatic heterocyclic group or condensed aromatic heterocyclic group each having 5 to 50 ring atoms.

Specific examples of the compound represented by the formula (I) are shown below.

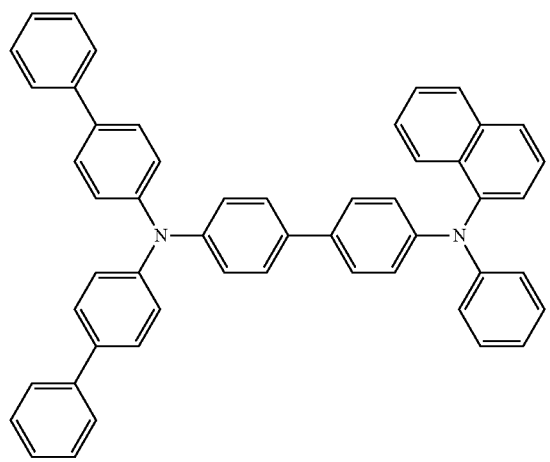

109
-continued
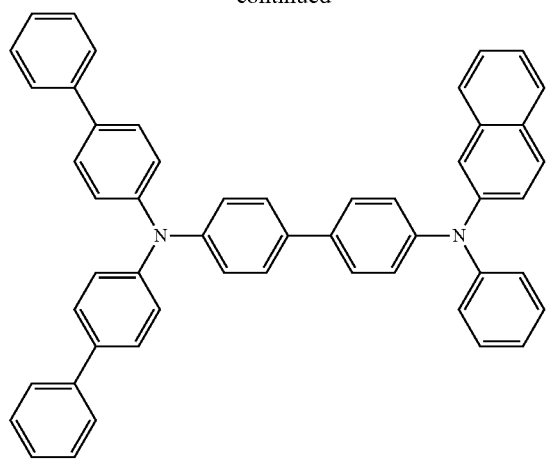
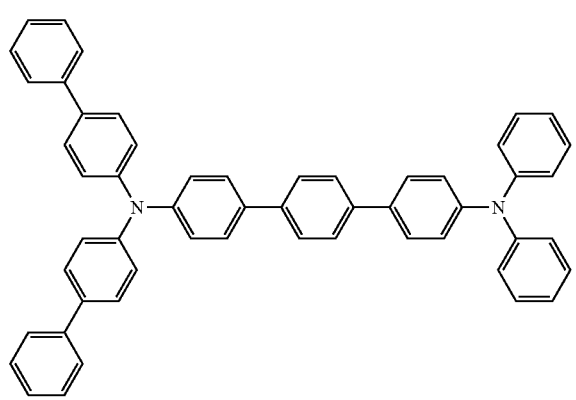
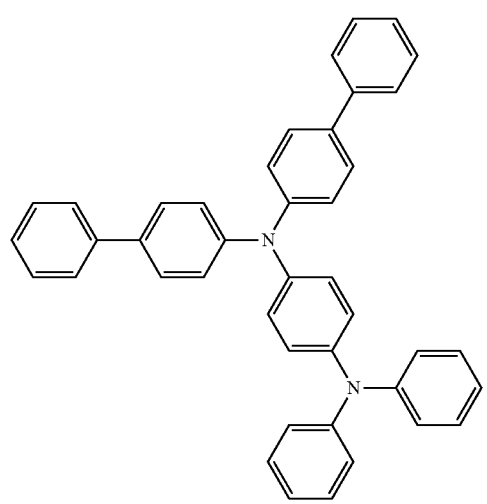
110
-continued
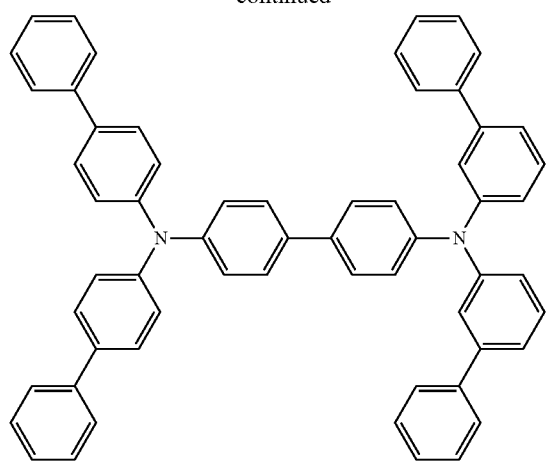
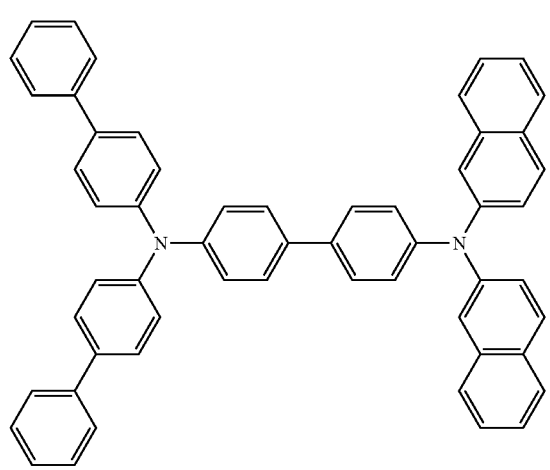
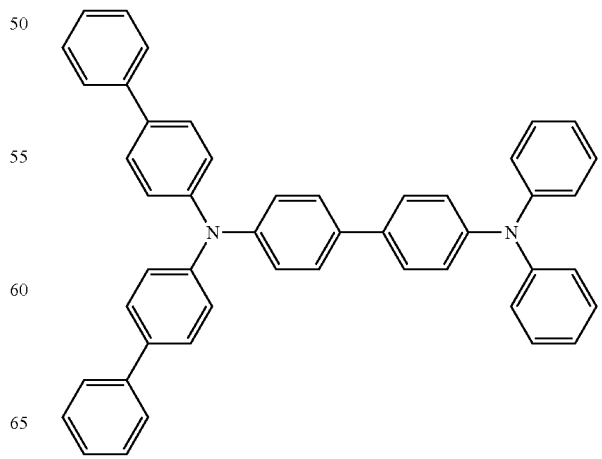

111
-continued
112
-continued
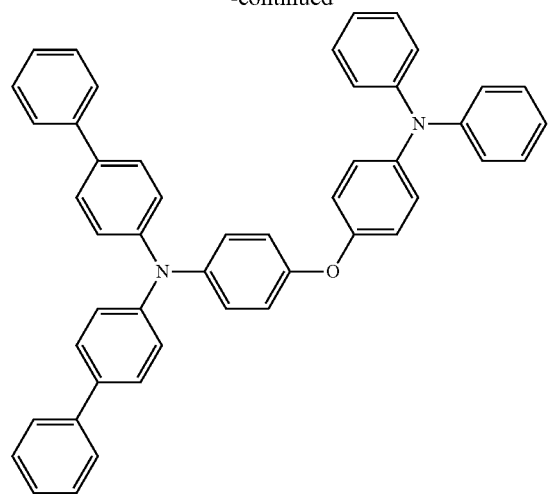
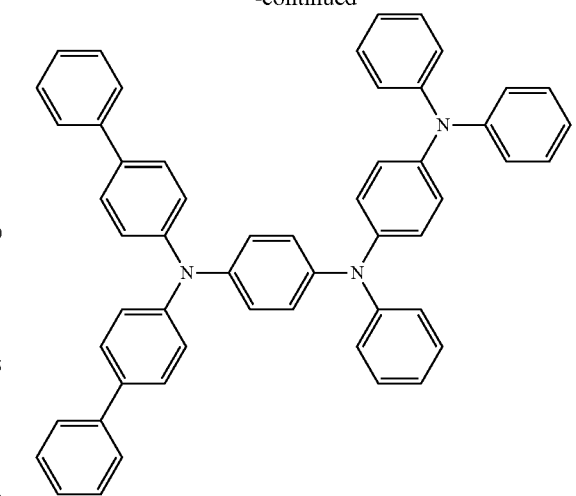
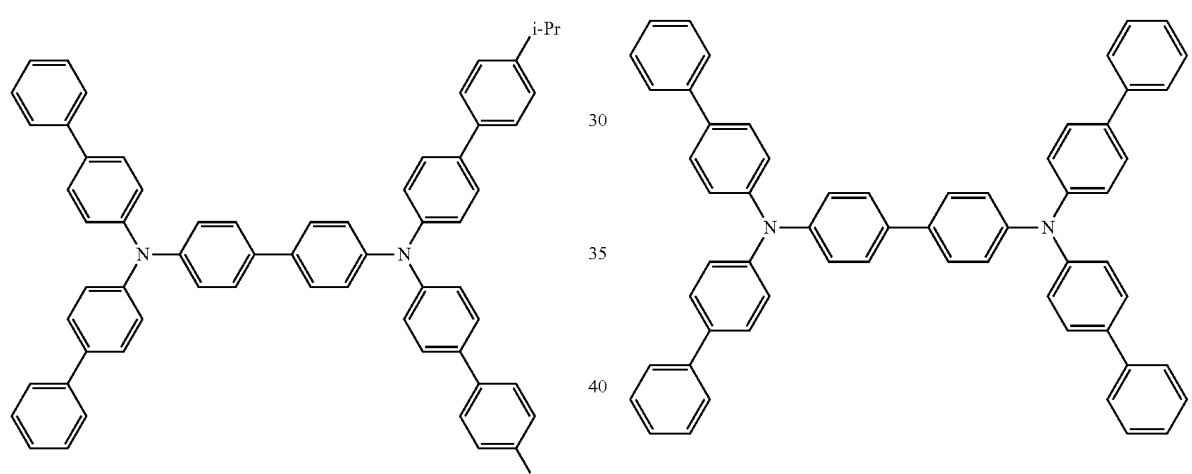
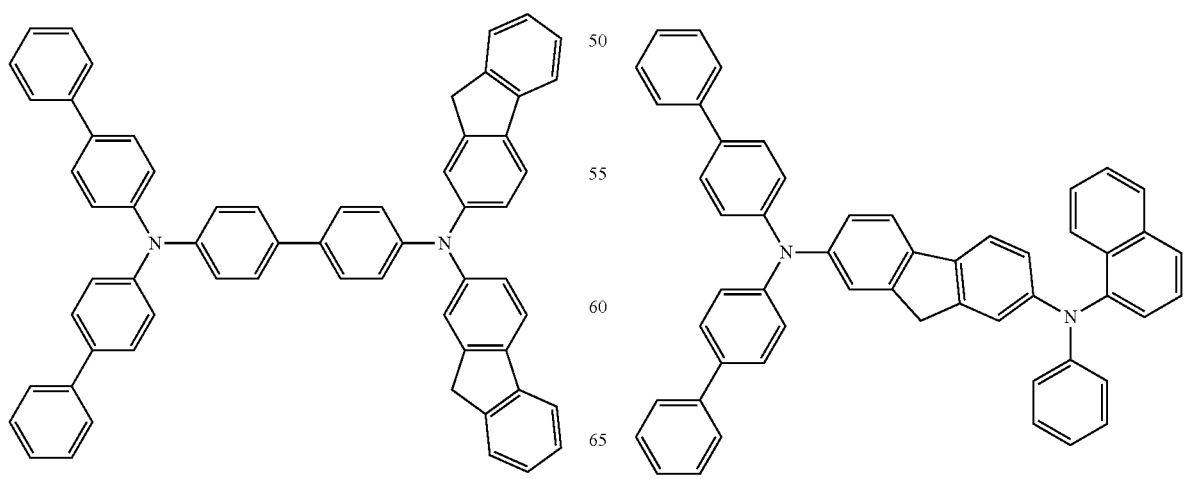

113
-continued
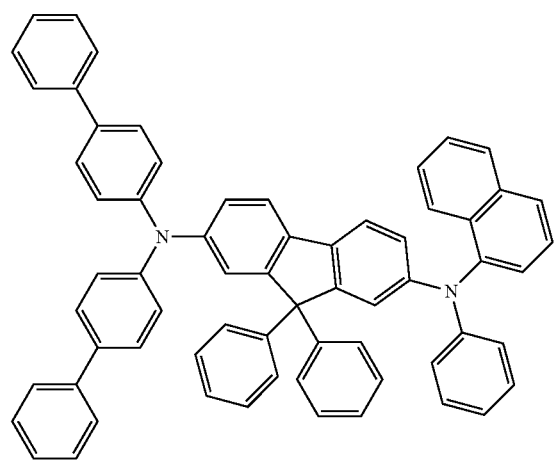
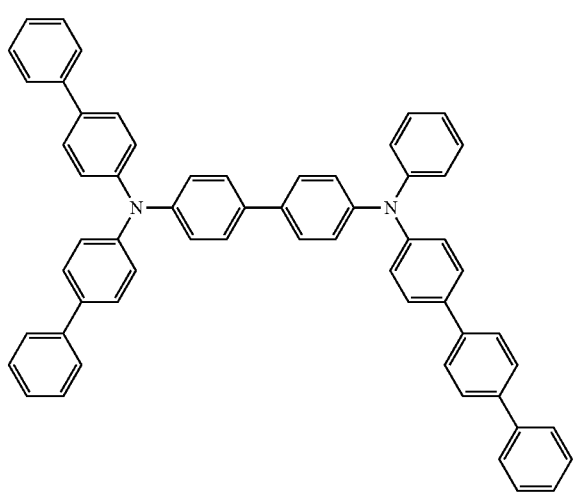
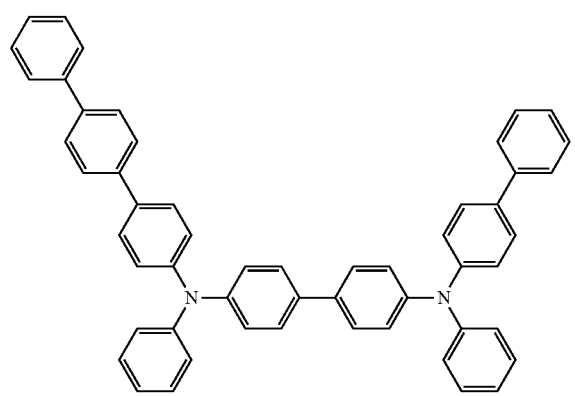
114
-continued
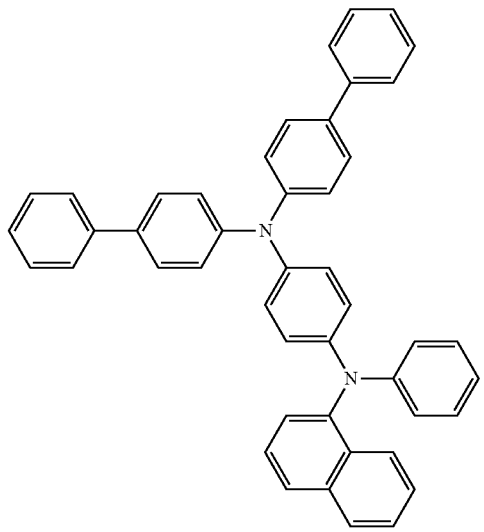
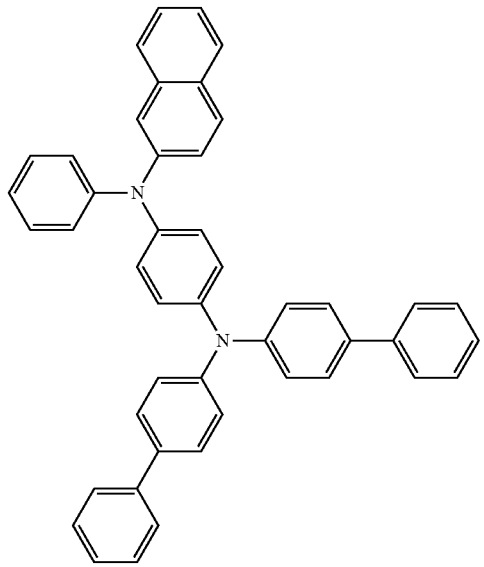
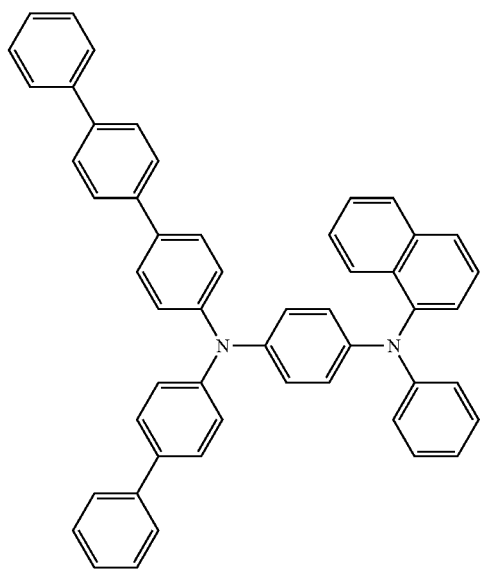

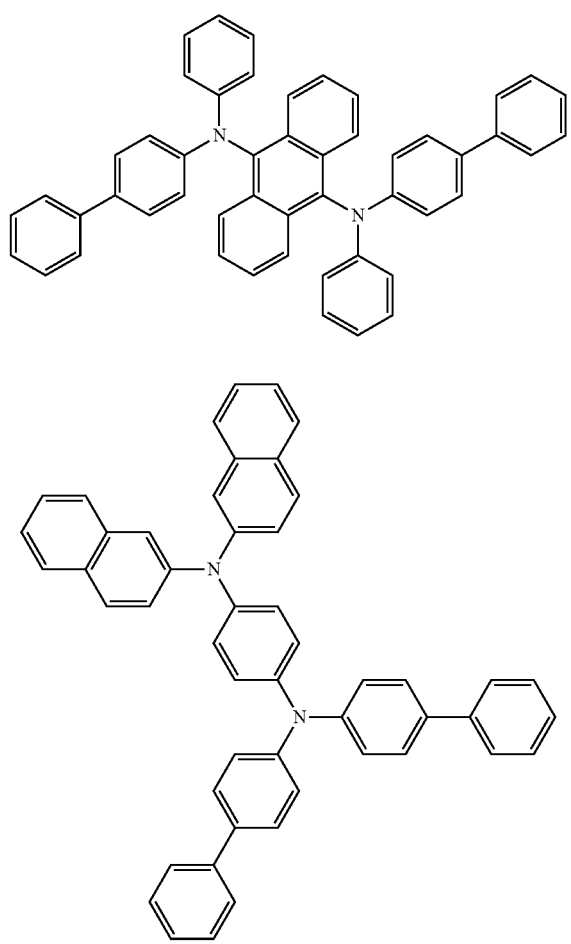
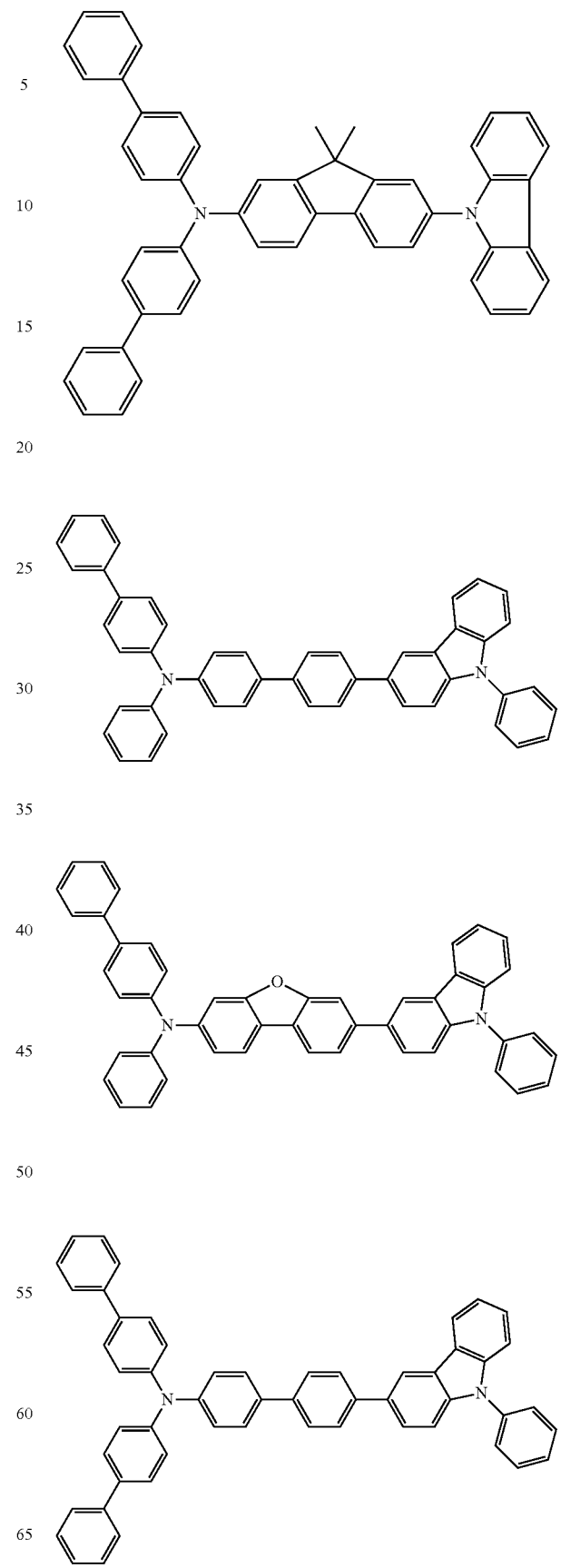

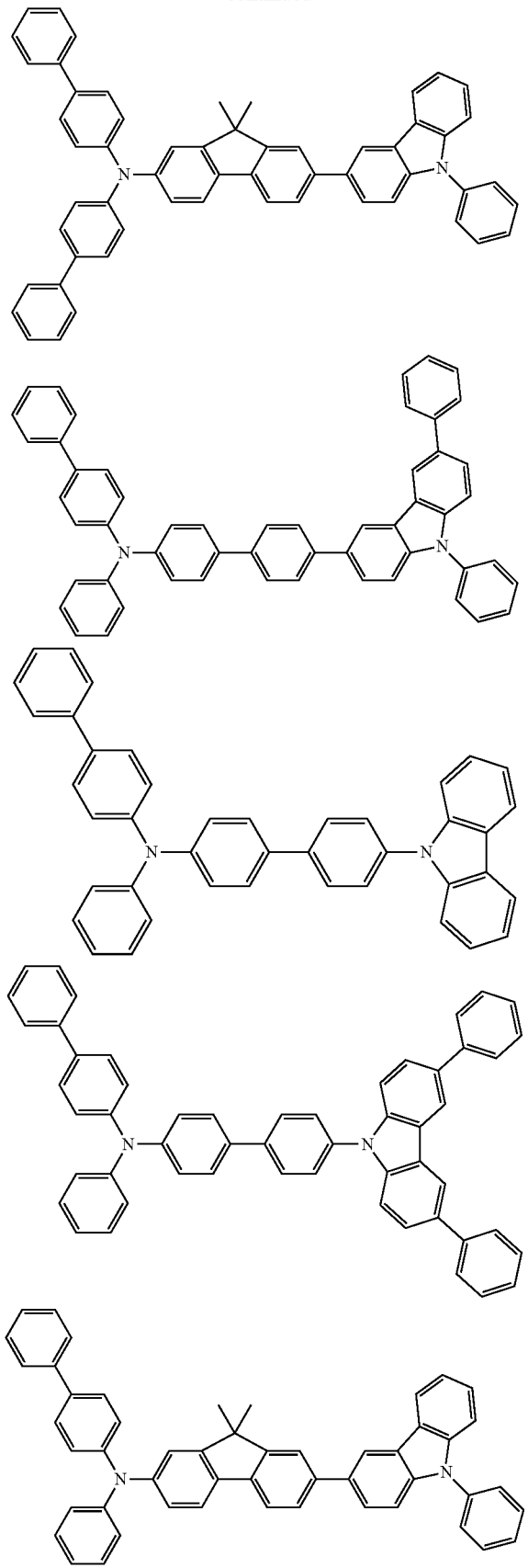

The aromatic amine represented by the formula (II) is also preferably used as the material for forming the hole transporting layer.

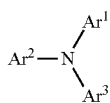  (II)

In the formula (II), each of $Ar^1$ to $Ar^3$ is defined in the same manner as in the definition of $Ar^1$ to $Ar^4$ of the formula (I). The specific examples of the compounds represented by the formula (II) are shown below, although not limited thereto.

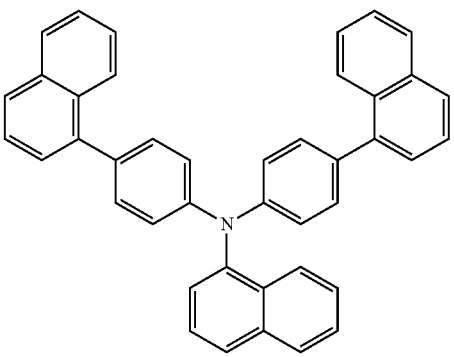
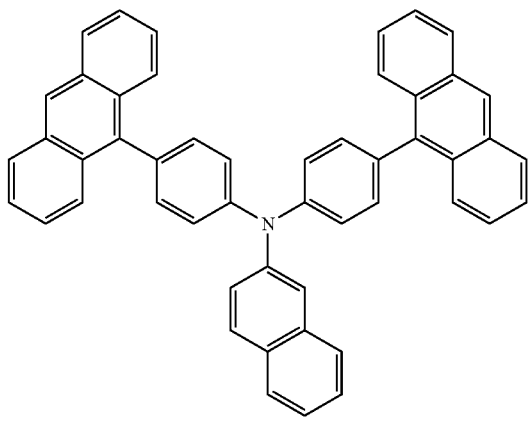
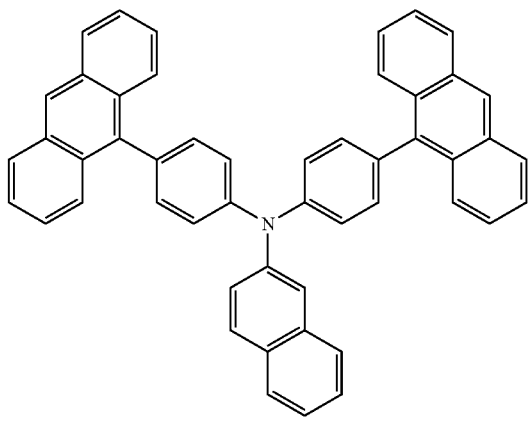
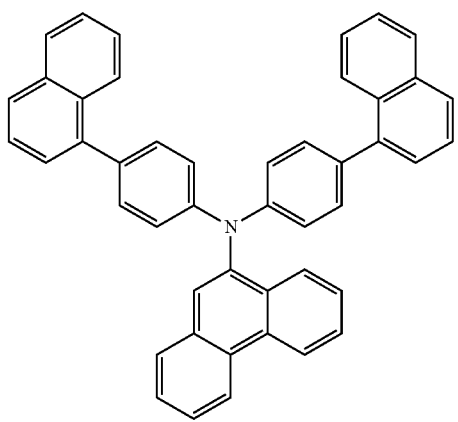

119
-continued
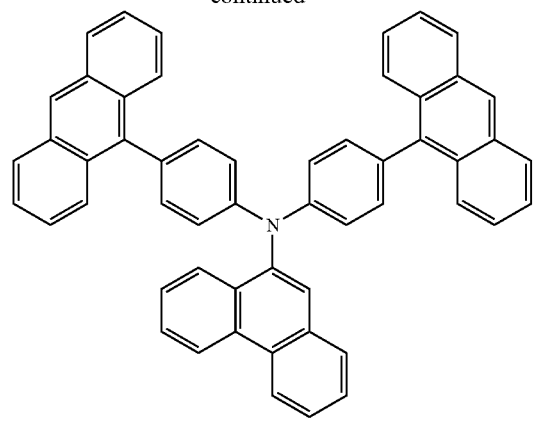
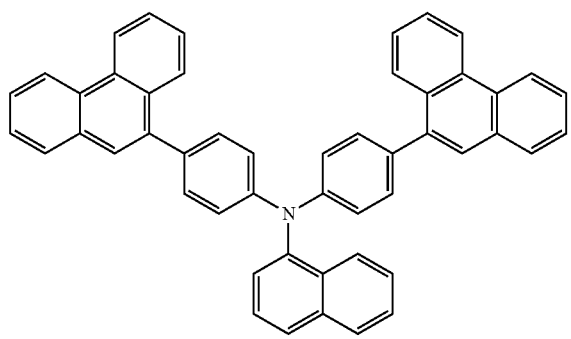
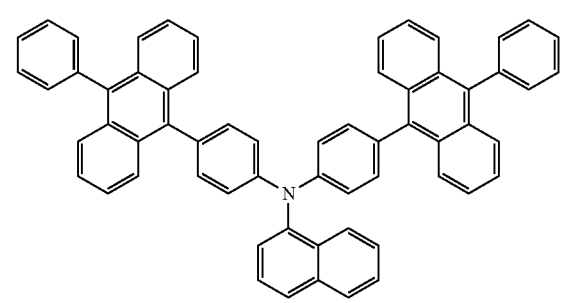
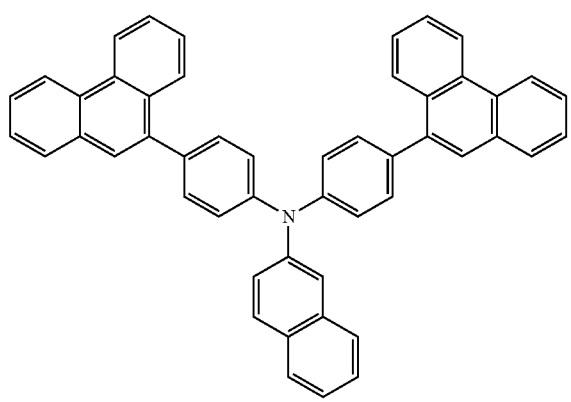
120
-continued
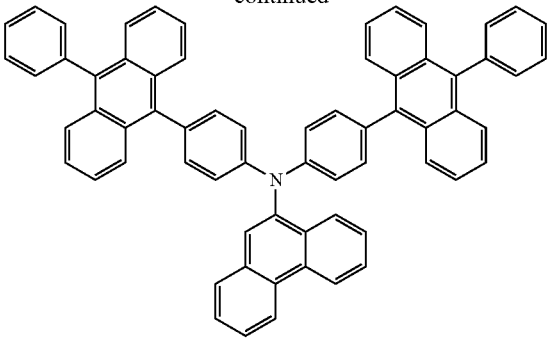
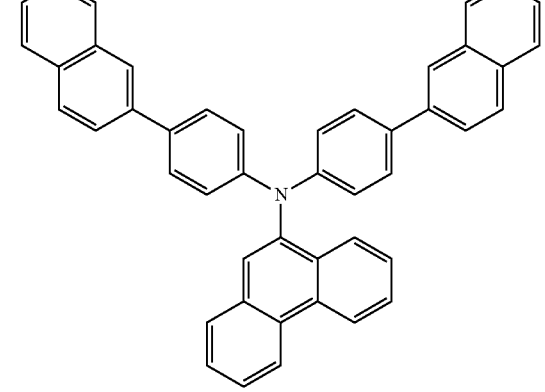
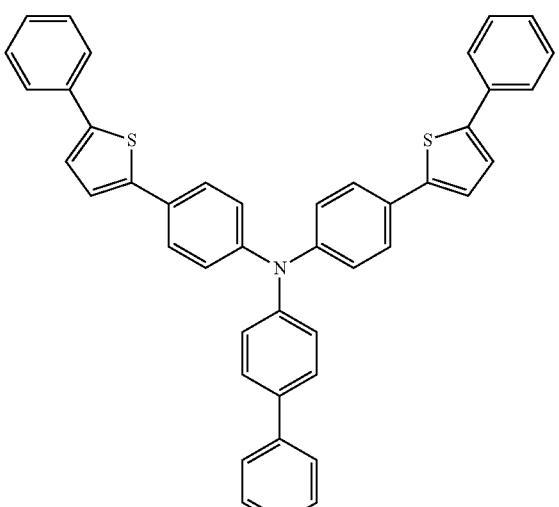
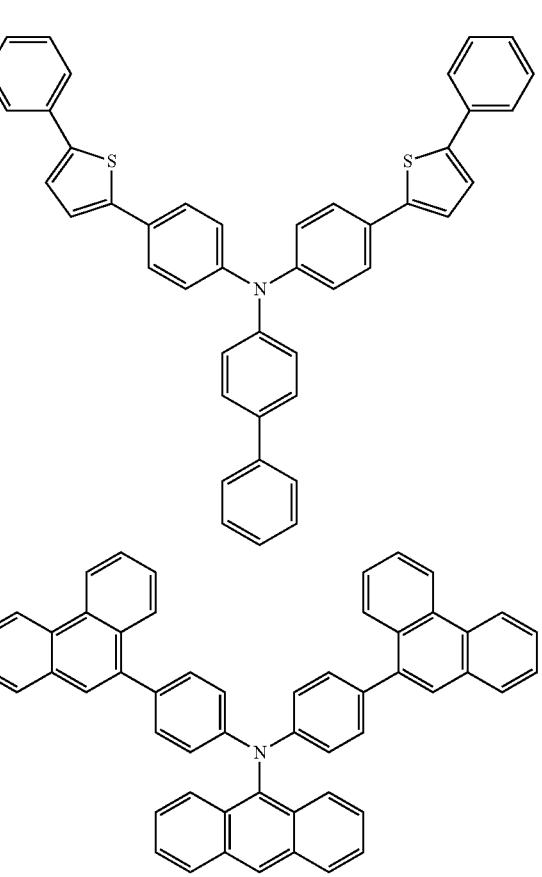

121
-continued

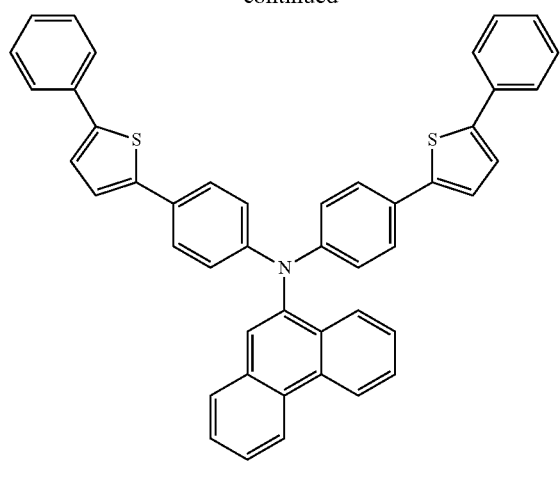

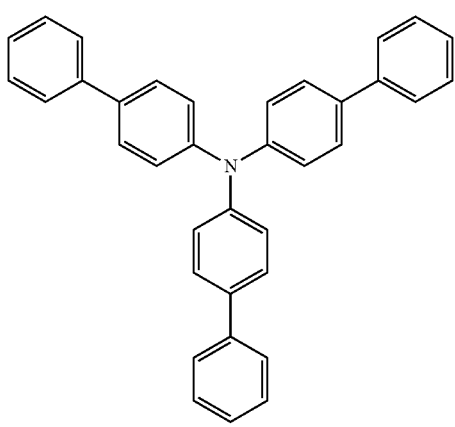

122
-continued

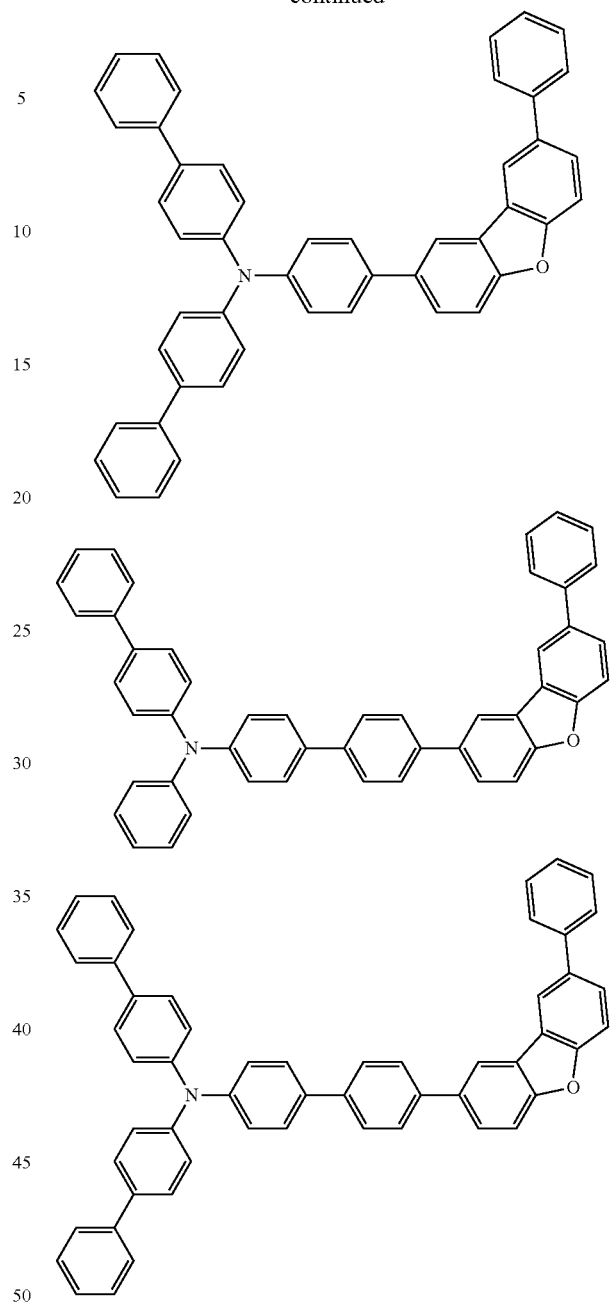

The hole transporting layer of the organic EL device of the invention may be made into two-layered structure of a first hole transporting layer (anode side) and a second hole transporting layer (cathode side).

The thickness of the hole transporting layer is preferably 10 to 200 nm, although not particularly limited thereto.

The organic EL device of the invention may have a layer comprising an electron accepting compound which is attached to the anode side of each of the hole transporting layer and the first hole transporting layer. With such a layer, it is expected that the driving voltage is lowered and the production cost is reduced.

The electron accepting compound is preferably a compound represented by formula (A):

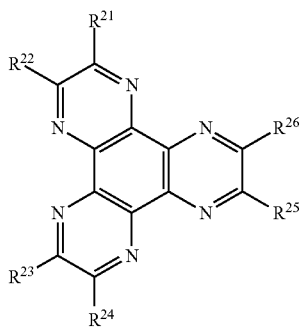

(A)

wherein $R^{21}$ to $R^{26}$ may be the same or different and each independently represent a cyano group, —$CONH_2$, a carboxyl group, or —$COOR^{27}$ wherein $R^{27}$ represents an alkyl group having 1 to 20 carbon atoms or a cycloalkyl group having 3 to 20 carbon atoms. One or more of a pair of $R^{21}$ and $R^{22}$, a pair of $R^{23}$ and $R^{24}$, and a pair of $R^{25}$ and $R^{26}$ may bond to each other to form a group represented by —CO—O—CO—.

Examples of $R^{27}$ include methyl group, ethyl group, n-propyl group, isopropyl group, n-butyl group, isobutyl group, t-butyl group, cyclopentyl group, and cyclohexyl group.

The thickness of the layer comprising the electron accepting compound is preferably 5 to 20 nm, although not particularly limited thereto.

N/P Doping

The carrier injecting properties of the hole transporting layer and the electron transporting layer can be controlled by, as described in JP 3695714B, the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4TCNQ$.

Space Layer

For example, in an organic EL device wherein a fluorescent light emitting layer and a phosphorescent light emitting layer are laminated, a space layer is disposed between the fluorescent light emitting layer and the phosphorescent light emitting layer to prevent the diffusion of excitons generated in the phosphorescent light emitting layer to the fluorescent light emitting layer or to control the carrier balance. The space layer may be disposed between two or more phosphorescent light emitting layers.

Since the space layer is disposed between the light emitting layers, a material combining the electron transporting ability and the hole transporting ability is preferably used for forming the space layer. To prevent the diffusion of triplet energy in the adjacent phosphorescent light emitting layer, the triplet energy of the material for the space layer is preferably 2.6 eV or more. The materials described with respect to the hole transporting layer are usable as the material for the space layer.

Blocking Layer

The organic EL device of the invention preferably has a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer.

The triplet blocking layer, as mentioned below, prevents the diffusion of triplet excitons generated in the light emitting layer to adjacent layers and has a function of confining the triplet excitons in the light emitting layer, thereby preventing the deactivation of energy on molecules other than the emitting dopant of triplet excitons, for example, on molecules in the electron transporting layer.

If a device having a triplet blocking layer satisfies the following energy relationship:

$$E^T_d < E^T_{TB}$$

wherein $E^T_d$ is the triplet energy of the phosphorescent dopant in the light emitting layer and $E^T_{TB}$ is the triplet energy of the compound forming the triplet blocking layer, the triplet excitons of phosphorescent dopant are confined (not diffuse to other molecules). Therefore, the energy deactivation process other than the emission on the phosphorescent dopant may be prevented to cause the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of ambient heat energy when driving a device at around room temperature as generally employed in practical drive of device. As compared with the fluorescent emission, the phosphorescent emission is relatively likely to be affected by the diffusion of excitons due to the heat absorption because the lifetime of triplet excitons is longer. Therefore, as for the energy difference $\Delta E^T$, the larger as compared with the heat energy of room temperature, the better. The energy difference $\Delta E^T$ is more preferably 0.1 eV or more and particularly preferably 0.2 eV or more.

The triplet energy referred to herein was determined as follows.

A sample was dissolved in EPA solvent (diethyl ether:isopentane:ethanol=5:5:2 (by volume)) in a concentration of 10 μmol/L to prepare a specimen for phosphorescence measurement. The specimen for phosphorescence measurement was placed in a quartz cell and irradiated with excitation ray at 77 K, and the emitted phosphorescence was measured. Using the measured result, the triplet energy was determined as the value calculated from the following conversion formula:

$$E^T(eV) = 1239.85/\lambda_{edge}$$

wherein $\lambda_{edge}$ is determined as follows.

On the phosphorescence spectrum with a vertical axis of phosphorescent intensity and a horizontal axis of wavelength, a line tangent to the rising portion at the short-wavelength side of the phosphorescent spectrum was drawn, and the wavelength (nm) at the intersection of the tangent line and the horizontal axis was expressed by "$\lambda_{edge}$."

A material satisfying the following relationship:

$$A_b - A_h \leq 0.1 \text{ eV}$$

wherein $A_b$ is the affinity of the blocking layer material and $A_h$ is the affinity of the host material in the light emitting layer, is preferably used as the host material in the light emitting layer.

The electron affinity is defined as the amount of energy released or absorbed when one electron is added to a molecule. The affinity level is expressed by a positive sign when the energy is released and a negative sign when the energy is absorbed. Using the ionization potential Ip and the optical energy gap Eg(S), the affinity Af is expressed by:

$Af=Ip-Eg(S)$.

The ionization potential Ip is the amount of energy required to remove an electron from a compound to ionize the compound. In the present invention, Ip is a positive value measured by a photoelectronic spectrophotometer (AC-3, manufactured by Riken Keiki Co., Ltd.) in the atmosphere. The optical energy gap Eg(S) is the difference between the conduction level and the valence level. In the present invention, Eg(S) is a positive value which is determined by measuring an ultraviolet/visible absorption spectrum of a diluted dichloromethane solution of a material, drawing a line tangent to the spectrum at the long-wavelength side, and converting the wavelength of the intersection between the tangent line and the base line (zero absorption) to the unit of energy.

The electron mobility of the material for the triplet blocking layer is preferably $10^{-6}$ cm$^2$/Vs or more at an electric field strength in a range of 0.04 to 0.5 MV/cm. There are several methods for measuring the electron mobility of organic material, for example, Time of Flight method. In the present invention, the electron mobility is determined by impedance spectroscopy.

The electron mobility of the electron injecting layer is preferably $10^{-6}$ cm$^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

EXAMPLES

The present invention will be described in more detail with reference to the examples. However, it should be noted that the scope of the invention is not limited to the following examples.

Intermediate Synthesis 1-1: Synthesis of Intermediate 1-1

In an argon atmosphere, 23 g (90.6 mmol) of iodine, 9.4 g (41.2 mmol) of periodic acid dihydrate, 42 ml of water, 360 ml of acetic acid, and 11 ml of sulfuric acid were added to 55 g (201.3 mmol) of 2-bromo-9,9-dimethylfluorene, and the resultant mixture was stirred at 65° C. for 30 min and further stirred at 90° C. for 6 h.

After the reaction, the reaction product was poured into iced water. The precipitated crystals were collected by filtration and washed with water and then with methanol, to obtain 61 g of a white solid, which was identified as the following intermediate 1-1 by FD-MS analysis (yield: 76%).

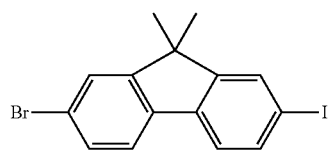

Intermediate 1-1

Intermediate Synthesis 1-2: Synthesis of Intermediate 1-2

In a nitrogen atmosphere, 150 g (0.89 mol) of dibenzofuran was dissolved in 1000 ml of acetic acid under heating. After adding 188 g (1.18 mol) of bromine dropwise, the resultant mixture was stirred at room temperature for 20 h. The precipitated crystals were collected by filtration and successively washed with acetic acid and water. The crude product was recrystallized from methanol several times, to obtain 66.8 g of a white crystal, which was identified as the following intermediate 1-2 by FD-MS analysis (yield: 30%).

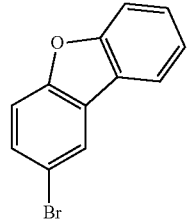

Intermediate 1-2

Intermediate Synthesis 1-3: Synthesis of Intermediate 1-3

In an argon atmosphere, 400 ml of dehydrated THF was added to 24.7 g (100.0 mmol) of intermediate 1-2, and the resultant mixture was cooled to −40° C. Then 63 ml (100.0 mmol) of a 1.6 M hexane solution of n-butyllithium was gradually added. After stirring the reaction solution for one hour while heating to 0° C., the reaction solution was again cooled to −78° C. and added dropwise with 26.0 g (250.0 mmol) of a solution of trimethyl borate in 50 ml of dehydrated THF. After the dropwise addition, the reaction solution was stirred at room temperature for 5 h. After adding 200 ml of a 1 N hydrochloric acid, the stirring was further continued for one hour, and then, the water layer was removed. The organic layer was dried over MgSO$_4$ and the solvent was removed by evaporation under reduced pressure. The obtained solid was washed with toluene, to obtain 15.2 g of a white crystal (yield: 72%).

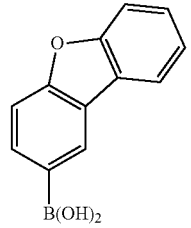

Intermediate 1-3

Intermediate Synthesis 1-4: Synthesis of Intermediate 1-4

In an argon atmosphere, 150 ml of toluene, 150 ml of dimethoxyethane, and 150 ml (300.0 mmol) of a 2 M aqueous solution of Na$_2$CO$_3$ were added to a mixture of 28.3 g (100.0 mmol) of 4-iodobromobenzene, 22.3 g (105.0 mmol) of intermediate 1-3 and 2.31 g (2.00 mmol) of Pd[PPh$_3$]$_4$, and the resultant mixture was stirred for 10 h while refluxing under heating.

After the reaction, the reaction product was extracted with dichloromethane in a separatory funnel. The organic layer was dried over MgSO$_4$, filtered, and then concentrated. The concentrate was purified by silica gel column chromatography, to obtain 24.2 g of a white solid, which was identified as the following intermediate 1-4 by FD-MS analysis (yield: 75%).

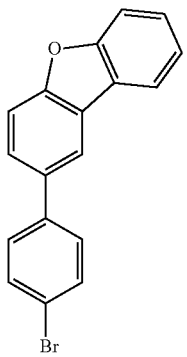

Intermediate 1-4

Intermediate Synthesis 1-5: Synthesis of Intermediate 1-5

In an argon atmosphere, 150 ml of toluene, 150 ml of dimethoxyethane, and 150 ml (300.0 mmol) of a 2 M aqueous solution of $Na_2CO_3$ were added to a mixture of 28.3 g (100.0 mmol) of 4-iodobromobenzene, 22.3 g (105.0 mmol) of dibenzofuran-4-boronic acid and 2.31 g (2.00 mmol) of $Pd[PPh_3]_4$, and the resultant mixture was stirred for 10 h while refluxing under heating.

After the reaction, the reaction product extracted with dichloromethane in a separatory funnel. The organic layer was dried over $MgSO_4$, filtered, and then concentrated. The concentrate was purified by silica gel column chromatography, to obtain 26.2 g of a white solid, which was identified as the following intermediate 1-5 by FD-MS analysis (yield: 81%).

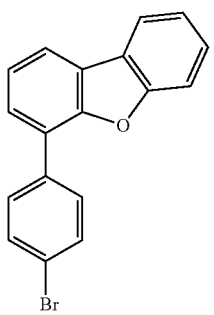

Intermediate 1-5

Intermediate Synthesis 1-6: Synthesis of Intermediate 1-6

The reaction of Intermediate Synthesis 1-5 was repeated except for using 39.9 g of intermediate 1-1 in place of 4-iodobromobenzene, to obtain 35.7 g of a white solid, which was identified as the following intermediate 1-6 by FD-MS analysis (yield: 81%).

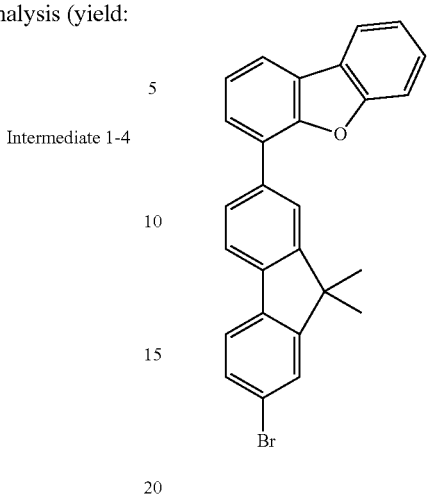

Intermediate 1-6

Intermediate Synthesis 1-7: Synthesis of Intermediate 1-7

Into a mixture of 17.7 g (72.7 mmol) of 9-phenylcarbazole, 6.03 g (36.3 mmol) of potassium iodide and 7.78 g (36.4 mmol) of potassium iodate, 5.9 ml of sulfuric acid and 70 ml of ethanol were added, and the resultant mixture was stirred at 75° C. for 2 h. After cooling, the reaction production was added with water and ethyl acetate and liquid-liquid extracted. The organic layer was washed with an aqueous solution of sodium hydrogencarbonate and water and then concentrated. The obtained crude product was purified by silica gel column chromatography, to obtain 21.8 g of a white solid, which was identified as the following intermediate 1-7 by FD-MS analysis (yield: 81%).

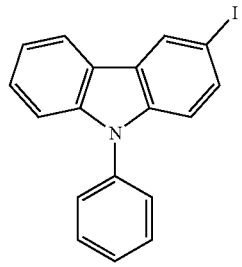

Intermediate 1-7

Intermediate Synthesis 1-8: Synthesis of Intermediate 1-8

In an argon atmosphere, 50 ml of dehydrated toluene and 50 ml of dehydrated ether were added to 13.1 g (35.5 mmol) of intermediate 1-7, and the resultant mixture was cooled to −45° C. The mixture was further added with 25 ml (39.5 mmol) of a 1.58 M hexane solution of n-butyllithium and heated to −5° C. over one hour under stirring. The mixture was again cooled to −45° C. and added with 25 ml (109.0 mmol) of triisopropyl borate dropwise to allow the reaction to proceed for 2 h.

After returning to room temperature, the reaction product was added with a 10% diluted hydrochloric acid and stirred for extraction. The organic layer was washed with a saturated saline solution, dried over $MgSO_4$, and filtered. The filtrate was concentrated, and the concentrate was purified by silica gel column chromatography. The obtained solid was washed with n-hexane, to obtain 7.1 g of a white solid (yield: 70%).

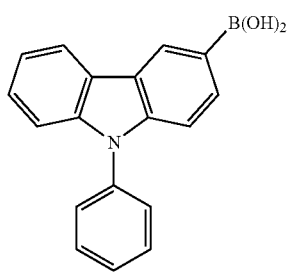

Intermediate 1-8

Intermediate Synthesis 1-9: Synthesis of Intermediate 1-9

In an argon atmosphere, 600 ml of dehydrated tetrahydrofuran was added to 78.0 g (0.46 mol) of dibenzofuran. The resultant mixture was cooled to −30° C. and added with 300 ml (0.50 mol) of a 1.65 M hexane solution of n-butyllithium dropwise, and then, the temperature was raised to room temperature over one hour under stirring. After further stirring at room temperature for 5 h, the mixture was cooled to −60° C. and added with 60 ml (0.70 mol) of 1,2-dibromoethane dropwise over one hour.

After further stirring at room temperature for 15 h, the mixture was poured into 1000 ml of iced water and then extracted with dichloromethane. The organic layer was washed with a saturated saline solution, dried over MgSO₄, filtered, and then concentrated. The concentrate was purified by silica gel chromatography and washed with tetrahydrofuran/methanol, to obtain 70 g of solid, which was identified as the following intermediate 1-9 by FD-MS analysis (yield: 62%).

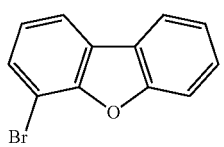

Intermediate 1-9

Intermediate Synthesis 2-1: Synthesis of Intermediate 2-1

In an argon atmosphere, 90 ml of dehydrated 1,4-dioxane was added to a mixture of 15.0 g (58.5 mmol) of indolo[2,3-a]carbazole (synthesized according to the method of Synlett p. 42-48 (2005)), 11.9 g (58.5 mmol) of iodobenzene, 11.2 g (58.5 mmol) of copper iodide, 20.0 g (175.5 mmol) of trans-1,2-cyclohexanediamine, and 37.3 g (175.5 mmol) of tripotassium phosphate, and the resultant mixture was stirred for 24 h while refluxing under heating. The reaction solution was concentrated under reduced pressure. The obtained residue was added with 500 ml of toluene, heated to 120° C., and then filtered to remove insolubles. The filtrate was concentrated under reduced pressure and the obtained residue was purified by silica gel column chromatography, to obtain 10.0 g of white solid, which was identified as the following intermediate 2-1 by FD-MS analysis (yield: 51%).

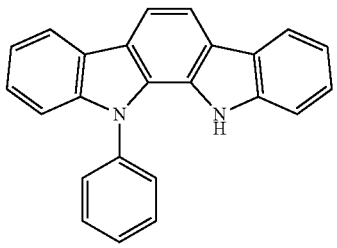

Intermediate 2-1

Intermediate Synthesis 2-2: Synthesis of Intermediate 2-2

A solution of 25.0 g (101.5 mmol) of 3,3-methylenediindole and 15.1 g (101.5 mmol) of triethyl orthoformate in 400 ml of methanol was added with 1.4 ml of concentrated sulfuric acid and stirred for 5 h while refluxing under heating. The reaction solution was cooled in an iced water bath. The precipitate was collected by filtration and washed with 500 ml of methanol, to obtain 19.0 g of brown solid, which was identified as the following intermediate 2-2 by FD-MS analysis (yield: 73%).

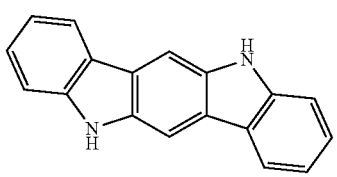

Intermediate 2-2

Intermediate Synthesis 2-3: Synthesis of Intermediate 2-3

In an argon atmosphere, 50 ml of dehydrated 1,4-dioxane was added to a mixture of 5.1 g (20.0 mmol) of intermediate 2-2, 4.1 g (20.0 mmol) of iodobenzene, 3.8 g (20.0 mmol) of copper iodide, 6.9 g (60.0 mmol) of trans-1,2-cyclohexanediamine, and 12.7 g (60.0 mmol) of tripotassium phosphate. The resultant mixture was stirred for 48 h while refluxing under heating. The reaction solution was concentrated under reduced pressure. The obtained residue was added with 1000 ml of toluene, heated to 120° C., and then filtered to remove the insolubles. The filtrate was concentrated under reduced pressure and the obtained residue was purified by silica gel column chromatography, to obtain 1.7 g of brown solid, which was identified as the following intermediate 2-3 by FD-MS analysis (yield: 26%).

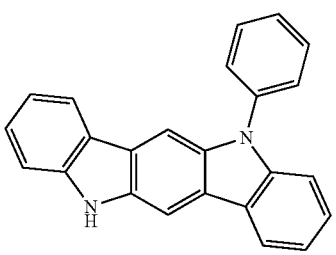

Intermediate 2-3

Intermediate Synthesis 2-4: Synthesis of Intermediate 2-4

In an argon atmosphere, 124 ml (248 mmol) of a 2 M aqueous solution of Na₂CO₃, 250 ml of DME, 250 ml of toluene, and 7.2 g (6.2 mmol) of Pd[PPh₃]₄ were added to a mixture of 25.0 g (123.8 mmol) of 2-bromonitrobenzene, 31.5 g (148.5 mmol) of 4-dibenzofuranboronic acid. The resultant mixture was stirred for 12 h while refluxing under heating.

After the reaction, the mixture was cooled to room temperature. The reaction product was added with 500 ml of water and extracted with dichloromethane in a separatory funnel. The organic layer was dried over $MgSO_4$, filtered, and concentrated. The concentrate was purified by silica gel column chromatography, to obtain 24.0 g of white solid, which was identified as the following intermediate 2-4 by FD-MS analysis (yield: 67%).

Intermediate 2-4

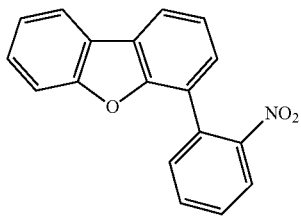

Intermediate Synthesis 2-5: Synthesis of Intermediate 2-5

In an argon atmosphere, 166 ml of dimethylacetamide was added to a mixture of 24.0 g (83.0 mmol) of intermediate 2-4 and 54.4 g (207.4 mmol) of triphenylphosphine. The resultant mixture was stirred for 20 h while refluxing under heating.

After the reaction, the mixture was cooled to room temperature. The reaction product was added with 400 ml of water and extracted with dichloromethane in a separatory funnel. The organic layer was dried over $MgSO_4$, filtered and concentrated. The concentrate was purified by silica gel column chromatography, to obtain 14.5 g of white solid, which was identified as the following intermediate 2-5 by FD-MS analysis (yield: 68%).

Intermediate 2-5

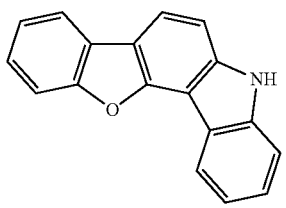

Intermediate Synthesis 2-6: Synthesis of Intermediate 2-6

The reaction of Intermediate Synthesis 2-4 was repeated except for using 33.9 g of 4-dibenzothiopheneboronic acid in place of 4-dibenzofuranboronic acid, to obtain 28.4 g of white powder, which was identified as the following intermediate 2-6 by FD-MS analysis (yield: 75%).

Intermediate 2-6

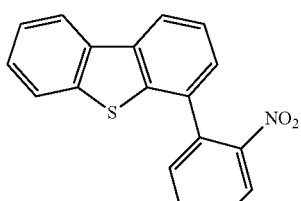

Intermediate Synthesis 2-7: Synthesis of intermediate 2-7

The reaction of Intermediate Synthesis 2-5 was repeated except for using 25.3 g of intermediate 2-6 in place of intermediate 2-4, to obtain 14.7 g of white powder, which was identified as the following intermediate 2-7 by FD-MS analysis (yield: 65%).

Intermediate 2-7

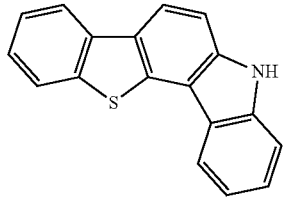

Intermediate Synthesis 2-8: Synthesis of Intermediate 2-8

A solution of 18.7 g (142.0 mmol) of 1-indanone and 20.5 g (142.0 mmol) of phenylhydrazinium chloride in 400 ml of ethanol was added with 2.0 ml of concentrated sulfuric acid. The resultant mixture was stirred for 8 h while refluxing under heating. The reaction solution was allowed to stand for cooling, and then, the precipitate was collected by filtration and washed with 500 ml of methanol. By recrystallizing the crude product, 17.5 g of white solid was obtained, which was identified as the following intermediate 2-8 by FD-MS analysis (yield: 60%).

Intermediate 2-8

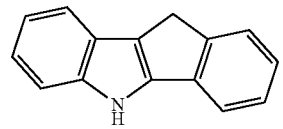

Intermediate Synthesis 2-9: Synthesis of Intermediate 2-9

A solution of 18.7 g (142.0 mmol) of 1-indanone and 31.7 g (142.0 mmol) of 4-bromophenylhydrazine hydrochloride in 400 ml of ethanol was added with 2.0 ml of concentrated sulfuric acid. The resultant mixture was stirred for 8 h while refluxing under heating. The reaction solution was allowed to stand for cooling, and then, the precipitate was collected by filtration and washed with 500 ml of methanol. By recrystallizing the crude product, 21.7 g of white solid was obtained, which was identified as the following intermediate 2-9 by FD-MS analysis (yield: 54%).

Intermediate 2-9

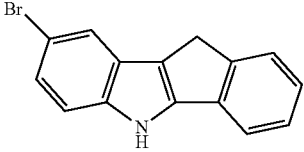

Synthesis Example 1: Production of Aromatic Heterocyclic Derivative (H1)

In an argon atmosphere, 50 ml of dehydrated xylene was added to a mixture of 3.2 g (10.0 mmol) of intermediate 1-5, 3.3 g (10.0 mmol) of intermediate 2-1, 0.14 g (0.15 mmol) of $Pd_2(dba)_3$, 0.087 g (0.3 mmol) of $P(tBu)_3HBF_4$, and 1.9 g (20.0 mmol) of sodium t-butoxide. The resultant mixture was refluxed for 8 h under heating.

After the reaction, the reaction solution was cooled to 50° C. and filtered through celite and silica gel. The filtrate was concentrated and the obtained concentrate was purified by silica gel column chromatography, to obtain a white solid. The crude product was recrystallized from toluene, to obtain 2.9 g of white crystal, which was identified as the following aromatic heterocyclic derivative (H1) by FD-MS analysis (yield: 50%).

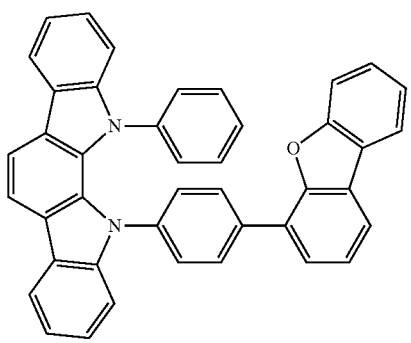

Synthesis Example 2: Production of Aromatic Heterocyclic Derivative (H12)

The reaction of Synthesis Example 1 was repeated except for using 3.2 g of intermediate 1-4 in place of intermediate 1-5, to obtain 3.0 g of white crystal, which was identified as the following aromatic heterocyclic derivative (H2) by FD-MS analysis (yield: 52%).

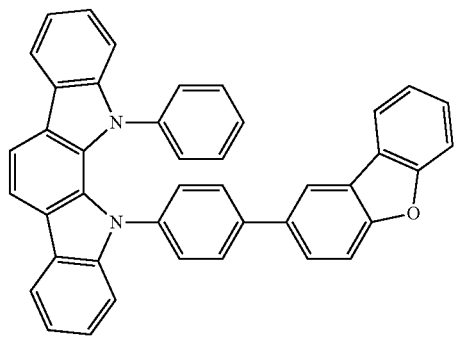

Synthesis Example 3: Production of Aromatic Heterocyclic Derivative (H3)

The reaction of Synthesis Example 1 was repeated except for using 4.4 g of intermediate 1-6 in place of intermediate 1-5, to obtain 3.7 g of white crystal, which was identified as the following aromatic heterocyclic derivative (H3) by FD-MS analysis (yield: 54%).

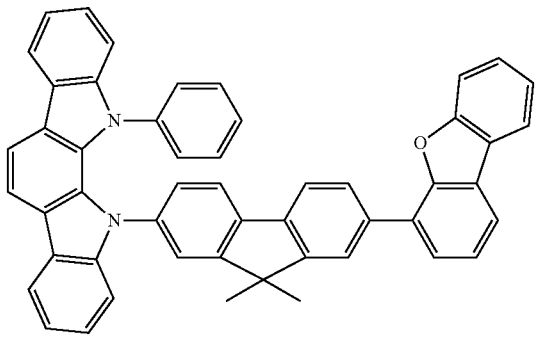

Synthesis Example 4: Production of Aromatic Heterocyclic Derivative (H4)

The reaction of Synthesis Example 1 was repeated except for using 3.3 g of intermediate 2-3 in place of intermediate 2-1, to obtain 3.0 g of white crystal, which was identified as the following aromatic heterocyclic derivative (H4) by FD-MS analysis (yield: 50%).

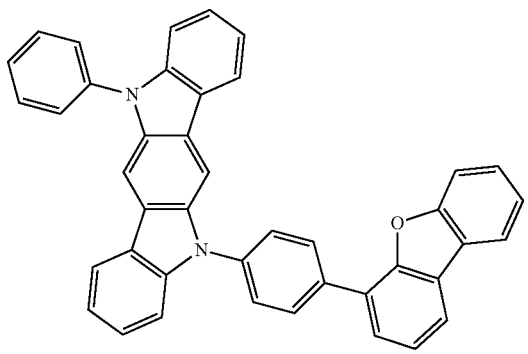

Synthesis Example 5: Production of Aromatic Heterocyclic Derivative (H5)

The reaction of Synthesis Example 1 was repeated except for using 3.2 g of intermediate 1-4 in place of intermediate 1-5 and using 3.3 g of intermediate 2-3 in place of intermediate 2-1, to obtain 2.9 g of white crystal, which was identified as the following aromatic heterocyclic derivative (H5) by FD-MS analysis (yield: 50%).

H5

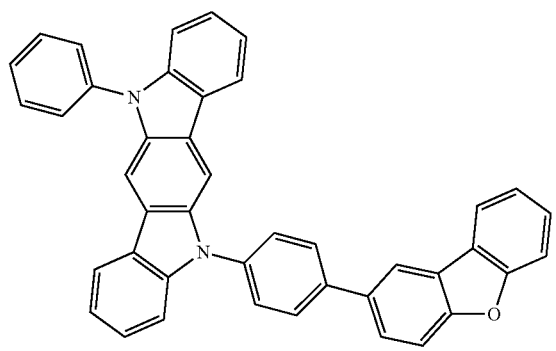

Synthesis Example 6: Production of Aromatic Heterocyclic Derivative (H6)

The reaction of Synthesis Example 1 was repeated except for using 4.4 g of intermediate 1-6 in place of intermediate 1-5 and using 3.3 g of intermediate 2-3 in place of intermediate 2-1, to obtain 3.2 g of white crystal, which was identified as the following aromatic heterocyclic derivative (H6) by FD-MS analysis (yield: 46%).

H6

Synthesis Example 7: Production of Aromatic Heterocyclic Derivative (H7)

The reaction of Synthesis Example 1 was repeated except for using 4.4 g of intermediate 1-6 in place of intermediate 1-5 and using 2.6 g of intermediate 2-5 in place of intermediate 2-1, to obtain 3.1 g of white crystal, which was identified as the following aromatic heterocyclic derivative (H7) by FD-MS analysis (yield: 50%).

H7

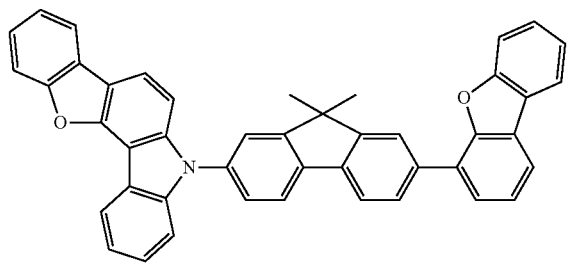

Synthesis Example 8: Production of Aromatic Heterocyclic Derivative (H8)

The reaction of Synthesis Example 1 was repeated except for using 4.4 g of intermediate 1-6 in place of intermediate 1-5 and using 2.7 g of intermediate 2-7 in place of intermediate 2-1, to obtain 3.0 g of white crystal, which was identified as the following aromatic heterocyclic derivative (H8) by FD-MS analysis (yield: 47%).

H8

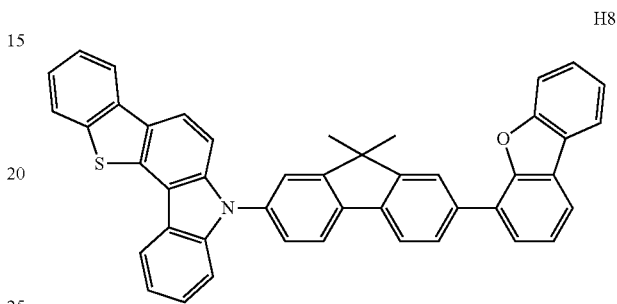

Synthesis Example 9: Production of Aromatic Heterocyclic Derivative (H9)

In an argon atmosphere, 50 ml of dehydrated 1,4-dioxane was added to a mixture of 8.8 g (20.0 mmol) of intermediate 1-6, 4.1 g (20.0 mmol) of intermediate 2-8, 3.8 g (20.0 mmol) of copper iodide, 6.9 g (60.0 mmol) of trans-1,2-cyclohexanediamine, and 12.7 g (60.0 mmol) of tripotassium phosphate. The resultant mixture was stirred for 48 h while refluxing under heating. The reaction solution was concentrated under reduced pressure. The obtained residue was added with 1000 ml of toluene, heated to 120° C., and filtered to remove the insolubles. The filtrate was concentrated under reduced pressure, and the obtained residue was purified by silica gel column chromatography, to obtain 6.0 g of white solid, which was identified as the following intermediate (9-a) by FD-MS analysis.

A mixture of 5.6 g (50.0 mmol) of potassium t-butoxide in 300 ml of dehydrated THF was cooled to 0° C., added with 5.6 g (10.0 mmol) of the white solid obtained above, and then, stirred at 0° C. for one hour. After adding 7.1 g (50.0 mmol) of methyl iodide gradually, the stirring was continued at room temperature for 4 h.

After the reaction, the reaction solution was added with 100 ml of water and extracted with dichloromethane. The organic layer was dried over MgSO$_4$, filtered, and concentrated. The concentrate was purified by silica gel column chromatography, to obtain a white solid. The crude product was recrystallized from toluene, to obtain 3.5 g of white solid, which was identified as the following aromatic heterocyclic derivative (H9) by FD-MS analysis (yield: 59%).

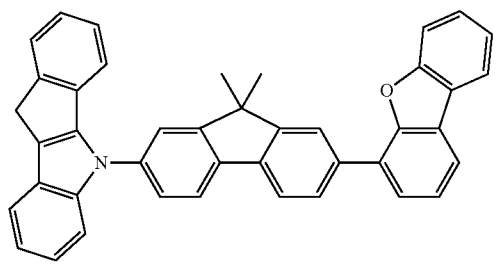

Intermediate 9-a

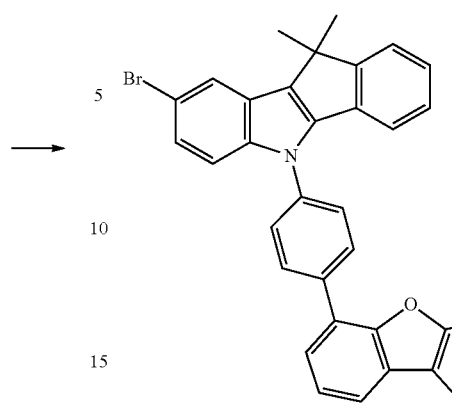

Intermediate 10-a

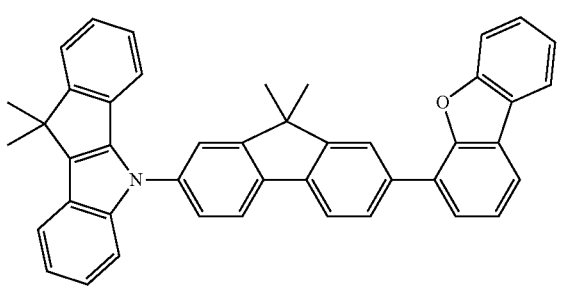

H9

Synthesis Example 10: Production of Aromatic Heterocyclic Derivative (H10)

The reaction of Synthesis Example 9 was repeated except for using 6.5 g of intermediate 1-5 in place of intermediate 1-6 and using 5.7 g of intermediate 2-9 in place of intermediate 2-8, to obtain 6.1 g of white crystal, which was identified as the following intermediate (10-a) by FD-MS analysis.

In an argon atmosphere, 10 ml (20.0 mmol) of a 2 M aqueous solution of $Na_2CO_3$, 20 ml of DME, 20 ml of toluene, and 0.58 g (0.5 mmol) of $Pd[PPh_3]_4$ were added to a mixture of 5.5 g (10.0 mmol) of intermediate 10-a and 3.4 g (12.0 mmol) of intermediate 1-8. The resultant mixture was stirred for 12 h while refluxing under heating.

After the reaction, the reaction solution was cooled to room temperature, added with 50 ml of water, and then, extracted with dichloromethane in a separatory funnel. The organic layer was dried over $MgSO_4$, filtered, and concentrated. The obtained reaction product was purified by silica gel column chromatography, to obtain a white solid. The crude product was recrystallized from toluene to obtain 3.3 g of white solid, which was identified as the following aromatic heterocyclic derivative (H10) by FD-MS analysis (yield: 45%).

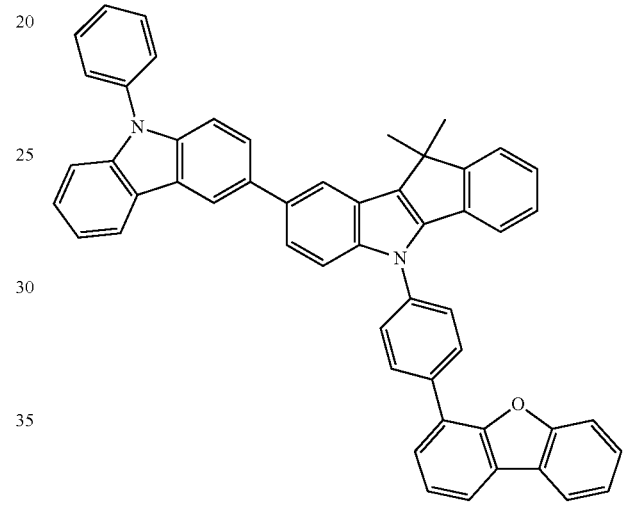

H10

Synthesis Example 11: Production of Aromatic Heterocyclic Derivative (H11)

The reaction of Synthesis Example 1 was repeated except for using 2.5 g of intermediate 1-9 in place of intermediate 1-5, to obtain 1.5 g of white crystal, which was identified as the following aromatic heterocyclic derivative (H11) by FD-MS analysis (yield: 30%).

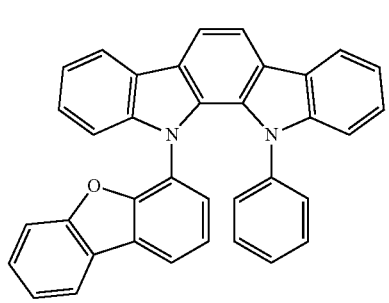

H11

Synthesis Example 12: Production of Aromatic Heterocyclic Derivative (H12)

The reaction of Synthesis Example 1 was repeated except for using 2.5 g of intermediate 1-9 in place of intermediate 1-5 and using 3.3 g of intermediate 2-3 in place of intermediate 2-1, to obtain 1.7 g of white crystal, which was identified as the following aromatic heterocyclic derivative (H12) by FD-MS analysis (yield: 34%).

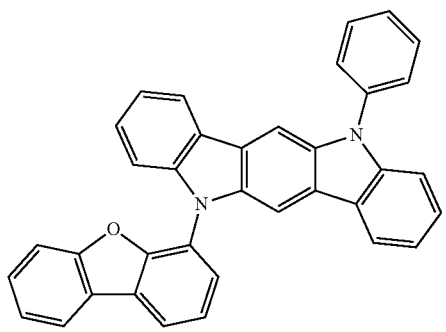

H12

Synthesis Example 13: Production of Aromatic Heterocyclic Derivative (H13)

The reaction of Synthesis Example 10 was repeated except for using 4.9 g of intermediate 1-9 in place of intermediate 1-5, to obtain 1.9 g of white crystal, which was identified as the following aromatic heterocyclic derivative (H13) by FD-MS analysis (yield: 30%).

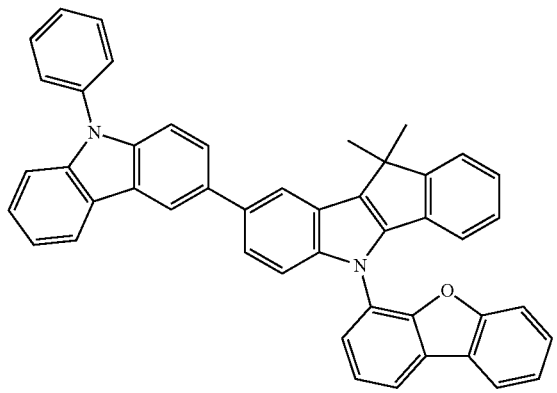

H13

Example 1

Production of Organic EL Device

A glass substrate with an ITO transparent electrode having a size of 25 mm×75 mm×1.1 mm (manufactured by GEOMATEC Co., Ltd.) was ultrasonically cleaned in isopropyl alcohol for 5 min and then UV (ultraviolet)/ozone cleaned for 30 min.

The cleaned glass substrate with the transparent electrode line was mounted on the substrate holder of a vacuum deposition apparatus. First, the following electron-accepting compound (A) was vapor-deposited onto the surface on the side where the transparent electrode line was formed so as to cover the transparent electrode, thereby forming a film A having a thickness of 5 nm. On the film A, the following aromatic amine derivative (X1) as a first hole transporting material was vapor-deposited to form a first hole transporting layer having a thickness of 157 nm. Successively after the formation of the first hole transporting layer, the aromatic heterocyclic derivative (H1) obtained in Synthesis Example 1 as a second hole transporting material was vapor-deposited to form a second hole transporting layer having a thickness of 10 nm.

On the hole transporting layer, the compound (B) (host for phosphorescence) and Ir(ppy)$_3$ (dopant for phosphorescence) were vapor co-deposited in to a film having a thickness of 40 nm, to form a phosphorescent light emitting layer. The concentration of Ir(ppy)$_3$ was 10% by mass.

Then, a film of the compound (C) having a thickness of 20 nm, a film of LiF having a thickness of 1 nm, and a film of metallic Al having a thickness of 80 nm were successively deposited to form a cathode. The LiF film as the electron injecting electrode was formed at a film-forming speed of 1 Å/min.

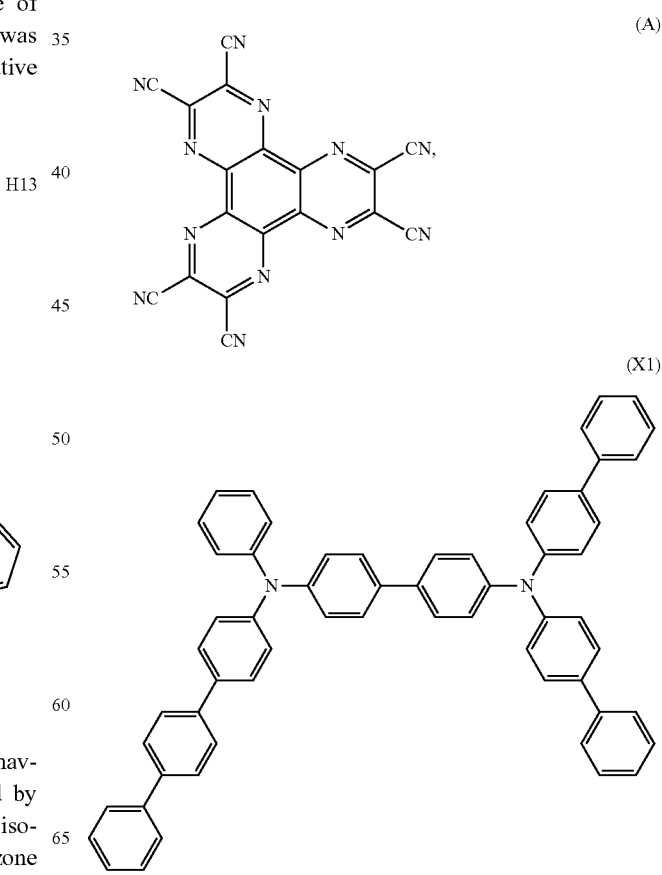

-continued (B) 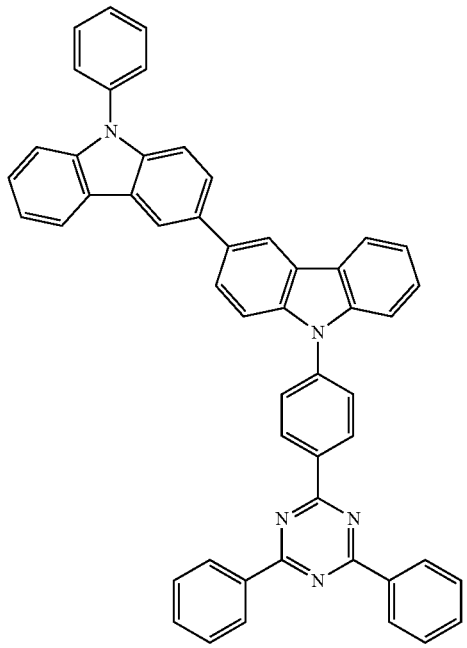

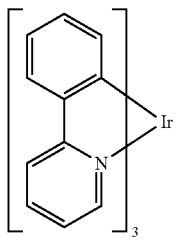
Ir(ppy)₃

(C) 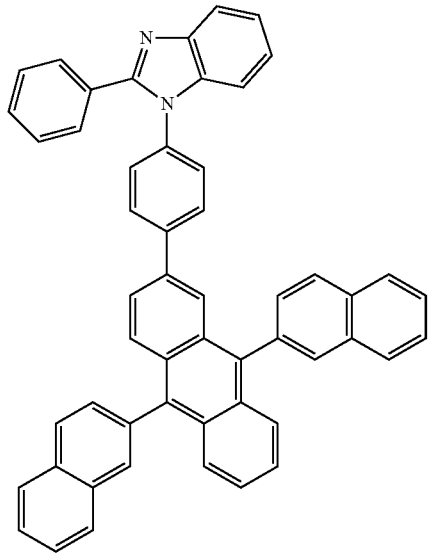

Evaluation of Emission Performance of Organic EL Device

The organic EL device thus produced was measured for the luminance (L) and the current density by allowing the device to emit light under a direct current drive, thereby determining the current efficiency (L/J) and the driving voltage (V) at a current density of 10 mA/cm². In addition, the organic EL device was measured for the lifetime at an initial luminance of 20000 cd/m². The results are shown in Table 1.

Examples 2 to 13

Each organic EL device was produced in the same manner as in Example 1 except for using each aromatic heterocyclic derivative listed in Table 1 as the second hole transporting material in place of the aromatic heterocyclic derivative (H1). Each of the obtained organic EL devices was measured for the luminance (L) and the current density by allowing the device to emit light under a direct current drive, thereby determining the current efficiency (L/J) and the driving voltage (V) at a current density of 10 mA/cm². In addition, each organic EL device was measured for the lifetime at an initial luminance of 20000 cd/m². The results are shown in Table 1.

Comparative Examples 1 to 6

Each organic EL device was produced in the same manner as in Example 1 except for using each of the following comparative compounds 1 to 6 as the second hole transporting material in place of the aromatic heterocyclic derivative (H1). Each of the obtained organic EL devices was measured for the luminance (L) and the current density by allowing the device to emit light under a direct current drive, thereby determining the current efficiency (L/J) and the driving voltage (V) at a current density of 10 mA/cm². In addition, each organic EL device was measured for the lifetime at an initial luminance of 20000 cd/m². The results are shown in Table 1.

Comparative compound 1

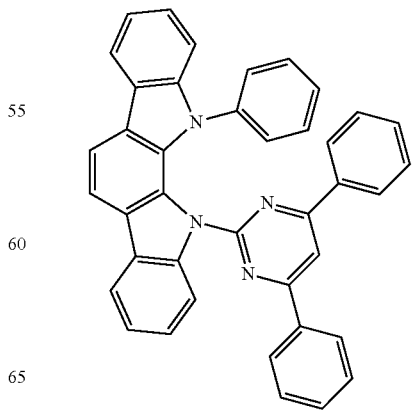

-continued

Comparative compound 2

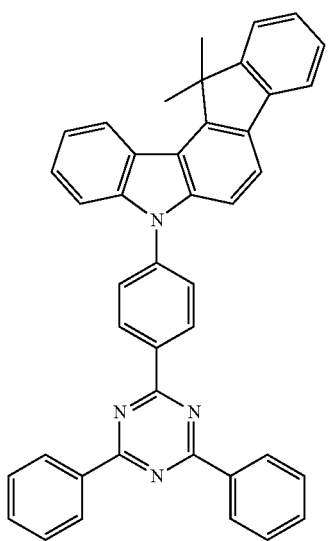

Comparative compound 3

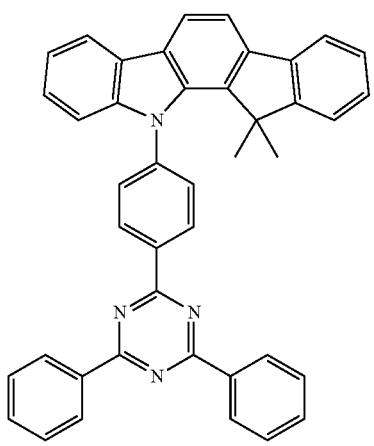

Comparative compound 4

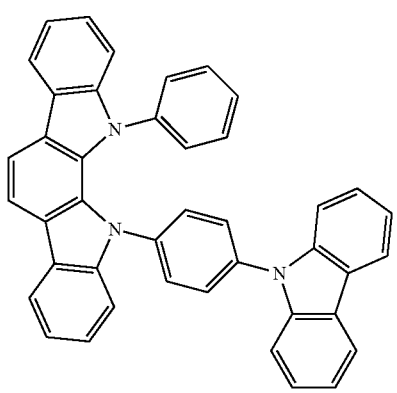

-continued

Comparative compound 5

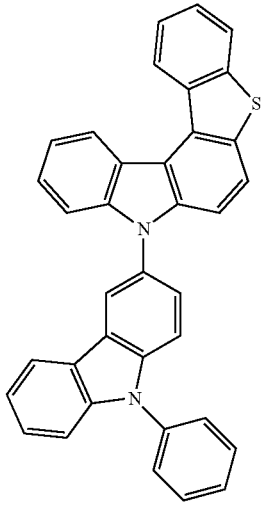

Comparative compound 6

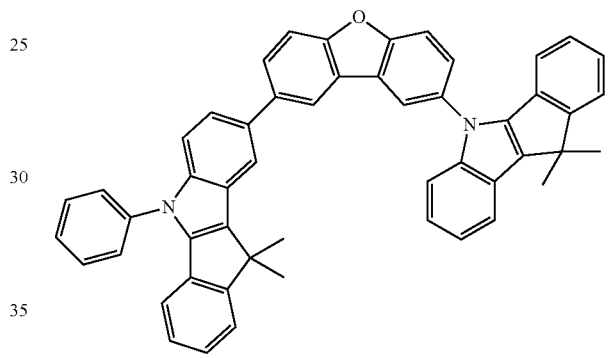

TABLE 1

| | Second hole transporting material | emission efficiency (cd/A) @ 10 mA/cm² | driving voltage (V) @ 10 mA/cm² | 80% lifetime (h) |
|---|---|---|---|---|
| Examples | | | | |
| 1 | H1 | 56.5 | 4.1 | 135 |
| 2 | H2 | 54.2 | 4.1 | 120 |
| 3 | H3 | 55.3 | 4.2 | 125 |
| 4 | H4 | 54.2 | 3.8 | 120 |
| 5 | H5 | 53.7 | 3.8 | 100 |
| 6 | H6 | 53.6 | 3.8 | 110 |
| 7 | H7 | 58.5 | 4.3 | 150 |
| 8 | H8 | 58.7 | 4.3 | 150 |
| 9 | H9 | 59.2 | 4.0 | 150 |
| 10 | H10 | 59.5 | 4.0 | 150 |
| 11 | H11 | 61.2 | 4.2 | 135 |
| 12 | H12 | 60.5 | 4.0 | 125 |
| 13 | H13 | 61.2 | 4.2 | 150 |
| Comparative Examples | | | | |
| 1 | comparative compound 1 | 37.2 | 4.5 | 50 |
| 2 | comparative compound 2 | 37.0 | 4.3 | 40 |
| 3 | comparative compound 3 | 36.6 | 4.3 | 40 |

TABLE 1-continued

| | Second hole transporting material | emission efficiency (cd/A) @ 10 mA/cm² | driving voltage (V) @ 10 mA/cm² | 80% lifetime (h) |
|---|---|---|---|---|
| 4 | comparative compound 4 | 50.5 | 4.1 | 100 |
| 5 | comparative compound 5 | 53.4 | 4.0 | 20 |
| 6 | comparative compound 6 | 50.2 | 4.1 | 100 |

Upon comparing Example 1 with Example 2 or comparing Example 4 with Example 5, it can be found that a preferred result is obtained when $L_2$ is boned at the 4-position of the structure represented by formula (1c).

Upon comparing Example 1 with Example 3 or comparing Example 4 with Example 6, it can be found that a preferred result is obtained when $L_2$ is a phenylene group.

Upon comparing Examples 7 and 8 with Example 9 or Example 10, it can be found that a preferred result is obtained when X is $CR_6R_7$.

Upon comparing Examples 9 to 13, it can be found that $L_2$ is preferably a phenylene group or a single bond and particularly preferably a single bond, and further found that X is preferably $CR_6R_7$.

As seen from Table 1, the nitrogen-containing aromatic heterocyclic derivative of the invention is useful as the material for realizing a long-lifetime organic EL device capable of driving at high efficiency.

INDUSTRIAL APPLICABILITY

As described in detail, a highly efficient long-lifetime organic EL device can be obtained by using the nitrogen-containing aromatic heterocyclic derivative of the invention. Therefore, the organic EL device of the invention is extremely useful as light source of various electronic equipments, etc.

Column 151, formula (3-1):
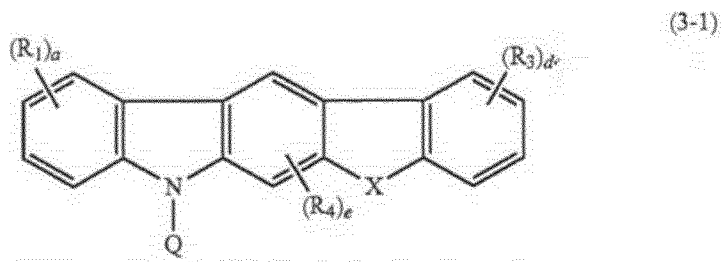
Should be replaced with the following formula (3-1):
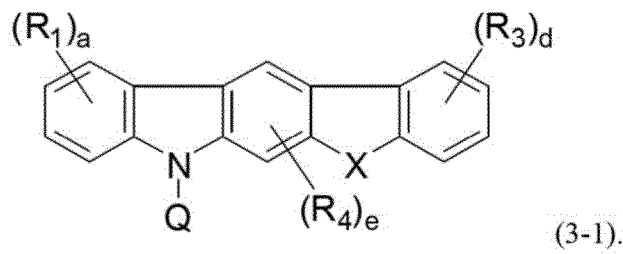
Column 151, Line 17, "an acyl group" should read --an aryl group--
Column 152, formula (3-2):
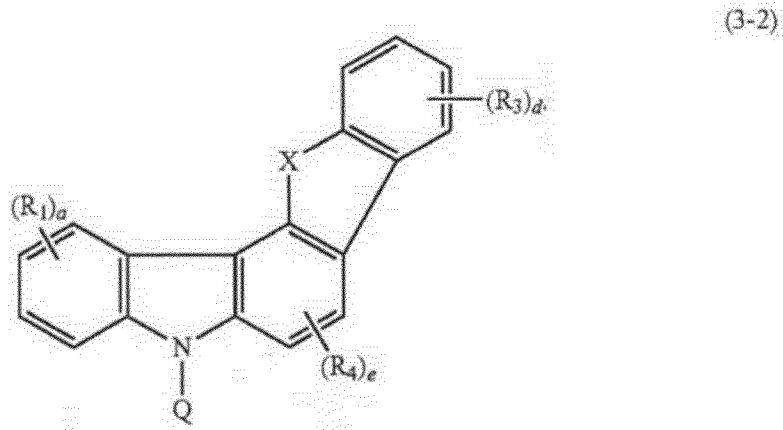
Should be replaced with formula (3-2):
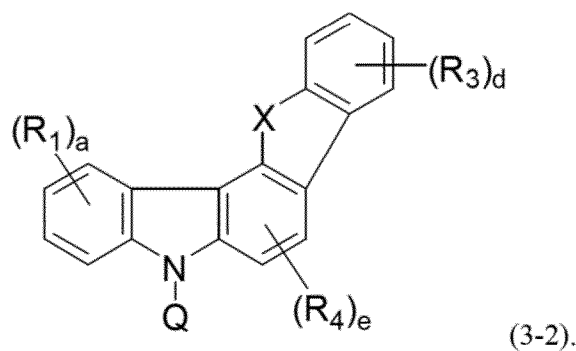

Column 153, formula (4-1):
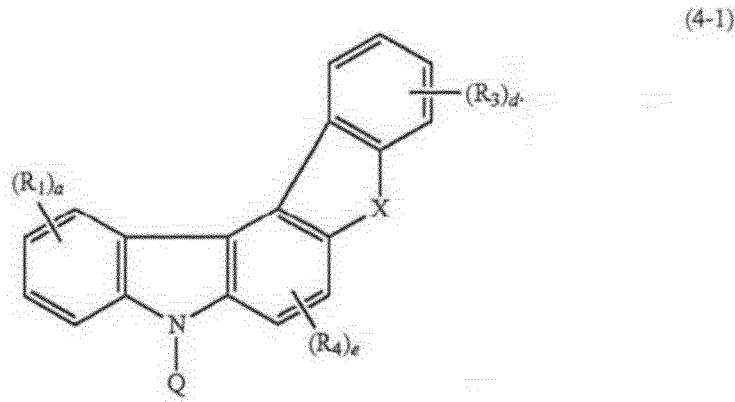
Should be replaced with formula (4-1):
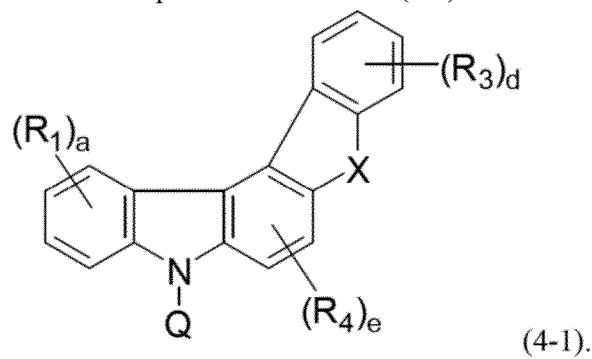

What is claimed is:

1. An aromatic heterocyclic derivative selected from the group consisting of formulae (2-1), (3-1), (3-2) and (4-1):

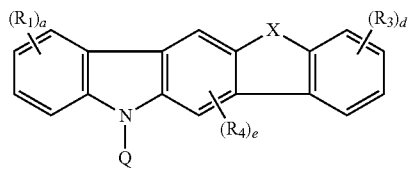

(2-1)

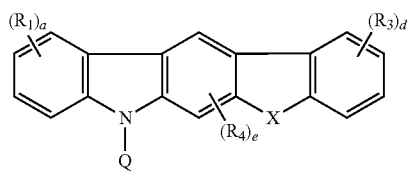

(3-1)

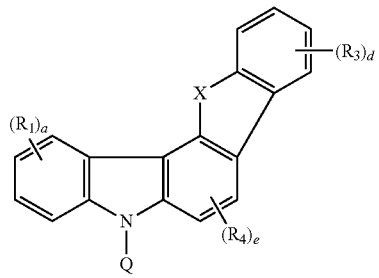

(3-2)

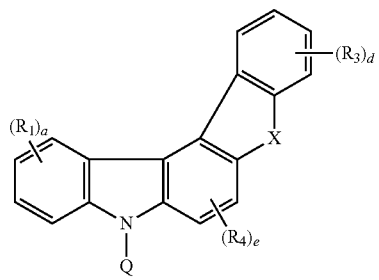

(4-1)

wherein:

X is $NR_5$;

each of $R_1$ and $R_3$ to $R_5$ independently represents a linear or branched alkyl group comprising from 1 to 15 carbon atoms, a cycloalkyl group comprising from 3 to 15 ring carbon atoms, a substituted or unsubstituted silyl group, an aryl group having 6 to 30 ring carbon atoms, a heteroaryl group comprising from 5 to 30 ring atoms, a halogen atom, or a cyano group, or adjacent two groups of $R_1$ and $R_3$ to $R_5$ are bonded to each other to from a saturated or unsaturated divalent group which completes a ring;

each of a and d independently represents an integer of 0 to 4;

e represents an integer of 0 to 2; and

Q represents a structure represented by formula (1c):

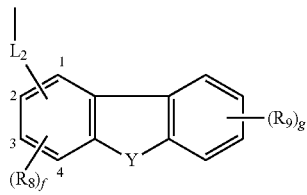

(1c)

wherein:

Y represents an oxygen atom or a sulfur atom;

$L_2$ represents a structure represented by any one of formulae (7a) to (7c):

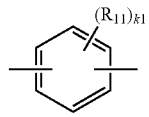

(7a)

-continued

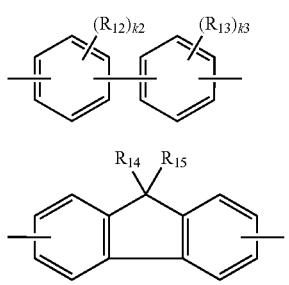

(7b)

(7c)

wherein
each of $R_{11}$ to $R_{13}$ independently represents a linear or branched alkyl group comprising from 1 to 15 carbon atoms, a cycloalkyl group comprising from 3 to 15 ring carbon atoms, a substituted or an unsubstituted silyl group, an aryl group comprising from 6 to 20 ring carbon atoms, a heteroaryl group comprising from 5 to 20 ring atoms, a halogen atom, or a cyano group, or adjacent two groups of $R_{11}$ to $R_{13}$ are bonded to each other to from a saturated or an unsaturated divalent group which completes a ring;
each of $R_{14}$ and $R_{15}$ independently represents a linear or branched alkyl group comprising from 1 to 15 carbon atoms, a cycloalkyl group comprising from 3 to 15 ring carbon atoms, an aryl group comprising from 6 to 20 ring carbon atoms, or a heteroaryl group comprising from 5 to 20 ring atoms; and
each of k1 to k3 independently represents an integer of 0 to 4;
$L_2$ is bonded to a carbon atom at a 4-position of the structure represented by formula (1c);
each of $R_8$ and $R_9$ independently represents a linear or branched alkyl group comprising from 1 to 15 carbon atoms, a cycloalkyl group comprising from 3 to 15 ring carbon atoms, a substituted or an unsubstituted silyl group, an aryl group comprising from 6 to 30 ring carbon atoms, a heteroaryl group comprising from 5 to 30 ring atoms, a halogen atom, or a cyano group, or adjacent too groups of $R_8$ and $R_9$ are bonded to each other to from a saturated or an unsaturated divalent group which completes a ring;
f represents an integer of 0 to 3; and
g represents an integer of 0 to 4.

2. The aromatic heterocyclic derivative according to claim 1, wherein Y represents an oxygen atom.

3. The aromatic heterocyclic derivative according to claim 1, wherein Y represents a sulfur atom.

4. A material for organic electroluminescence device, comprising the aromatic heterocyclic derivative according to claim 1.

5. A hole transporting material for organic electroluminescence device, comprising the aromatic heterocyclic derivative according to claim 1.

6. An organic electroluminescence device, comprising:
a light emitting layer, and
organic thin film layers between an anode and a cathode, wherein at least one of the organic thin film layers comprises the aromatic heterocyclic derivative according to claim 1.

7. The organic electroluminescence device according to claim 6, wherein
the organic thin film layers comprise a hole transporting layer, and
the hole transporting layer comprises the aromatic heterocyclic derivative.

8. The organic electroluminescence device according to claim 7, wherein
the hole transporting layer contacts a layer comprising a compound represented by formula (A):

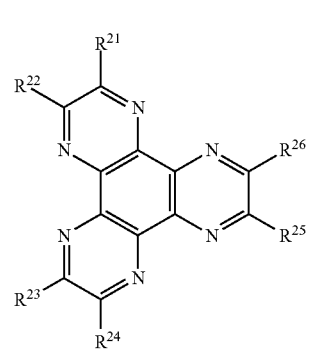

(A)

$R^{21}$ to $R^{26}$ each independently represent a cyano group, —$CONH_2$, a carboxyl group, or —$COOR^{27}$,
$R^{27}$ represents an alkyl group comprising from 1 to 20 carbon atoms or a cycloalkyl group comprising from 3 to 20 carbon atoms; and
one or more of a pair of $R^{21}$ and $R^{22}$, a pair of $R^{23}$ and $R^{24}$, and a pair of $R^{25}$ and $R^{26}$ optionally bond to each other to form a group represented by —CO—O—CO—.

9. The organic electroluminescence device according to claim 6, wherein the light emitting layer comprises a phosphorescent material.

10. The organic electroluminescence device according to claim 9, wherein the phosphorescent material is an ortho metallated complex of a metal selected from the group consisting of iridium (Ir), osmium (Os) and platinum (Pt).

11. The aromatic heterocyclic derivative according to claim 1, wherein $R_5$ is a heteroaryl group and is selected from the group consisting of a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a carbazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group.

12. The aromatic heterocyclic derivative according to claim 1, wherein $R_5$ is a linear or branched alkyl group comprising from 1 to 15 carbon atoms, a cycloalkyl group comprising from 3 to 15 ring carbon atoms, a substituted or unsubstituted silyl group, an aryl group having 6 to 30 ring carbon atoms, a halogen atom, or a cyano group.

13. The aromatic heterocyclic derivative according to claim 1, wherein

R$_5$ represents a linear or branched alkyl group comprising from 1 to 15 carbon atoms, a cycloalkyl group comprising from 3 to 15 ring carbon atoms, a substituted or unsubstituted silyl group, an aryl group having 6 to 30 ring carbon atoms, a halogen atom, or a cyano group, Y represents an oxygen atom, and L$_2$ is bonded to a carbon atom at 4-position of the structure represented by formula (1c).

14. The aromatic heterocyclic derivative according to claim 1, wherein

R$_5$ represents a linear or branched alkyl group comprising from 1 to 15 carbon atoms, a cycloalkyl group comprising from 3 to 15 ring carbon atoms, a substituted or unsubstituted silyl group, an acyl group having 6 to 30 ring carbon atoms, a halogen atom, or a cyano group, Y represents an oxygen atom, L$_2$ represents a structure represented by any one of formulae (7a) to (7c):

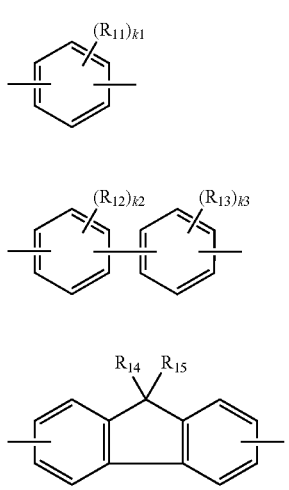

(7a)

(7b)

(7c)

each of R$_{11}$ to R$_{13}$ independently represents a linear or branched alkyl group comprising from 1 to 15 carbon atoms, a cycloalkyl group comprising from 3 to 15 ring carbon atoms, a substituted or unsubstituted silyl group, an aryl group comprising from 6 to 20 ring carbon atoms, a heteroaryl group comprising from 5 to 20 ring atoms, a halogen atom, or a cyano group, or adjacent two groups of R$_{11}$ to R$_{13}$ are bonded to each other to from a saturated or unsaturated divalent group which completes a ring;

each of R$_{14}$ and R$_{15}$ independently represents a linear or branched alkyl group comprising from 1 to 15 carbon atoms, a cycloalkyl group comprising from 3 to 15 ring carbon atoms, an aryl group having 6 to 20 ring carbon atoms, or a heteroaryl group comprising from 5 to 20 ring atoms; and each of k1 to k3 independently represents an integer of 0 to 4, and L$_2$ is bonded to a carbon atom at 4-position of the structure represented by formula (1c).

15. The aromatic heterocyclic derivative according to claim 1, which is of formula (2-1):

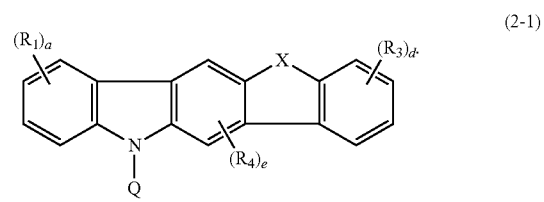

(2-1)

16. The aromatic heterocyclic derivative according to claim 15, wherein

R$_5$ represents a linear or branched alkyl group comprising from 1 to 15 carbon atoms, a cycloalkyl group comprising from 3 to 15 ring carbon atoms, a substituted or unsubstituted silyl group, an aryl group having 6 to 30 ring carbon atoms, a halogen atom, or a cyano group, Y represents an oxygen atom, L$_2$ represents a structure represented by any one of formulae (7a) to (7c):

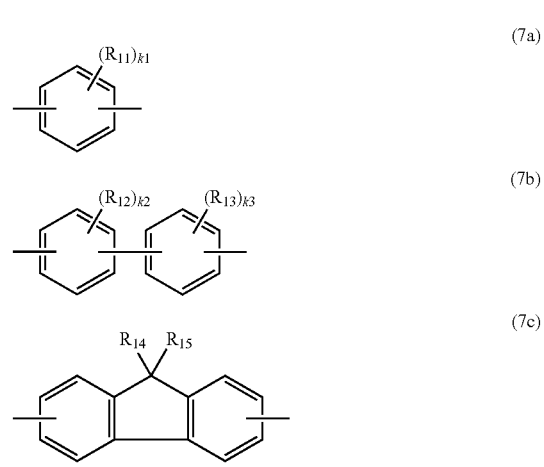

(7a)

(7b)

(7c)

each of R$_{11}$ to R$_{13}$ independently represents a linear or branched alkyl group comprising from 1 to 15 carbon atoms, a cycloalkyl group comprising from 3 to 15 ring carbon atoms, a substituted or unsubstituted silyl group, an aryl group comprising from 6 to 20 ring carbon atoms, a heteroaryl group comprising from 5 to 20 ring atoms, a halogen atom, or a cyano group, or adjacent two ups of R$_{11}$ to R$_{13}$ are bonded to each other to from a saturated or unsaturated divalent group which completes a ring;

each of R$_{14}$ and R$_{15}$ independently represents a linear or branched alkyl group comprising from 1 to 15 carbon atoms, a cycloalkyl group comprising from 3 to 15 ring carbon atoms, an aryl group having 6 to 20 ring carbon atoms, or a heteroaryl group comprising from 5 to 20 ring atoms; and each of k1 to k3 independently represents an integer of 0 to 4, and L$_2$ is bonded to a carbon atom at 4-position of the structure represented by formula (1c).

17. The aromatic heterocyclic derivative according to claim 1, which is of formula (3-1):

(3-1)

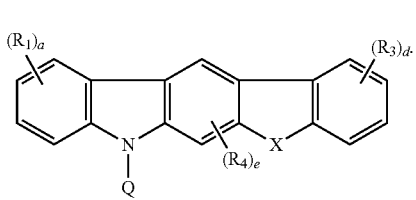

18. The aromatic heterocyclic derivative according to claim 17, wherein $R_5$ represents a linear or branched alkyl group comprising from 1 to 15 carbon atoms, a cycloalkyl group comprising from 3 to 15 ring carbon atoms, a substituted or unsubstituted silyl group, an acyl group having 6 to 30 ring carbon atoms, a halogen atom, or a cyano group, Y represents an oxygen atom, $L_2$ represents a structure represented by any one of formulae (7a) to (7c):

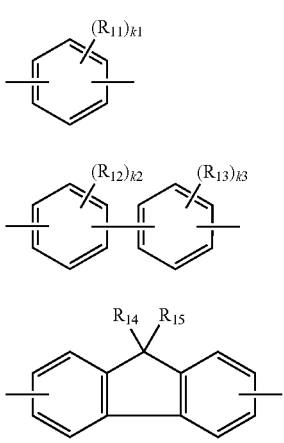

(7a)

(7b)

(7c)

each of $R_{11}$ to $R_{13}$ independently represents a linear or branched alkyl group comprising from 1 to 15 carbon atoms, a cycloalkyl group comprising from 3 to 15 ring carbon atoms, a substituted or unsubstituted silyl group, an aryl group comprising from 6 to 20 ring carbon atoms, a heteroaryl group comprising from 5 to 20 ring atoms, a halogen atom, or a cyano group, or adjacent two groups of $R_{11}$ to $R_{13}$ are bonded to each other to from a saturated or unsaturated divalent group which completes a ring;

each of $R_{14}$ and $R_{15}$ independently represents a linear or branched alkyl group comprising from 1 to 15 carbon atoms, a cycloalkyl group comprising from 3 to 15 ring carbon atoms, an aryl group having 6 to 20 ring carbon atoms, or a heteroaryl group comprising from 5 to 20 ring atoms; and each of k1 to k3 independently represents an integer of 0 to 4, and $L_2$ is bonded to a carbon atom at 4-position of the structure represented by formula (1c).

19. The aromatic heterocyclic derivative according to claim 1, which is of formula (3-2):

(3-2)

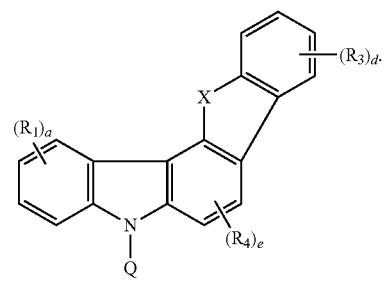

20. The aromatic heterocyclic derivative according to claim 19, wherein $R_5$ represents a linear or branched alkyl group comprising from 1 to 15 carbon atoms, a cycloalkyl group comprising from 3 to 15 ring carbon atoms, a substituted or unsubstituted silyl group, an aryl group having 6 to 30 ring carbon atoms, a halogen atom, or a cyano group, Y represents an oxygen atom, $L_2$ represents a structure represented by any one of formulae (7a) to (7c):

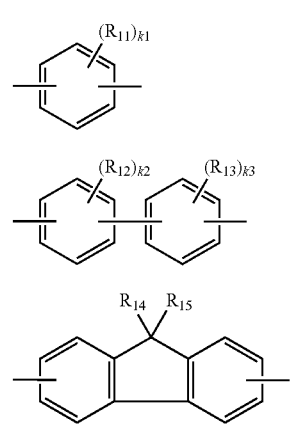

(7a)

(7b)

(7c)

each of $R_{11}$ to $R_{13}$ independently represents a linear or branched alkyl group comprising from 1 to 15 carbon atoms, a cycloalkyl group comprising from 3 to 15 ring carbon atoms, a substituted or unsubstituted silyl group, an aryl group comprising from 6 to 20 ring carbon atoms, a heteroaryl group comprising from 5 to 20 ring atoms, a halogen atom, or a cyano group, or adjacent two groups of $R_{11}$ to $R_{13}$ are bonded to each other to from a saturated or unsaturated divalent group which completes a ring;

each of $R_{14}$ and $R_{15}$ independently represents a linear or branched alkyl group comprising from 1 to 15 carbon atoms, a cycloalkyl group comprising from 3 to 15 ring carbon atoms, an aryl group having 6 to 20 ring carbon atoms, or a heteroaryl group comprising from 5 to 20 ring atoms; and each of k1 to k3 independently represents an integer of 0 to 4, and $L_2$ is bonded to a carbon atom at 4-position of the structure represented by formula (1c).

21. The aromatic heterocyclic derivative according to claim 1, which is of formula (4-1):

(4-1)

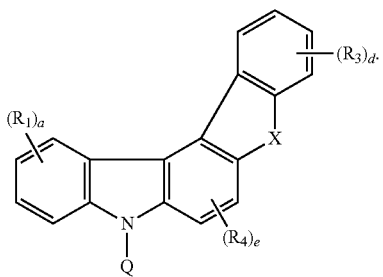

22. The aromatic heterocyclic derivative according to claim 21, wherein $R_5$ represents a linear or branched alkyl group comprising from 1 to 15 carbon atoms, a cycloalkyl group comprising from 3 to 15 ring carbon atoms, a substituted or unsubstituted silyl group, an aryl group having 6 to 30 ring carbon atoms, a halogen atom, or a cyano group, Y represents an oxygen atom, $L_2$ represents a structure represented by any one of formulae (7a) to (7c):

(7a)

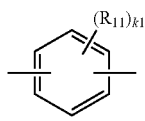

(7b)

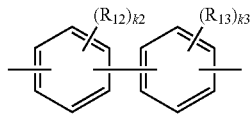

(7c)

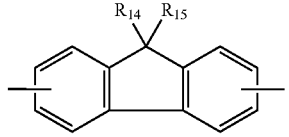

each of $R_{11}$ to $R_{13}$ independently represents a linear or branched alkyl group comprising from 1 to 15 carbon atoms, a cycloalkyl group comprising from 3 to 15 ring carbon atoms, a substituted or unsubstituted silyl group, an aryl group comprising from 6 to 20 ring carbon atoms, a heteroaryl group comprising from 5 to 20 ring atoms, a halogen atom, or a cyano group, or adjacent two groups of $R_{11}$ to $R_{13}$ are bonded to each other to from a saturated or unsaturated divalent group which completes a ring;

each of $R_{14}$ and $R_{15}$ independently represents a linear or branched alkyl group comprising from 1 to 15 carbon atoms, a cycloalkyl group comprising from 3 to 15 ring carbon atoms, an aryl group having 6 to 20 ring carbon atoms, or a heteroaryl group comprising from 5 to 20 ring atoms; and each of k1 to k3 independently represents an integer of 0 to 4, and $L_2$ is bonded to a carbon atom at 4-position of the structure represented by formula (1c).

* * * * *

UNITED STATES PATENT AND TRADEMARK OFFICE
CERTIFICATE OF CORRECTION

PATENT NO. : 10,043,977 B2
APPLICATION NO. : 14/233066
DATED : August 7, 2018
INVENTOR(S) : Tomoki Kato et al.

It is certified that error appears in the above-identified patent and that said Letters Patent is hereby corrected as shown below:

In the Claims

Column 147, Line 43, "adjacent too groups" should read --adjacent two groups--

Column 150, formula (2-1):

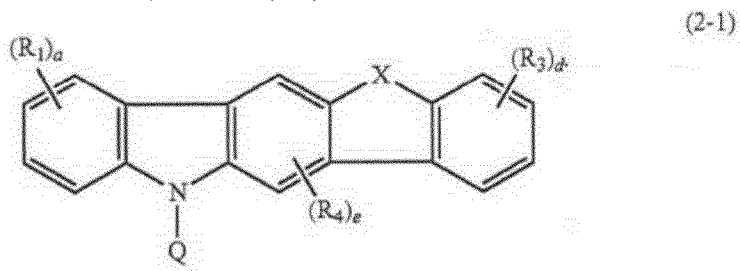

Should be replaced with the following formula (2-1):

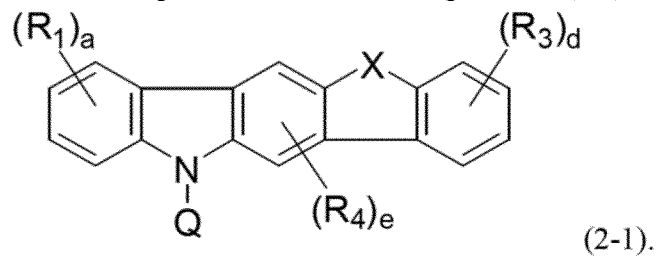

(2-1).

Column 150, Line 51, "adjacent two ups of" should read --adjacent two groups of--

Signed and Sealed this
Eighteenth Day of June, 2019

Andrei Iancu
*Director of the United States Patent and Trademark Office*